US011638752B2

(12) United States Patent
Bauche et al.

(10) Patent No.: US 11,638,752 B2
(45) Date of Patent: May 2, 2023

(54) VIRAL VECTOR CONSTRUCTS FOR EXPRESSION OF GENETIC ADJUVANTS ACTIVATING THE STING PATHWAY

(71) Applicant: aratinga.bio AIO, Villejuif (FR)

(72) Inventors: Cécile Bauche, Paris (FR); Renaud Vaillant, Gentilly (FR); Emeline Sarry, Malakoff (FR); Frédéric Mourlane, Nice (FR)

(*) Notice: Subject to any disclaimer, the term of this patent is extended or adjusted under 35 U.S.C. 154(b) by 916 days.

(21) Appl. No.: 16/464,492

(22) PCT Filed: Nov. 28, 2017

(86) PCT No.: PCT/IB2017/001540
§ 371 (c)(1),
(2) Date: May 28, 2019

(87) PCT Pub. No.: WO2018/096395
PCT Pub. Date: May 31, 2018

(65) Prior Publication Data
US 2019/0328872 A1    Oct. 31, 2019

Related U.S. Application Data

(60) Provisional application No. 62/426,855, filed on Nov. 28, 2016.

(51) Int. Cl.
| | | |
|---|---|---|
| *A61K 39/00* | (2006.01) | |
| *C07K 14/705* | (2006.01) | |
| *A61K 38/17* | (2006.01) | |
| *A61K 39/395* | (2006.01) | |
| *A61P 35/00* | (2006.01) | |
| *A61K 39/39* | (2006.01) | |
| *C07K 14/005* | (2006.01) | |
| *C07K 14/47* | (2006.01) | |
| *C12N 15/86* | (2006.01) | |

(52) U.S. Cl.
CPC ........... *A61K 39/39* (2013.01); *C07K 14/005* (2013.01); *C07K 14/4705* (2013.01); *C12N 15/86* (2013.01); *A61K 2039/53* (2013.01); *A61K 2039/6031* (2013.01); *C07K 2319/02* (2013.01); *C07K 2319/03* (2013.01); *C12N 2710/16222* (2013.01); *C12N 2710/16234* (2013.01); *C12N 2740/16034* (2013.01)

(58) Field of Classification Search
CPC ............... A61P 35/00; A61K 38/00; A61K 2039/505; A61K 38/1774; C07K 2319/03
See application file for complete search history.

(56) References Cited

FOREIGN PATENT DOCUMENTS

| WO | WO2014039961 | * | 3/2014 |
| WO | 2017/100338 A1 | | 6/2017 |

OTHER PUBLICATIONS

Gupta, S. et al., Constitutively Active MAVS Inhibits HIV-1 Replication via Type I Interferon Secretion and Induction of HIV-1 Restriction Factors, PLOS ONE, vol. 11, No. 2, Feb. 5, 2016, 25 pgs.
Gupta, S. et al., "EBV LMP1, a viral mimic of CD40, activates dendritic cells and functions as a molecular adjuvant when incorporated into an HIV vaccine", Journal of Leukocyte Biology, vol. 90, No. 2, Aug. 1, 2011, pp. 389-398.
Kobiyama, K. et al., "A Signaling Polypeptide Derived from an Innate Immune Adaptor Molecule Can be Harnessed as a New Class of Vaccine Adjuvant", The Journal of Immunology, vol. 182, No. 3, Feb. 1, 2009, pp. 1593-1601.

* cited by examiner

*Primary Examiner* — Barry A Chestnut
(74) *Attorney, Agent, or Firm* — Verrill Dana, LLP

(57) ABSTRACT

Viral vectors are provided for use as genetic immunotherapeutic agents, including preventive and therapeutic vaccines as well as compositions to enhance cellular immune responses. The vectors are particularly useful for treating or preventing cancer and infectious diseases. The vectors include lentiviral vectors that encode one or more antigens and an adjuvant, and optionally may encode one or more soluble checkpoint inhibitor molecules. The adjuvant is a fusion protein including latent membrane protein 1 (LMP1) from Epstein Barr virus with in which the intracytoplasmic domain has been replaced by human IPS1 or a variant thereof capable of activating the STING pathway. The vector-encoded sequences are codon optimized for human expression.

13 Claims, 38 Drawing Sheets

Specification includes a Sequence Listing.

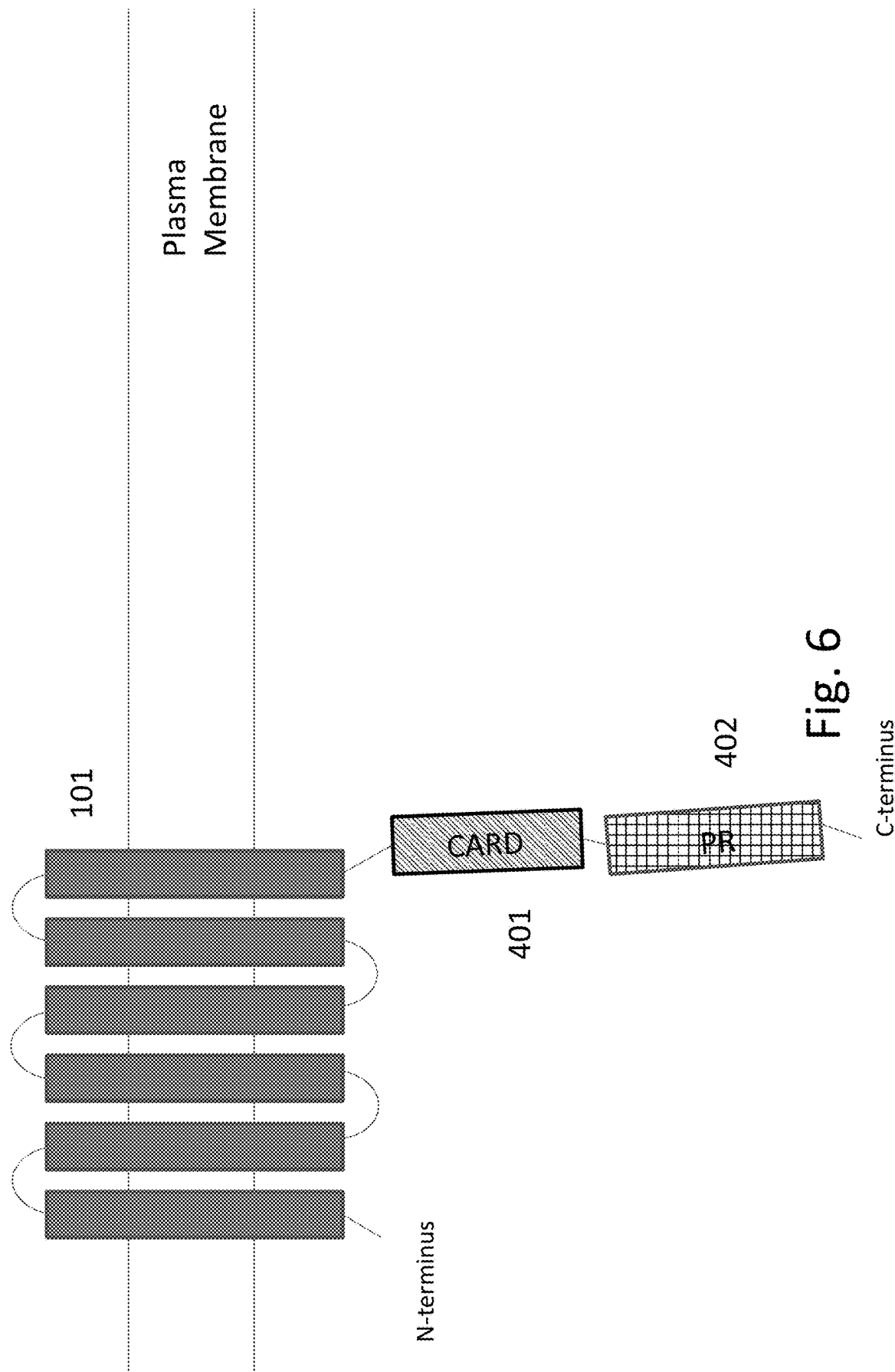

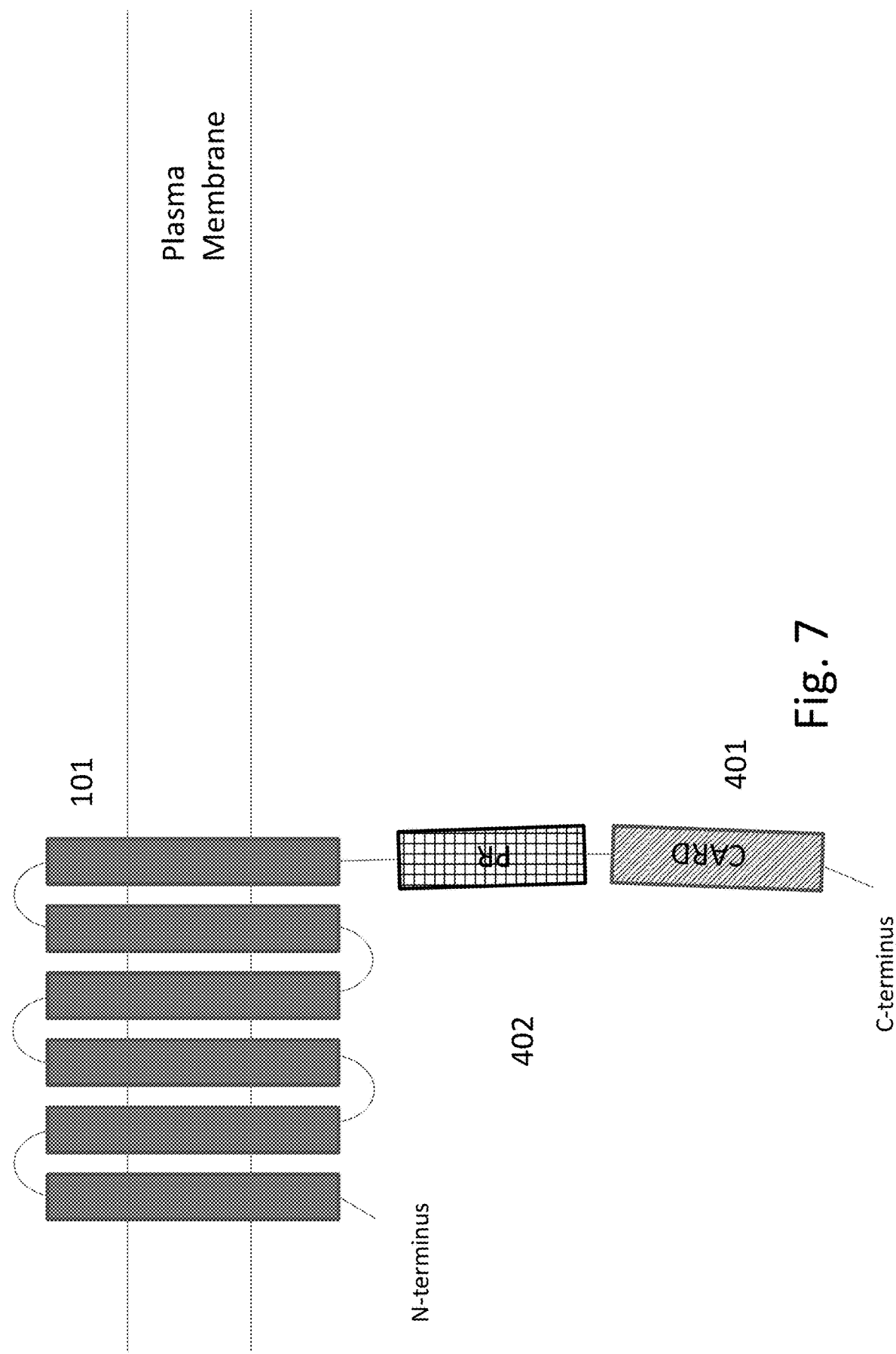

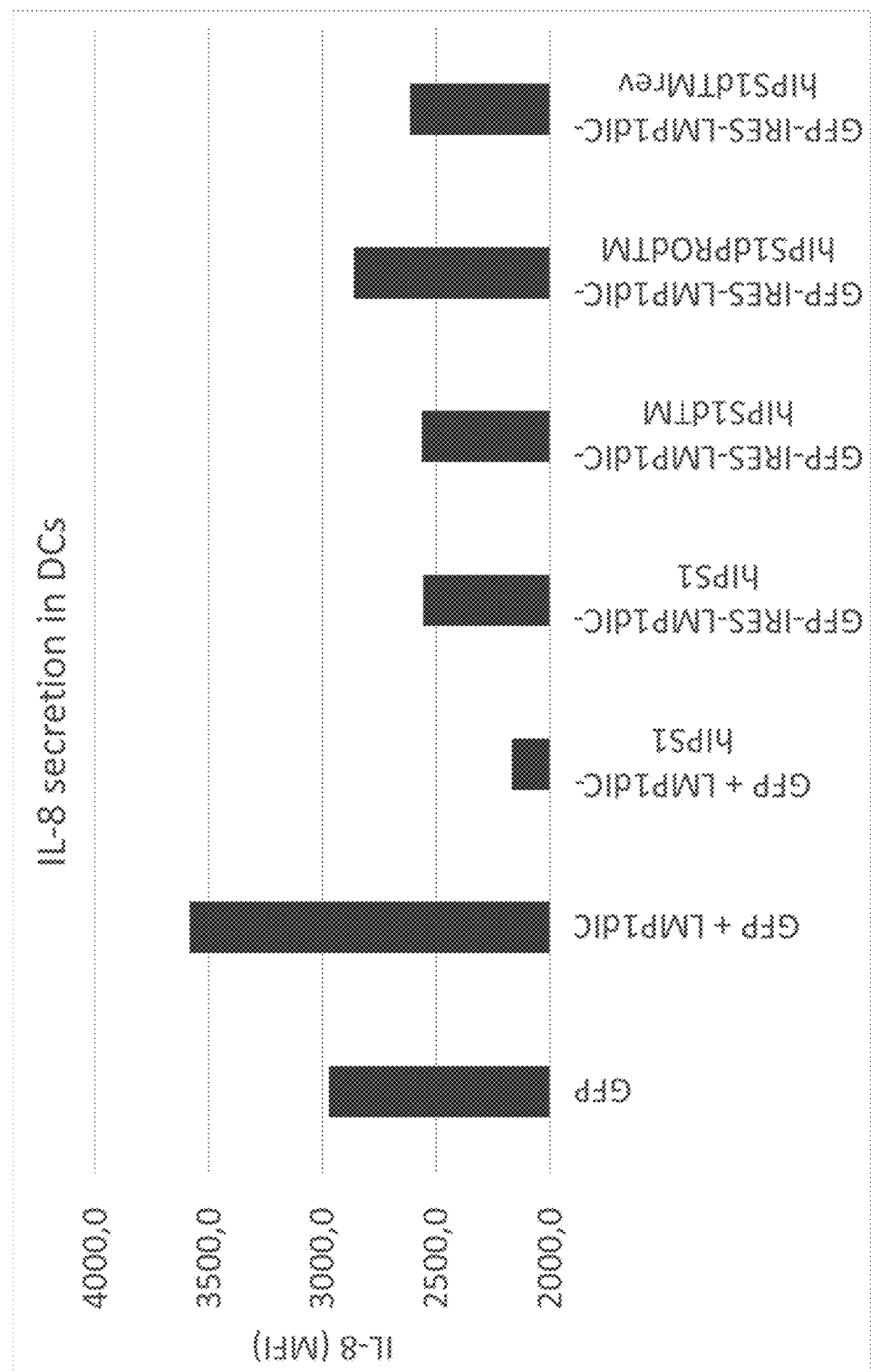

VIRAL VECTOR CONSTRUCTS FOR EXPRESSION OF GENETIC ADJUVANTS ACTIVATING THE STING PATHWAY

This application claims priority to U.S. Provisional Appl. No. 62/426,855, filed 28 Nov. 2016, which is hereby incorporated by reference in its entirety.

BACKGROUND

Canonical vaccine strategies based on the induction of antibody-based immune response have resulted in the eradication or near eradication of a number of previously fatal infectious diseases, such as smallpox, poliomyelitis and tetanus. Yet, these classical human vaccines have either been ineffective or unsafe for use in other infectious diseases, such as HIV and hepatitis, and for non-infectious illnesses such as cancer.

A new generation of immunotherapeutic products, aimed at inducing cellular immune responses, may overcome the limitations of traditional vaccines by recognizing and killing cancer cells and infected cells instead of the pathogen itself. Nucleic acid vaccines, and particularly viral vectors, have shown great potential to translate to the clinics.

Cancer cells and many infectious agents have ways of eluding the immune system, which makes creating effective vaccines difficult. Classical vaccines often require an adjuvant, e.g., aluminum salts, for optimal effectiveness, but conventional adjuvants are typically poor enhancers of cellular immune responses. Some strategies have been proposed to improve the quality and magnitude of the cellular immune response elicited by viral vectors. A new class of genetic adjuvants has been developed to improve cellular immune responses induced by vector-based immunotherapy. Genetic adjuvants consist of DNA sequences that encode immune regulatory molecules.

Stone et al. (WO 2014/039961) discloses the use of a genetic adjuvant that induces the secretion of interferon alpha and beta and thus induces the expression of interferon-stimulated genes. In this approach, a nucleic acid vaccine encodes, optionally in addition to a transgene encoding a marker protein or antigen, a fusion protein including the transmembrane portion of the LMP1 protein in which the intra-cytoplasmic domain has been replaced by an immune effector or adaptor protein, such as the IPS1 protein. Activation of IFN-β promoter stimulator (IPS1, also referred to as MAVS, VISA, or Cardif) generates potent T-cell responses via the STING (stimulator of interferon genes) pathway. When expressed in cells, the transmembrane domains of LMP1 spontaneously form clusters that allow the aggregation of the IPS1 into intracytoplasmic clusters, activating the STING pathway. The transmembrane domain of LMP1 fused with the full length murine IPS1 has been shown to induce the secretion of IFN-alpha, IFN-beta, and IL-6, and also to induce the expression of maturation (CD40 and CCR7) and activation markers (CD80 and CD86) in mouse macrophages.

There is a need for self-adjuvanting vaccines that induce the intense cellular immune response required to break the immune tolerance observed in such indications as cancer, HIV, and other unmet medical needs.

SUMMARY

The present technology provides viral vectors encoding genetic adjuvants for improving immune responses, particularly cell-mediated immune responses, such as those directed against cancer or infections, and methods for using the viral vectors. The antigen and adjuvant constructs of the present technology have been optimized for use in human subjects.

One aspect of the technology is a viral vector including (i) one or more transgenes encoding one or more marker proteins, antigens, epitopes, or combinations thereof, and (ii) a transgene encoding a fusion protein including the transmembrane portion of the latent membrane protein 1 (LMP1) of Epstein Barr virus in which the intra-cytoplasmic domain has been replaced by human IPS1 or a variant thereof capable of activating the STING pathway. In preferred embodiments, the viral vector is a lentiviral vector. In some embodiments, the vector includes a functional lentiviral integrase protein and can thereby integrate into the genome of the cells it is transducing.

The antigen may be a tumor antigen, viral antigen, or microbial antigen. Multiple antigens or selected epitopes of one or more antigens can be encoded by the vector. In certain embodiments, at least one antigen is selected from the group consisting of NY-ESO-1, mesothelin, PSA, MART-1, MART-2, Gp100, tyrosinase, p53, ras, MUC1, SAP-1, survivin, CEA, Ep-CAM, Her2, BRCA1/2, gag, reverse transcriptase, tat, circumsporozoite protein, HCV nonstructural proteins, hemaglutinins, and combinations thereof. In certain embodiments, the vector further encodes at least one immune checkpoint inhibitor molecule, such as an anti-CTLA-4 molecule, a PD-1 blocker, a PDL1 blocker, or a combination thereof.

In certain embodiments, the viral vector includes more than one nucleic acid sequence. In some embodiments, the first nucleic acid sequence encodes one or more marker proteins, antigens, epitopes, or combinations thereof the second nucleic acid sequence encodes a fusion protein including the transmembrane portion of the latent membrane protein 1 (LMP1) of Epstein Barr virus in which the intra-cytoplasmic domain has been replaced by human IPS1 or a variant thereof capable of activating the STING pathway; and optionally a third nucleic acid sequence encodes one or more immune checkpoint inhibitor molecules ("anti-checkpoints"). Preferably, the first and second, as well as the second and third, nucleic acid sequences are separated by a nucleic acid sequence encoding an internal ribosome entry site (IRES). The first and second, as well as the second and third nucleic acid sequences can be separated by a nucleic acid sequence encoding a self-cleaving peptide (for example, 2A peptide). The first and second, as well as the second and third nucleic acid sequences can be separated by a nucleic acid sequence encoding either a self-cleaving peptide (for example 2A peptide) or an internal ribosome entry site (IRES).

Another aspect of the technology is an immunotherapeutic formulation for preventing or treating a disease or condition in a subject including the viral vector. In preferred embodiments, the disease or condition is cancer or infection.

Another aspect of the technology is method of inducing an immune response against cancer or infection in a subject, the method including administering the viral vector or the immunotherapeutic formulation to a subject in need thereof. In some embodiments, administering the viral vector to the subject vaccinates the subject against cancer or infection.

In some embodiments, the cancer is selected from the group consisting of: melanoma, glioma, prostate cancer, ovarian cancer, breast cancer, cervical cancer, colorectal cancer, kidney cancer, lung cancer, lymphoma, sarcomas and pancreatic cancer. In some embodiments, the cancer harbors a tumor antigen listed above. In some embodiments, the cancer is sensitive to an anticheckpoint. In some embodiments, the infectious disease is selected from the group consisting of: HIV/AIDS, hepatitis C, HPV, pneumonia, influenza, malaria, leishmaniasis, tuberculosis, Hansen's disease, rabies, dengue, Zika virus infection, Ebola virus infection, and schistosomiasis. In some embodiments, the infectious agent harbors a viral or microbial antigen listed above. In some embodiments, the infectious disease is sensitive to an anticheckpoint.

The present technology also can be summarized with the following listing of embodiments.

1. A viral vector comprising a first nucleic acid sequence encoding an antigen or an antigenic epitope and a second nucleic acid sequence encoding a fusion protein including the transmembrane portion of the latent membrane protein 1 (LMP1) of Epstein Barr virus in which the intracytoplasmic domain has been replaced by human IPS1 or a variant thereof capable of activating the STING pathway, the encoded sequences of the vector being codon optimized for human expression.
2. The viral vector of embodiment 1, wherein the vector is a lentiviral vector.
3. The viral vector of embodiment 1 or 2, wherein the first nucleic acid sequence encodes a fusion protein comprising two or more antigens or two or more antigenic epitopes.
4. The viral vector of any of the preceding embodiments, wherein the second nucleic acid sequence comprises a sequence selected from the group consisting of SEQ ID NO.1, SEQ ID NO:3, SEQ ID NO:5, and SEQ ID NO:7.
5. The viral vector of any of the preceding embodiments, wherein the vector further comprises a third nucleic acid sequence encoding a soluble immune checkpoint inhibitor molecule or a soluble immune modulator molecule.
6. The viral vector of embodiment 5, wherein the soluble immune checkpoint inhibitor molecule or the soluble immune modulator molecule is selected from the group consisting of CTLA-4, PD-1, PDL-1, LAG-3, TIM 3, B7-H3, ICOS, IDO, 4-1BB, CD47, B7-H4, OX-40, TIGIT, CD160 and combinations thereof.
7. The viral vector of any of the preceding embodiments, wherein the vector further comprises a functional lentiviral integrase protein, wherein the vector is self-inactivating.
8. The viral vector of any of the preceding embodiments, wherein the antigen is selected from the group consisting of NY-ESO-1, mesothelin, PSA, MART-1, MART-2, Gp100, tyrosinase, p53, ras, MUC1, SAP-1, survivin, CEA, Ep-CAM, Her2, BRCA1/2, gag, reverse transcriptase, tat, circumsporozoite protein, HCV nonstructural proteins, hemaglutinins, and combinations thereof.
9. An immunotherapeutic formulation for preventing or treating cancer or infection in a subject, the formulation comprising the viral vector of any of embodiments 1-8.
10. A method of inducing or enhancing an immune response against a cancer or an infectious disease in a subject, the method comprising administering the viral vector of any of embodiments 1-8 or the immunotherapeutic formulation of embodiment 9 to a subject in need thereof, whereby an immune response against said cancer or infectious disease is induced or enhanced in the subject.
11. The method of embodiment 10, whereby an immune response is induced or enhanced against a cancer, and the cancer is selected from the group consisting of: melanoma, glioma, prostate cancer, breast cancer, cervical cancer, colorectal cancer, kidney cancer, lung cancer, lymphoma and pancreatic cancer.
12. The method of embodiment 10, whereby an immune response is induced or enhanced against an infectious disease, and the infectious disease is selected from the group consisting of: HIV/AIDS, hepatitis C, HPV, pneumonia, influenza, malaria, leishmaniosis, tuberculosis, Hansen's disease, rabies, dengue, Zika, Ebola, and schistosomiasis.

BRIEF DESCRIPTION OF THE DRAWINGS

FIG. 6 shows a schematic representation of the secondary structure of an LPM1-IPS1 fusion protein with IPS1 transmembrane domain removed.

FIG. 7 shows the structure of LPM1-reversed IPS1 fusion protein, with IPS transmembrane domain removed, and the caspase recruitment domain (CARD) and proline-rich (PR) domains in an inverted orientation.

FIG. 8A shows the lentivector used as controls, in which the transgenes are under the control of the human ubiquitin promoter. The transgenes are a) the GFP reporter gene, b) the transmembrane domain of the LMP1 protein, c) the GFP reporter gene and the transmembrane domain of LMP1 separated by an IRES sequence, and d) the LMP1 transmembrane domain in fusion with the full length human IPS1. FIG. 8B shows the lentivector used to evaluated various adjuvants, in which the transgenes are under the control of the human ubiquitin promoter. The transgenes are a) the GFP reporter gene separated by an IRES from the LMP1 transmembrane domain in fusion with the full length human IPS1 protein, b) the GFP reporter gene separated by an IRES from the LMP1 transmembrane domain in fusion with the human IPS1 protein with a deleted transmembrane domain, c) the GFP reporter gene separated by an IRES from the LMP1 transmembrane domain in fusion with the human IPS1 protein from which the transmembrane and proline-rich domains have been deleted and d) the GFP reporter gene separated by an IRES from the LMP1 transmembrane domain in fusion with the human IPS1 protein from which the transmembrane domain has been deleted and the CARD and Pro domains have been reversed, FIG. 8C shows the same constructs than FIG. 8B in which the adjuvant sequence is followed by an IRES and an anticheckpoint soluble molecule or soluble immune modulator molecule.

FIG. 9A shows GFP transgene expression in human dendritic cells 96 h post-transduction with the lentiviral constructs. FIG. 9B shows GFP transgene expression in human macrophages 96 h post-transduction with the lentiviral constructs.

FIG. 10A shows the panel of upregulated cytokines in human dendritic cells 96 h post-transduction with the lentiviral constructs. FIG. 10B shows the panel of upregulated markers in human GFP-positive-dendritic cells 96 h post-transduction with the lentiviral constructs (expression normalized to GFP). FIG. 10C shows the panel of upregulated cytokines in human macrophages 96 h post-transduction with the lentiviral constructs. FIG. 10D shows the panel of upregulated markers in GFP-positive-human macrophages 96 h post-transduction with the lentiviral constructs (expression normalized to GFP).

DETAILED DESCRIPTION

Figure 1:
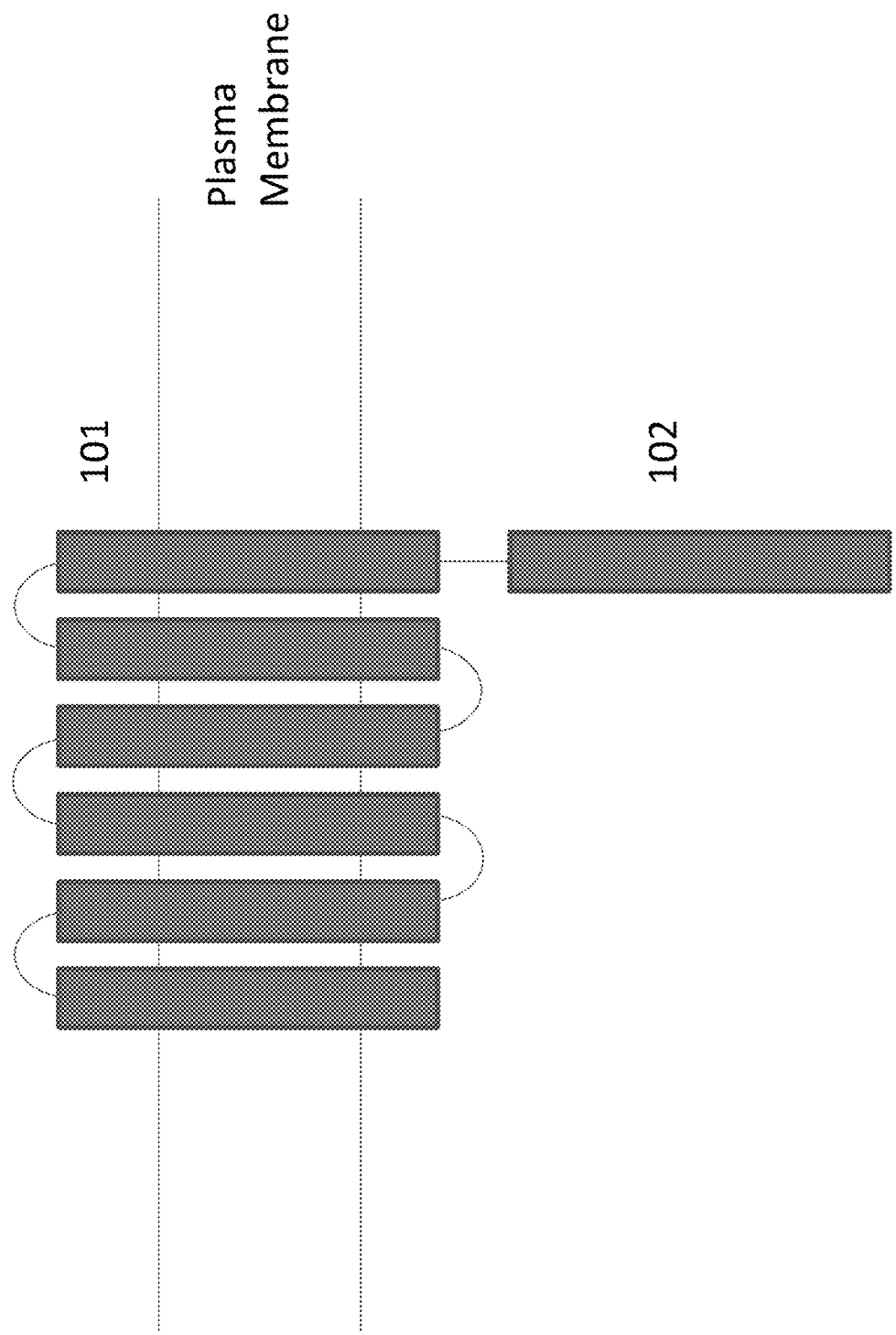
FIG. 1 shows a schematic representation of the secondary structure of LMP1 protein.
Figure 2:
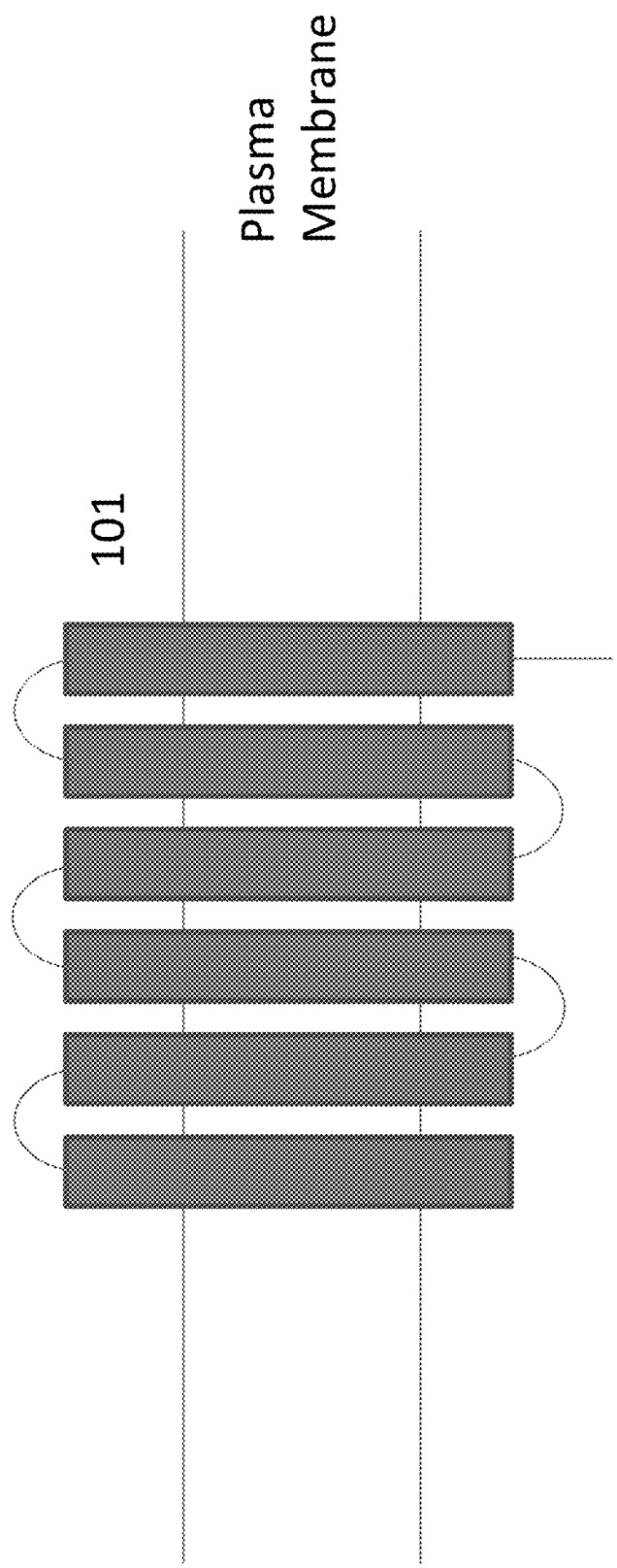
FIG. 2 shows a schematic representation of the secondary structure of a truncated LMP1 protein, with the intracytoplasmic signaling domain removed.
Figure 3A:
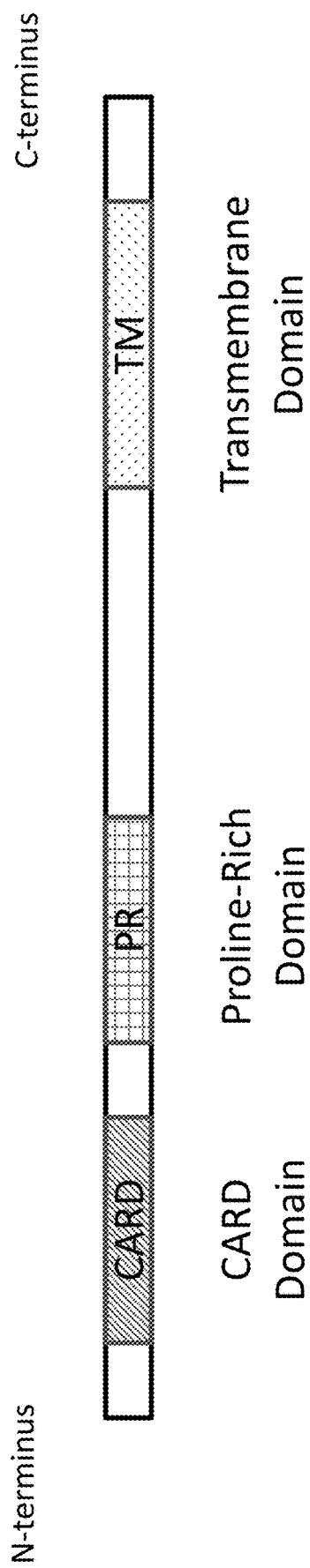
FIG. 3A shows a schematic representation of the IPS1 protein.
Figure 3B:
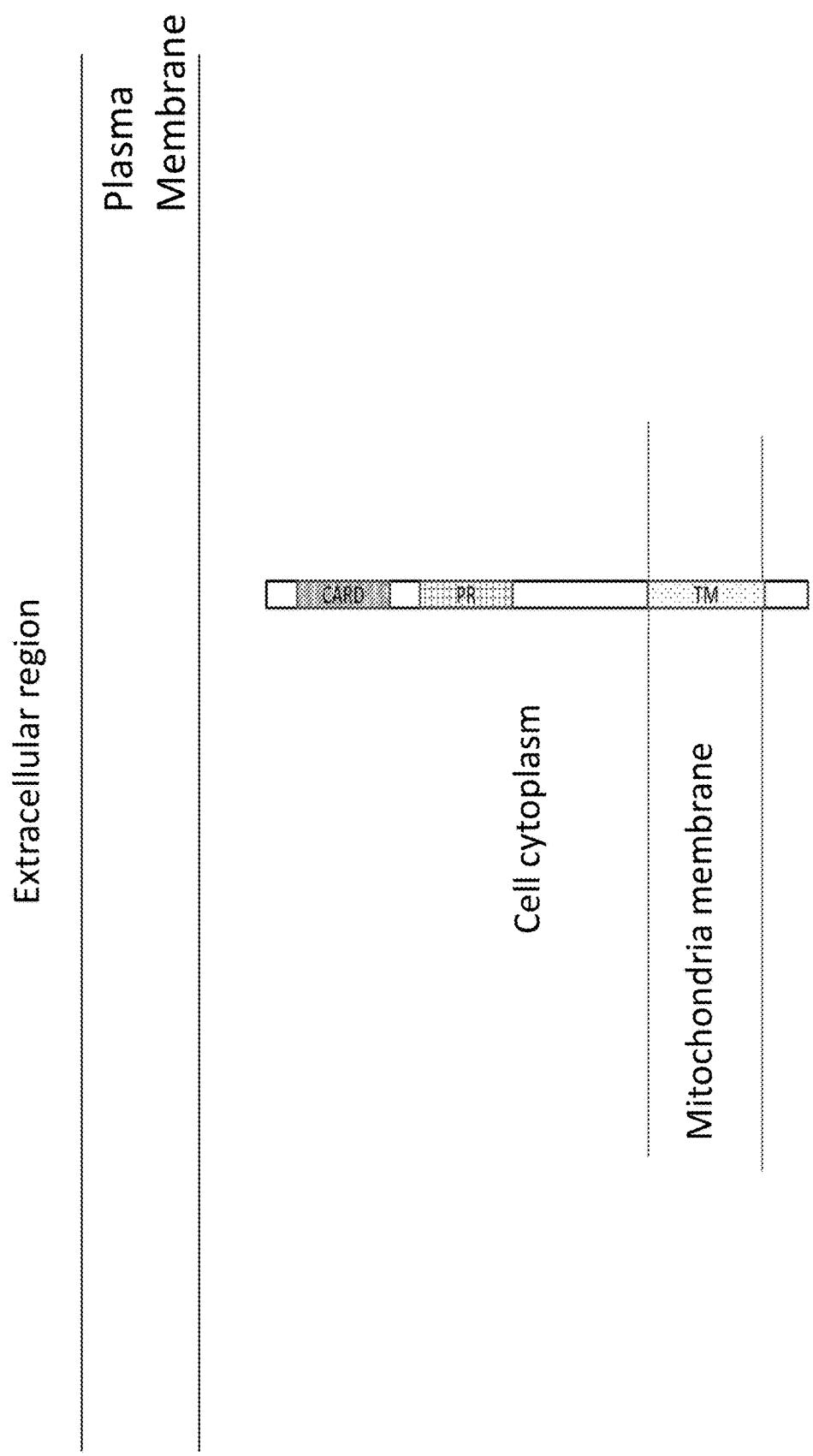
FIG. 3B shows its orientation in the mitochondrial membrane.
Figure 4:
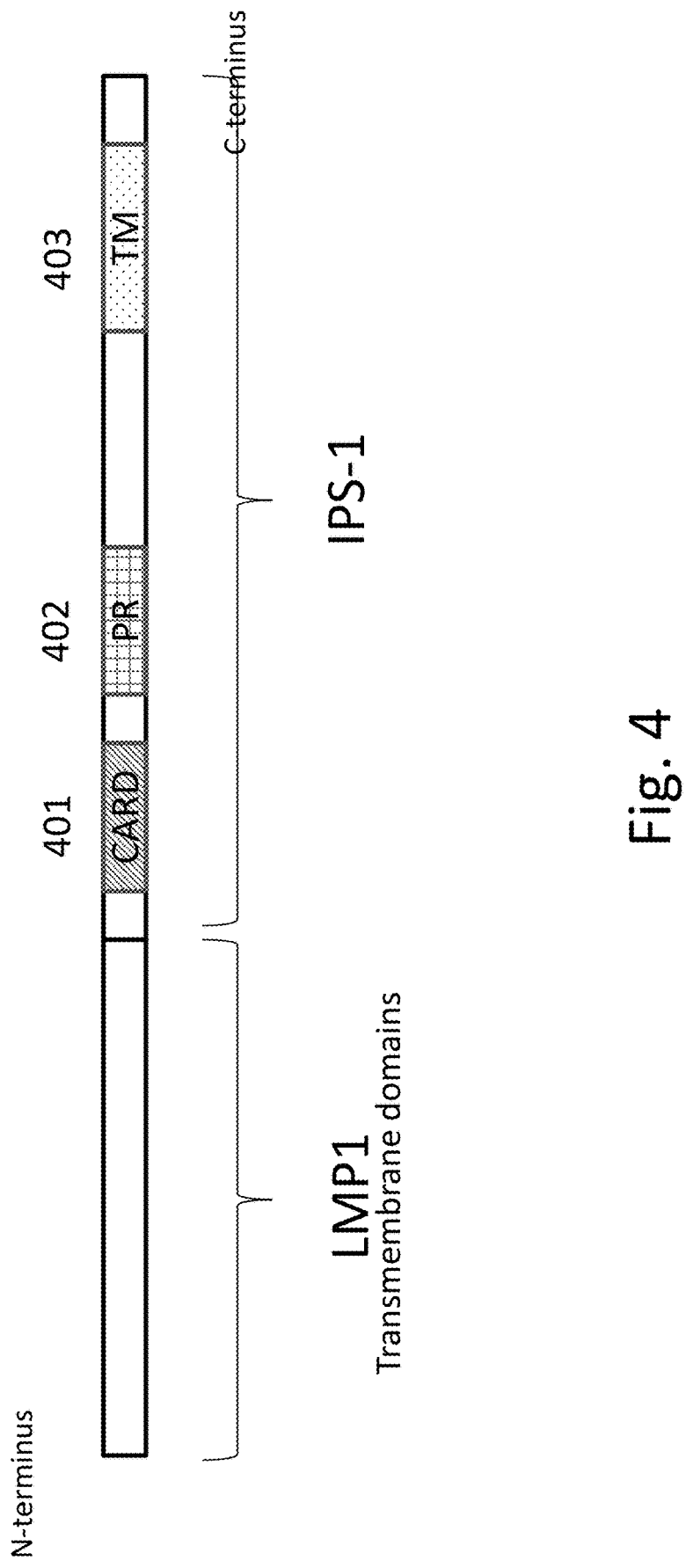
FIG. 4 shows a schematic representation of an LPM1-IPS1 fusion protein.
Figure 5:
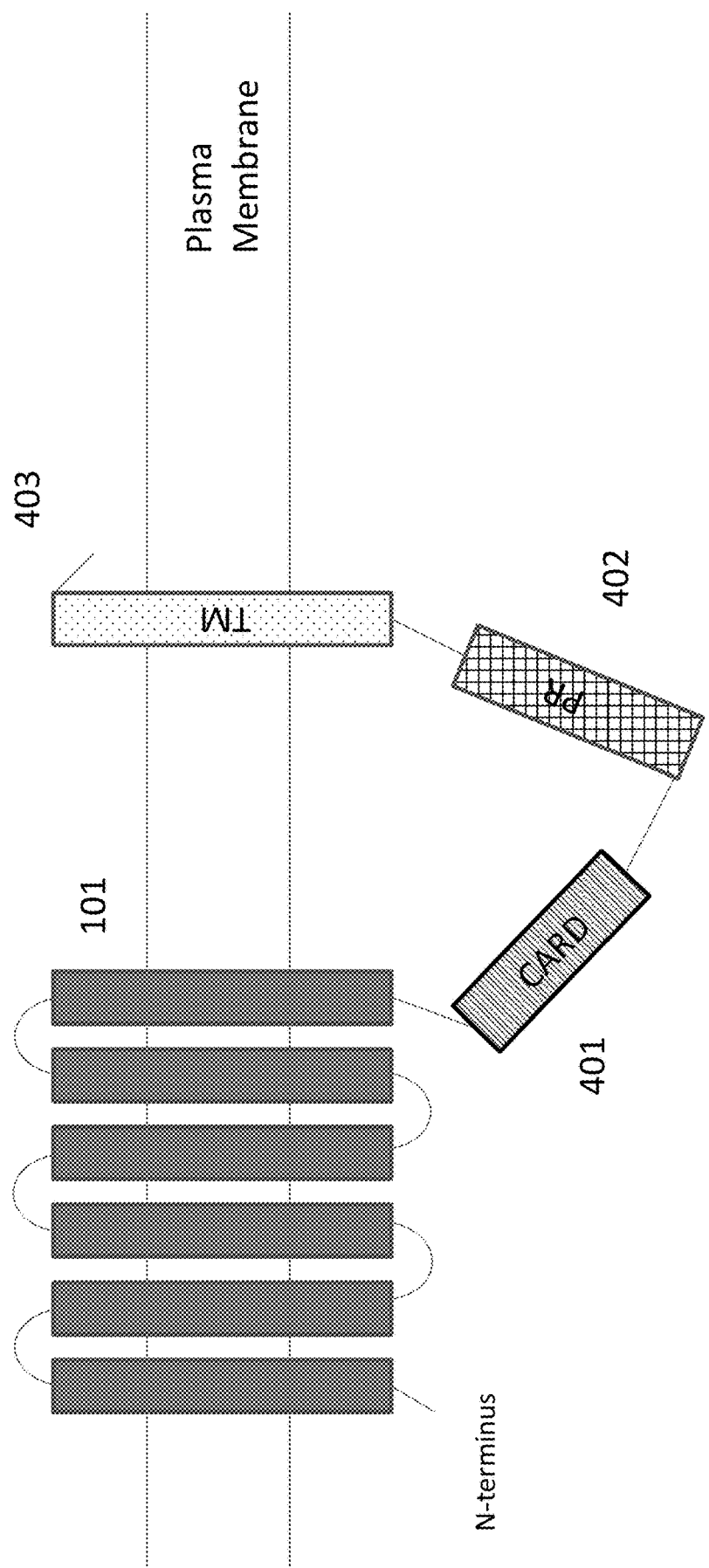
FIG. 5 shows a schematic representation of the secondary structure of an LPM1-IPS1 fusion protein as it should be produced when expressed in the order described in WO 2014/039961.

The present technology provides viral vector constructs for the expression of genetic adjuvants for use in immunotherapeutic products and methods of using the vectors. The vector constructs can improve the quality and intensity of an immune response, such as those directed against cancer or infections, being especially suited to induce and/or enhance cell-mediated immune responses.

The present technology describes the use of a single vector construct encompassing an antigenic cassette and a genetic adjuvant. When compared to concomitant injections of two vectors (one coding for the antigen and one coding for the adjuvant), the use of a single product will simplify the development (including industrial, regulatory and clinical aspects) and enhance the efficacy and safety of the treatment. With this unique construct, the cells expressing the antigenic cassette will constitutively benefit from the expression of the adjuvant improving the intensity and the quality of the triggered immune response. The transduced cells will be rapidly eliminated by the said immune response which reduces the risk of any long term and non-desired expression of the genetic sequences which could raise questions or concerns by regulatory agencies. In addition, the production and injection of only one vector will be more cost efficient when compared to the injection of two distinct vectors.

The present technology comprises one or more nucleic acid sequences that encode an EBV LMP1 protein in which the intra-cytoplasmic domain has been replaced by human IPS1 or a variant thereof capable of activating the STING pathway and one or more antigens. In a typical embodiment, the technology provides activation of immune responses by an aggregation of two or more LMP1 proteins in the cell membrane and/or aggregation of two or more IPS1 intra-cytoplasmic signaling domains. After direct injection, introduction of the nucleic acid sequences and consequent protein expression can occur in any type of cell, but preferably occurs in immune cells. This technology can be used for traditional prophylactic or therapeutic vaccines against cancer and infectious diseases, as well as cell-based therapies such as dendritic cell therapy. In the experiments described herein, the viral vectors are expected to markedly enhance immune responses and protection from or treatment of infection and cancer.

"Vector" refers to a molecule containing a nucleic acid sequence coding for at least part of a gene product capable of being transcribed. In some cases, nucleic acid molecules are then translated into a protein, polypeptide, or peptide. In other cases, these sequences are not translated, such as in the production of antisense molecules, ribozymes or aptamers. Vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

A "construct" can be any type of engineered nucleic acid coding for gene products in which part or all of the nucleic acid encoding sequence is capable of being transcribed. The transcript generally is translated into a protein, but it need not be. In certain embodiments, expression includes both transcription of a gene and translation of mRNA into a gene product. In other embodiments, expression only includes transcription of the nucleic acid encoding genes of interest.

As used herein, "vaccine" includes all prophylactic and therapeutic vaccines.

An "adjuvant" can be any molecule or composition that activates or enhances an immune response to an antigen. An adjuvant may enhance the efficacy of a vaccine by helping to modify the immune response to particular types of immune system cells. An adjuvant may be an immunostimulant that triggers activation of antigen-presenting cells such as dendritic cells, macrophages, and B cells. Adjuvants are also understood to provide a "danger" signal indicating that the immune system should go into a state of alert. Adjuvants may act by facilitating antigen presentation by antigen-presenting cells, by activating macrophages and lymphocytes and/or by supporting the production of cytokines. Without an adjuvant, immune responses may either fail to progress or may be diverted into ineffective immunity or tolerance. Adjuvants are often needed for effective preventative or therapeutic vaccines, or for inducing an anti-tumor immune response. A "genetic adjuvant" is an adjuvant that is provided in the form of a nucleic acid, which is expressed by target cells to produce a molecule that functions as an adjuvant.

An antigen-presenting cell (APC) is any of a variety of cells capable of displaying, acquiring, or presenting at least one antigen or antigenic fragment on (or at) its cell surface. In general, the term "antigen-presenting cell" can refer to any cell that accomplishes the goal of the technology by aiding the enhancement of an immune response (i.e., from the T-cell or B-cell arms of the immune system) against an antigen or antigenic composition. Such cells can be defined by those of skill in the art, using methods disclosed herein and in the art. As is understood by one of ordinary skill in the art, and used herein certain embodiments, a cell that displays or presents an antigen normally or preferentially with a class II major histocompatibility molecule or complex to an immune cell is an "antigen-presenting cell." In certain aspects, a cell (e.g., an APC) may be fused with another cell, such as a recombinant cell or a tumor cell that expresses the desired antigen. Methods for preparing a fission of two or more cells are well known in the art. In some cases, the immune cell to which an antigen-presenting cell displays or presents an antigen is a CD4+ T or a CD8+ T cell. Additional molecules expressed on the APC or other immune cells may aid or improve the enhancement of an immune response. Secreted or soluble molecules, such as for example, cytokines and adjuvants, may also aid or enhance the immune response against an antigen. A dendritic cell (DC) is an antigen-presenting cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. The DC has a characteristic morphology with thin sheets (lamellipodia) extending in multiple directions away from the dendritic cell body. Typically, dendritic cells express high levels of major histocompatibility complex (MEW) and costimulatory (e.g., B7-1 and B7-2) molecules. Dendritic cells can induce antigen specific differentiation of T cells in vitro, and are able to initiate primary T cell responses in vitro and in vivo.

By the phrase "immune response" is meant induction of antibody and/or immune cell-mediated responses specific against an antigen or antigens or allergen(s) or drug or biologic. The induction of an immune response depends on many factors, including the immunogenic constitution of the challenged organism, the chemical composition and configuration of the antigen or allergen or drug or biologic, and the manner and period of administration of the antigen or allergen or drug or biologic. An immune response has many facets, some of which are exhibited by the cells of the immune system (e.g., B-lymphocytes, T-lymphocytes, macrophages, and plasma cells). Immune system cells may participate in the immune response through interaction with an antigen or allergen or other cells of the immune system, the release of cytokines and reactivity to those cytokines. Immune responses are generally divided into two main categories—humoral and cell-mediated. The humoral component of the immune response includes production of antibodies specific for an antigen or allergen or drug or biologic. The cell-mediated component includes the generation of delayed-type hypersensitivity and cytotoxic effector cells against the antigen or allergen.

Activation or stimulation of the immune system may be mediated by the activation of immune effector cells, such as lymphocytes, macrophages, dendritic cells, natural killer cells (NK cells) and cytotoxic T lymphocytes (CTL). It can be mediated by activation and maturation of antigen presenting cells, such as dendritic cells. It can be mediated by the blockade of inhibitory pathways, such as by inhibiting immune checkpoint inhibitors.

By the term "LMP1 gene," is meant a native Epstein Barr virus LMP1-encoding nucleic acid sequence, e.g., the native Epstein Barr virus LMP1 gene; a nucleic acid having sequences from which a LMP1 cDNA can be transcribed; and/or allelic variants and homologs of the foregoing. An exemplary nucleic acid sequence of LMP1 is GenBank Accession No. M58153.1. The term encompasses double-stranded DNA, single-stranded DNA, and RNA.

By the term "LMP1 protein," is meant an expression product of a LMP1 gene or a protein that shares at least 65% (but preferably 75, 80, 85, 90, 95, 96, 97, 98, or 99%) amino acid sequence identity with the foregoing and displays a functional activity of a native LMP1 protein. A "functional activity" of a protein is any activity associated with the physiological function of the protein. LMP1 consists of an N-terminal transmembrane region linked to a C-terminal cell signaling region that is analogous to the CD40 receptor on immune cells. In addition to anchoring LMP1 into the membrane, the N-terminus of LMP1 self-aggregates and leads to clustering of LMP1 or any protein linked to the LMP1 N-terminal domain. The transmembrane (aggregation) domain of LMP1 protein is amino acids 1-190 of the amino acid sequence set forth in GenBank Accession No. AAA66330.1.

Latent membrane protein-1 (LMP1) is a gene in the Epstein-Barr Virus (EBV). Its N-terminus is composed of 6 contiguous transmembrane domains that anchor the protein into the membrane. FIG. 1 shows the structure of LMP1 protein showing a transmembrane domain 101 and an intra-cytoplasmic signaling domain 102. LMP1 needs no ligand or antibody to initiate signaling through its cytoplasmic domain since its N-terminal transmembrane domain spontaneously forms clusters in the cell membrane and thereby clusters the intracytoplasmic domain(s) that are connected to it via peptide bonds as a single polypeptide chain. In this sense, LMP1 is said to be "constitutively activated." Likewise, fusion proteins that link the N-terminal transmembrane domain to signaling domain(s) that require clustering in order to function can also be said to be "constitutively activated" and no longer need the ligand from the receptor from which they are taken.

Interferon Promoter Stimulator-1 (IPS1, also called MAVS, VISA, or Cardif) is a transmembrane mitochondrial protein related to the STING pathway ("stimulator of interferon genes"; also known as TMEM173, MPYS, MITA and ERIS), which is important for the innate response to pathogen-derived nucleic acids in the cytosol. IPS1 contains a C-terminal transmembrane domain that anchors the protein to the outer membrane of mitochondria where it forms aggregates (i.e., multimers) once activated. IPS1 also is present in peroxisomes and mitochondrial-associated membranes. IPS1 also contains a caspase recruitment domain (CARD), indispensable for downstream protein-protein interactions, and three TRAF-interacting motifs (TIM), two included in the N-terminal proline-rich region and the third located in the C-terminal region. Membrane localization of IPS1 may be important for its activity, since removal of the transmembrane domain inhibits the IPS1-mediated antiviral response. IPS1 functions as an adaptor protein for pathogen recognition receptors, such as retinoic-acid-inducible gene-I (RIG-I)-like receptors (RLR), which patrol the cytoplasm for the presence of viral RNA. When double stranded RNA binds to an RLR, they form a complex with IPS1 via their CARD domains, leading to IPS1 multimerization and activation. Activated IPS1 complexes then recruit the IKK and TBK1/IKKi complexes, thereby triggering a signaling cascade that results in the activation of transcription factors NF-kappaB and IRF3. NF-kappaB and IRF3 bind to and activate the interferon promoter, resulting in a potent cell-mediated immune response via production of type 1 interferons. RIG-1 activation also activates the STING pathway, further enhancing cell-mediated immune responses against viruses. In the present technology, fusion of IPS1 with the LMP1 N-terminal domain promotes LMP1-IPS1 clustering and activation that mimics activation by dsRNA.

Viral vectors of the present technology encode one or more nucleic acids sequences capable of activating or enhancing an immune response in a subject. The nucleic acids encode a latent membrane protein 1 (LMP1) of the Epstein Barr virus in which the intra-cytoplasmic domain has been replaced by human IPS1 or a variant thereof capable of activating the STING pathway. The LMP1 DNA sequence has been codon optimized for human expression. Expression of the LMP1-IPS1 fusion protein provides activation of immune responses by aggregation (i.e., multimerization) of two or more LMP1 proteins.

The viral vector can be any type of suitable vector, such as an expression vector or a plasmid. In preferred embodiments, the vector is a lentiviral vector. Lentiviral vectors are modified lentiviruses, derived, for example, from human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV). The modified lentiviral vectors have reduced pathogenicity. The vectors may also be modified to introduce beneficial therapeutic effects. Lentiviral vectors themselves are not toxic and, unlike other retroviruses, lentiviruses are capable of transducing non-dividing cells, in particular dendritic cells, allowing antigen presentation through the endogenous pathway.

Lentiviral vectors can include an RNA or DNA molecule. In some embodiments, the lentiviral vector is a recombinant DNA molecule, such as a plasmid. In some embodiments, the lentiviral vector includes a recombinant DNA molecule as well as associated viral proteins to form a particle. Lentiviral vector particles may contain single or double stranded nucleic acid molecules.

In preferred embodiments, the lentiviral vectors have the capacity for integration into the genome of the cells being transduced. In preferred embodiments, they contain a functional integrase protein. Non-integrating vector particles display genetic mutations that hinder the lentiviral vector particles capacity for integrating into the host genome. The term "transfection" and "transduction" refer to the process by which an exogenous DNA sequence is introduced into a eukaryotic host cell. Transfection is the non-viral delivery of nucleic acids (either DNA or RNA) and can be achieved by any one of a number of means including electroporation, microinjection, gene gun delivery, retroviral infection, lipofection, polymer-mediated delivery, and the like. Transduction refers to delivery of nucleic acids by a virus or viral vector where the nucleic acids are typical DNA for a DNA virus and RNA for an RNA virus.

In some embodiments, the lentiviral vector is self-inactivating and does not contain an enhancer. Self-inactivating lentiviral vectors have modifications in the U3 ($\Delta$U3) region of the 3' LTR that render the vectors unable to replicate in the host cell. The U3 region encodes binding sites that are essential for basal promoter activity and viral replication, and elimination of these binding sites results in virtually complete inactivation of viral replication.

Myriad factors influence the efficacy of viral vectors, even after successful transduction and, optionally, integration into the host genome: gene expression and translation; protein folding, transport and turnover; and cell-to-cell interactions, to name a few. These factors depend, among other things, on the nucleic acid sequences encoded by the vector. Preferred DNA sequences for conducting the present technology include modifications of native sequences aimed at increasing viral vector efficacy and efficiency. These modifications include: codon optimization for human use; removal of the first methionine of IPS1 sequence in the fusion protein; removal of IPS1 transmembrane and proline-rich domains, as well as use of a reversed IPS1 sequence. These modifications may impact the rates of transcription and/or translation, as well as impact protein location in the cell and protein activity.

The viral vectors of the present technology encode one or more antigens. The term "antigen" as used herein refers to a molecule that provokes an immune response. This immune response may involve either antibody production, or the activation of specific immunologically-competent cells, or both. An antigen can be derived from organisms, subunits of proteins/antigens, killed or inactivated whole cells or lysates. Therefore, a skilled artisan realizes that any macromolecule, including virtually all proteins or peptides, can serve as antigens. Furthermore, antigens can be derived from recombinant or genomic DNA. A skilled artisan realizes that any DNA, which contains nucleotide sequences or partial nucleotide sequences of a pathogenic genome or a gene or a fragment of a gene for a protein that elicits an immune response results in synthesis of an antigen. Furthermore, one skilled in the art realizes that the present technology is not limited to the use of the entire nucleic acid sequence of a gene or genome. The present technology includes, but is not limited to, the use of partial nucleic acid sequences of more than one gene or genome whose nucleic acid sequences are arranged in various combinations to elicit the desired immune response.

The antigen may be any antigen for which an enhanced immune response is desirable. Such antigens include, but are not limited to, antigens from pathogens that cause infectious disease for which a protective immune response may be elicited. For example, antigens from HIV include the proteins gag, env, pol, tat, rev, nef, reverse transcriptase, and other HIV components. The E6 and E7 proteins from human papilloma virus are also suitable antigens. Furthermore, the EBNA1 antigen from herpes simplex virus is suitable. Other viral antigens for use in the technology are hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin, neuraminidase, nucleoprotein, M2, and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS 1, NS 1-NS2A, 80% E, and other Japanese encephalitis viral antigen components; rabies viral antigens such as rabies glycoprotein, rabies nucleoprotein and other rabies viral antigen components; West Nile virus prM and E proteins; and Ebola envelope protein. See Fundamental Virology, Second Edition, eds. Knipe, D. M. and, Howley P. M. (Lippincott Williams & Wilkins, New York, 2001) for additional examples of viral antigens. In addition, bacterial antigens are also disclosed. Bacterial antigens which can be used in the compositions and methods of the technology include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; Staphylococcal bacterial antigens such as IsdA, IsdB, SdrD, and SdrE; gram-negative bacilli bacterial antigens such as lipopolysaccharides, flagellin, and other gram-negative bacterial antigen components; *Mycobacterium tuberculosis* bacterial antigens such as mycolic acid, heat shock protein 65 (HSP65), the 30 kDa major secreted protein, antigen 85A, ESAT-6, and other mycobacterial antigen components; Helicobacter pylori bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other haemophilus influenza bacterial antigen components; anthrax bacterial antigens such as anthrax protective antigen, anthrax lethal factor, and other anthrax bacterial antigen components; the F 1 and V proteins from Yersinia pestis; rickettsiae bacterial antigens such as romps and other rickettsiae bacterial antigen components. Also included with the bacterial antigens described herein are any other bacterial, mycobacterial, mycoplasmal, rickettsial, or chlamydial antigens. Examples of protozoa and other parasitic antigens include, but are not limited to, plasmodium falciparum antigens such as merozoite surface antigens, sporozoite surface antigens, circumsporozoite antigens, gametocyte/gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components. Examples of fungal antigens include, but are not limited to, antigens from *Candida* species, *Aspergillus* species, *Blastomyces* species, *Histoplasma* species, *Coccidiodomycosis* species, *Malassezia furfur* and other species, *Exophiala werneckii* and other species, *Piedraia hortai* and other species, *Trichosporum beigelii* and other species, *Microsporum* species, *Trichophyton* species, *Epidermophyton* species, *Sporothrix schenckii* and other species, *Fonsecaea pedrosoi* and other species, *Wangiella dermatitidis* and other species, *Pseudallescheria boydii* and other species, *Madurella grisea* and other species, *Rhizopus* species, *Absidia* species, and *Mucor* species. Examples of prion disease antigens include PrP, beta-amyloid, and other prion-associated proteins.

In addition to the infectious and parasitic agents mentioned above, another area for desirable enhanced immunogenicity to a non-infectious agent is inflammatory and autoimmune diseases, neurodegenerative diseases and in the area of proliferative diseases, including but not limited to cancer, in which cells expressing cancer antigens are desirably eliminated from the body. Tumor antigens which can be used in the compositions and methods of the technology include, but are not limited to, prostate specific antigen (PSA), breast, ovarian, testicular, melanoma, telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells. It is contemplated by the technology that antigens from any type of tumor cell can be used in the compositions and methods described herein. The antigen may be a cancer cell, or immunogenic materials isolated from a cancer cell, such as membrane proteins. Included are survivin and telomerase universal antigens and the MAGE family of cancer testis antigens. Antigens which have been shown to be involved in autoimmunity and could be used in the methods of the present technology to induce tolerance include, but are not limited to, myelin basic protein, myelin oligodendrocyte glycoprotein and proteolipid protein of multiple sclerosis and CII collagen protein of rheumatoid arthritis.

The antigen may be a portion of an infectious agent such as HIV-1, EBV, HBV, influenza virus, SARS virus, poxviruses, malaria, or HSV, by way of non-limiting examples, for which vaccines that mobilize strong T-cell mediated immunity (via dendritic cells) are needed.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The term "tumor" denotes at least one cell or cell mass in the form of a tissue neoformation, in particular in the form of a spontaneous, autonomous and irreversible excess growth, which is more or less disinhibited, of endogenous tissue, which growth is as a rule associated with the more or less pronounced loss of specific cell and tissue functions. This cell or cell mass is not effectively inhibited, in regard to its growth, by itself or by the regulatory mechanisms of the host organism, e.g. melanoma or carcinoma. Tumor antigens not only include antigens present in or on the malignant cells themselves, but also include antigens present on the stromal supporting tissue of tumors including endothelial cells and other blood vessel components. In a related aspect, "neoplastic" refers to abnormal new growth and thus means the same as tumor, which may be benign or malignant. Further, such neoplasia would include cell proliferation disorders.

A lentiviral vector of the technology further comprises a nucleic acid sequence that encodes one or more adjuvants. A preferred adjuvant is the fusion protein LMP1 (delta) hIPS1, which contains LMP1 from Epstein Barr virus, without the intracytoplasmic region. in fusion with the full length human IPS1. In the fusion protein, the first amino acid (methionine) of human IPS1 was removed. The fusion protein is codon optimized for human use. The DNA and encoded amino acid sequences of this fusion protein are shown below:

```
DNA sequence
                                                             (SEQ ID NO: 1)
ATGGATCTGGATCTCGAAAGAGGACCTCCTGGACCTAGACGGCCTCCTAGAGGACCACCTCTGAGCAGCTCTATT

GGACTGGCCCTGCTGCTGCTTCTGCTGGCTCTGCTGTTCTGGCTGTACATCATCATGAGCAACTGGACCGGCGGA

GCACTGCTGGTGCTGTATGCCTTTGCTCTGATGCTGGTCATCATCATCCTGATCATCTTCATCTTCCGGCGGGAC

CTGCTGTGTCCTCTGGGAGCACTTTGTCTGTTGCTGCTGATGATCACCCTCCTGCTGATCGCCCTGTGGAACCTG
```

-continued

```
CATGGACAGGCCCTGTATCTGGGCATCGTGCTGTTCATCTTCGGCTGCCTGCTGGTTCTCGGCCTGTGGATCTAC
CTGCTGGAAATCCTTTGGAGACTGGGCGCCACCATCTGGCAGCTGCTGGCCTTTTTCCTGGCCTTCTTTCTGGAT
ATCATCCTCCTCATCATTGCCCTGTACCTGCAGCAGAACTGGTGGACCCTGCTGGTGGATCTGCTTTGGCTGCTG
CTCTTTCTGGCCATCCTGATTTGGATGTACTACCACGGCCAGCGGCCTTTCGCCGAGGACAAGACCTACAAGTAC
ATCTGCCGGAACTTCAGCAACTTCTGCAACGTGGACGTGGTGGAAATTCTGCCCTACCTGCCTTGCCTGACCGCC
AGAGATCAGGACAGACTGAGAGCCACATGTACCCTGAGCGGCAACAGAGACACACTGTGGCACCTGTTCAACACC
CTGCAGAGAAGGCCTGGCTGGGTCGAGTACTTTATCGCCGCTCTGAGAGGCTGCGAGCTGGTCGATCTGGCTGAT
GAAGTGGCCAGCGTGTACCAGAGCTACCAGCCTAGAACCAGCGACCGGCCTCCTGATCCTCTCGAACCTCCATCT
CTGCCCGCCGAAAGACCTGGACCTCCTACACCAGCTGCCGCTCACAGCATCCCTTACAACAGCTGCAGAGAGAAA
GAACCTAGCTACCCCATGCCTGTGCAAGAGACACAGGCCCCAGAAAGCCCTGGCGAGAATAGCGAACAGGCTCTG
CAGACACTGAGCCCCAGAGCCATTCCTAGAAACCCTGATGGCGGCCCTCTGGAAAGCTCTAGTGATCTGGCCGCT
CTGTCCCCTCTGACAAGCTCTGGACACCAAGAGCAGGATACCGAGCTGGGCAGCACACATACAGCCGGCGCTACA
AGCAGCCTGACACCTTCTAGAGGCCCCGTGTCTCCCAGCGTGTCATTTCAGCCTCTGGCCAGGTCTACCCCTAGG
GCTTCTAGACTGCCTGGACCAACAGGCAGCGTGGTGTCTACCGGCACAAGCTTCAGCTCTAGCTCTCCTGGACTG
GCTAGTGCCGGTGCCGCTGAGGGAAAACAAGGCGCCGAATCTGATCAGGCCGAGCCTATCATCTGTAGCAGCGGA
GCAGAAGCCCCTGCCAATAGCCTGCCTAGCAAGGTGCCAACCACACTGATGCCCGTGAACACAGTGGCCCTGAAG
GTGCCAGCTAATCCTGCCTCCGTGTCCACCGTGCCTTCTAAGCTGCCAACCAGCTCTAAGCCACCTGGCGCCGTG
CCATCTAACGCCCTGACAAATCCTGCTCCAAGCAAGCTGCCCATCAACTCCACAAGAGCCGGCATGGTGCCCTCT
AAGGTGCCCACATCTATGGTGCTGACCAAGGTGTCCGCCAGCACCGTGCCAACAGATGGCAGCTCCAGAAACGAG
GAAACCCCTGCCGCTCCTACTCCTGCTGGCGCTACAGGCGGATCTTCTGCTTGGCTGGATAGCAGCAGCGAGAAC
AGAGGCCTGGGCAGCGAGCTTTCTAAACCTGGCGTGCTGGCTTCCCAGGTGGACAGCCCATTTTCCGGCTGCTTT
GAGGACCTGGCTATCAGCGCCTCTACAAGCCTCGGCATGGGACCTTGTCACGGCCCCGAGGAAAACGAGTACAAG
AGCGAGGGCACCTTCGGCATCCACGTGGCCGAGAATCCTAGCATCCAACTGCTGGAAGGCAACCCCGGACCTCCA
GCTGATCCAGATGGCGGACCAAGACCTCAGGCCGACAGAAAGTTCCAAGAGCGCGAGGTGCCCTGCCACAGACCT
TCTCCAGGTGCTCTGTGGCTGCAGGTTGCAGTGACAGGCGTCCTGGTGGTTACACTGCTCGTGGTCCTGTATAGA
CGGCGGCTGCACTGATGA
```

Protein sequence
(SEQ ID NO: 2)

```
MDLDLERGPPGPRRPPRGPPLSSSIGLALLLLLLALLFWLYIIMSNWTGGALLVLYAFALMLVIIILIIFIFRRD
LLCPLGALCLLLLMITLLLIALWNLHGQALYLGIVLFIFGCLLVLGLWIYLLEILWRLGATIWQLLAFFLAFFLD
IILLIIALYLQQNWWTLLVDLLWLLLFLAILIWMYYHGQRPFAEDKTYKYICRNFSNFCNVDVVEILPYLPCLTA
RDQDRLRATCTLSGNRDTLWHLENTLQRRPGWVEYFIAALRGCELVDLADEVASVYQSYQPRTSDRPPDPLEPPS
LPAERPGPPTPAAAHSIPYNSCREKEPSYPMPVQETQAPESPGENSEQALQTLSPRAIPRNPDGGPLESSSDLAA
LSPLTSSGHQEQDTELGSTHTAGATSSLTPSRGPVSPSVSFQPLARSTPRASRLPGPTGSVVSTGTSFSSSSPGL
ASAGAAEGKQGAESDQAEPTICSSGAEAPANSLPSKVPTTLMPVNTVALKVPANPASVSTVPSKLPTSSKPPGAV
PSNALTNPAPSKLPINSTRAGMVPSKVPTSMVLTKVSASTVPTDGSSRNEETPAAPTPAGATGGSSAWLDSSSEN
RGLGSELSKPGVLASQVDSPFSGCFEDLAISASTSLGMGPCHGPEENEYKSEGTFGIHVAENPSIQLLEGNPGPP
ADPDGGPRPQADRKFQEREVPCHRPSPGALWLQVAVTGVLVVTLLVVLYRRRLH
```

Another preferred adjuvant is the fusion protein LMP1 (deltaIC) hIPS1 (deltaTM), which contains LMP1 from Epstein Barr virus, without the intracytoplasmic region. in fusion with amino acids 2-439 of human IPS1, without its transmembrane region. In the fusion protein, the first amino acid (methionine) of human IPS1 was removed. The fusion protein is codon optimized for human use. The DNA and encoded amino acid sequences of this fusion protein are shown below:

```
DNA sequence
                                                         (SEQ ID NO: 3)
ATGGATCTGGATCTCGAAAGAGGACCTCCTGGACCTAGACGGCCTCCTAGAGGACCACCTCTGAGCAGCTCTATTGGACTGGC CCTGCTGCTGCTTCTGCTGGCTCTGCTGTTCTGGCTGTACATCATCATGAGCAACTGGACCGGCGGAGCACTGCTGGTGCTGT ATGCCTTTGCTCTGATGCTGGTCATCATCATCCTGATCATCTTCATCTTCCGGCGGGACCTGCTGTGTCCTCTGGGAGCACTT TGTCTGTTGCTGCTGATGATCACCCTCCTGCTGATCGCCCTGTGGAACCTGCATGGACAGGCCCTGTATCTGGGCATCGTGCT GTTCATCTTCGGCTGCCTGCTGGTTCTCGGCCTGTGGATCTACCTGCTGGAAATCCTTTGGAGACTGGGCGCCACCATCTGGC AGCTGCTGGCCTTTTTCCTGGCCTTCTTTCTGGATATCATCCTCCTCATCATTGCCCTGTACCTGCAGCAGAACTGGTGGACC CTGCTGGTGGATCTGCTTTGGCTGCTGCTCTTTCTGGCCATCCTGATTTGGATGTACTACCACGGCCAGCGGCCTTTCGCCGA GGACAAGACCTACAAGTACATCTGCCGGAACTTCAGCAACTTCTGCAACGTGGACGTGGTGGAAATTCTGCCCTACCTGCCTT GCCTGACCGCCAGAGATCAGGACAGACTGAGAGCCACATGTACCCTGAGCGGCAACAGAGACACACTGTGGCACCTGTTCAAC ACCCTGCAGAGAAGGCCTGGCTGGGTCGAGTACTTTATCGCCGCTCTGAGAGGCTGCGAGCTGGTCGATCTGGCTGATGAAGT GGCCAGCGTGTACCAGAGCTACCAGCCTAGAACCAGCGACCGGCCTCCTGATCCTCTCGAACCTCCATCTCTGCCCGCCGAAA GACCTGGACCTCCTACACCAGCTGCCGCTCACAGCATCCCTTACAACAGCTGCAGAGAAAGAACCTAGCTACCCCATGCCT GTGCAAGAGACACAGGCCCCAGAAAGCCCTGGCGAGAATAGCGAACAGGCTCTGCAGACACTGAGCCCCAGAGCCATTCCTAG AAACCCTGATGGCGGCCCTCTGGAAAGCTCTAGTGATCTGGCCGCTCTGTCCCCTCTGACAAGCTCTGGACACCAAGAGCAGG ATACCGAGCTGGGCAGCACACATACAGCCGGCGCTACAAGCAGCCTGACACCTTCTAGAGGCCCCGTGTCTCCCAGCGTGTCA TTTCAGCCTCTGGCCAGGTCTACCCCTAGGGCTTCTAGACTGCCTGGACCAACAGGCAGCGTGGTGCTACCGGCACAAGCTT CAGCTCTAGCTCTCCTGGACTGGCTAGTGCCGGTGCCGCTGAGGGAAAACAAGGCGCCGAATCTGATCAGGCCGAGCCTATCA TCTGTAGCAGCGGAGCAGAAGCCCCTGCCAATAGCCTGCCTAGCAAGGTGCCAACCACACTGATGCCCGTGAACACAGTGGCC CTGAAGGTGCCAGCTAATCCTGCCTCCGTGTCCACCGTGCCTTCTAAGCTGCCAACCAGCTCTAAGCCACCTGGCGCCGTGCC ATCTAACGCCCTGACAAATCCTGCTCCAAGCAAGCTGCCCATCAACTCCACAAGAGCCGGCATGGTGCCCTCTAAGGTGCCCA CATCTATGGTGCTGACCAAGGTGTCCGCCAGCACCGTGCCAACAGATGGCAGCTCCAGAAACGAGGAAACCCCTGCCGCTCCT ACTCCTGCTGGCGCTACAGGCGGATCTTCTGCTTGGCTGGATAGCAGCAGCGAGAACAGAGGCCTGGGCAGCGAGCTTTCTAA ACCTGGCGTGCTGGCTTCCCAGGTGGACAGCCCATTTTCCGGCTGCTTTGAGGACCTGGCTATCAGCGCCTCTACAAGCCTCG GCATGGGACCTTGTCACGGCCCCGAGGAAAACGAGTACAAGAGCGAGGGCACCTTCGGCATCCACGTGGCCGAGAATCCTAGC ATCCAACTGCTGGAAGGCAACCCCGGACCTCCAGCTGATCCAGATGGCGGACCAAGACCTCAGGCCGACAGAAAGTTCCAAGA

GCGCGAGGTGCCCTGCCACAGACCTTCTCCA

Protein sequence
                                                         (SEQ ID NO: 4)
MDLDLERGPPGPRRPPRGPPLSSSIGLALLLLLLALLFWLYIIMSNWTGGALLVLYAFALMLVIIILIIFIFRRDLLCPLGAL CLLLLMITLLLIALWNLHGQALYLGIVLFIFGCLLVLGLWIYLLEILWRLGATIWQLLAFFLAFFLDIILLIIALYLQQNWWT LLVDLLWLLLFLAILIWMYYHGQRPFAEDKTYKYICRNFSNFCNVDVVEILPYLPCLTARDQDRLRATCTLSGNRDTLWHLFN TLQRRPGWVEYFIAALRGCELVDLADEVASVYQSYQPRTSDRPPDPLEPPSLPAERPGPPTPAAAHSIPYNSCREKEPSYPMP VQETQAPESPGENSEQALQTLSPRAIPRNPDGGPLESSSDLAALSPLTSSGHQEQDTELGSTHTAGATSSLTPSRGPVSPSVS FQPLARSTPRASRLPGPTGSVVSTGTSFSSSSPGLASAGAAEGKQGAESDQAEPTICSSGAEAPANSLPSKVPTTLMPVNTVA LKVPANPASVSTVPSKLPTSSKPPGAVPSNALTNPAPSKLPINSTRAGMVPSKVPTSMVLTKVSASTVPTDGSSRNEETPAAP TPAGATGGSSAWLDSSSENRGLGSELSKPGVLASQVDSPFSGCFEDLAISASTSLGMGPCHGPEENEYKSEGTFGIHVAENPS

IQLLEGNPGPPADPDGGPRPQADRKFQEREVPCHRPSP
```

Another preferred adjuvant is the fusion protein LMP1 (deltaIC) hIPS1 (delta-TM delta-Pro), which contains LMP1 from Epstein Barr virus, without the intracytoplasmic region. in fusion with amino acids 2-93 of human IPS1 (a truncated IPS1 with the C terminal proline-rich and transmembrane domain removed). In the fusion protein, the first amino acid (methionine) of human IPS1 was removed. The fusion protein is codon optimized for human use. The DNA and encoded amino acid sequences of this fusion protein are shown below:

```
DNA sequence
                                                                    (SEQ ID NO: 5)
ATGGATCTGGATCTCGAAAGAGGACCTCCTGGACCTAGACGGCCTCCTAGAGGACCACCTCTGAGCAGCTCTATTGGACTGGC CCTGCTGCTGCTTCTGCTGGCTCTGCTGTTCTGGCTGTACATCATCATGAGCAACTGGACCGGCGGAGCACTGCTGGTGCTGT ATGCCTTTGCTCTGATGCTGGTCATCATCATCCTGATCATCTTCATCTTCCGGCGGGACCTGCTGTGTCCTCTGGGAGCACTT TGTCTGTTGCTGCTGATGATCACCCTCCTGCTGATCGCCCTGTGGAACCTGCATGGACAGGCCCTGTATCTGGGCATCGTGCT GTTCATCTTCGGCTGCCTGCTGGTTCTCGGCCTGTGGATCTACCTGCTGGAAATCCTTTGGAGACTGGGCGCCACCATCTGGC AGCTGCTGGCCTTTTTCCTGGCCTTCTTTCTGGATATCATCCTCCTCATCATTGCCCTGTACCTGCAGCAGAACTGGTGGACC CTGCTGGTGGATCTGCTTTGGCTGCTGCTCTTTCTGGCCATCCTGATTTGGATGTACTACCACGGCCAGCGGCCTTTCGCCGA GGACAAGACCTACAAGTACATCTGCCGGAACTTCAGCAACTTCTGCAACGTGGACGTGGTGGAAATTCTGCCCTACCTGCCTT GCCTGACCGCCAGAGATCAGGACAGACTGAGAGCCACATGTACCCTGAGCGGCAACAGAGACACACTGTGGCACCTGTTCAAC ACCCTGCAGAAGGCCTGGCTGGGTCGAGTACTTTATCGCCGCTCTGAGAGGCTGCGAGCTGGTCGATCTGGCTGATGAAGT GGCCAGCGTGTACCAGAGCTACCAGCCTAGAACCAGCGACCGGGGCGAGAATAGCGAACAGGCTCTGCAGACACTGAGCCCCA GAGCCATTCCTAGAAACCCTGATGGCGGCCCTCTGGAAAGCTCTAGTGATCTGGCCGCTCTGTCCCCTCTGACAAGCTCTGGA CACCAAGAGCAGGATACCGAGCTGGGCAGCACACATACAGCCGGCGCTACAAGCAGCCTGACACCTTCTAGAGGCCCCGTGTC TCCCAGCGTGTCATTTCAGCCTCTGGCCAGGTCTACCCCTAGGGCTTCTAGACTGCCTGGACCAACAGGCAGCGTGGTGTCTA CCGGCACAAGCTTCAGCTCTAGCTCTCCTGGACTGGCTAGTGCCGGTGCCGCTGAGGGAAAACAAGGCGCCGAATCTGATCAG GCCGAGCCTATCATCTGTAGCAGCGGAGCAGAAGCCCCTGCCAATAGCCTGCCTAGCAAGGTGCCAACCACACTGATGCCCGT GAACACAGTGGCCCTGAAGGTGCCAGCTAATCCTGCCTCCGTGTCCACCGTGCCTTCTAAGCTGCCAACCAGCTCTAAGCCAC CTGGCGCCGTGCCATCTAACGCCCTGACAAATCCTGCTCCAAGCAAGCTGCCCATCAACTCCACAAGAGCCGGCATGGTGCCC TCTAAGGTGCCCACATCTATGGTGCTGACCAAGGTGTCCGCCAGCACCGTGCCAACAGATGGCAGCTCCAGAAACGAGGAAAC CCCTGCCGCTCCTACTCCTGCTGGCGCTACAGGCGGATCTTCTGCTTGGCTGGATAGCAGCAGCGAGAACAGAGGCCTGGGCA GCGAGCTTTCTAAACCTGGCGTGCTGGCTTCCCAGGTGGACAGCCCATTTTCCGGCTGCTTTGAGGACCTGGCTATCAGCGCC TCTACAAGCCTCGGCATGGGACCTTGTCACGGCCCCGAGGAAAACGAGTACAAGAGCGAGGGCACCTTCGGCATCCACGTGGC CGAGAATCCTAGCATCCAACTGCTGGAAGGCAACCCCGGACCTCCAGCTGATCCAGATGGCGGACCAAGACCTCAGGCCGACA

GAAAGTTCCAAGAGCGCGAGGTGCCCTGCCACAGACCTTCTCCA

Protein sequence
                                                                    (SEQ ID NO: 6)
MDLDLERGPPGPRRPPRGPPLSSSIGLALLLLLLALLFWLYIIMSNWTGGALLVLYAFALMLVIIILIIFIFRRDLLCPLGAL CLLLLMITLLLIALWNLHGQALYLGIVLFIFGCLLVLGLWIYLLEILWRLGATIWQLLAFFLAFFLDIILLIIALYLQQNWWT LLVDLLWLLLFLAILIWMYYHGQRPFAEDKTYKYICRNFSNFCNVDVVEILPYLPCLTARDQDRLRATCTLSGNRDTLWHLFN TLQRRPGWVEYFIAALRGCELVDLADEVASVYQSYQPRTSDRGENSEQALQTLSPRAIPRNPDGGPLESSSDLAALSPLTSSG HQEQDTELGSTHTAGATSSLTPSRGPVSPSVSFQPLARSTPRASRLPGPTGSVVSTGTSFSSSSPGLASAGAAEGKQGAESDQ AEPIICSSGAEAPANSLPSKVPTTLMPVNTVALKVPANPASVSTVPSKLPTSSKPPGAVPSNALTNPAPSKLPINSTRAGMVP SKVPTSMVLTKVSASTVPTDGSSRNEETPAAPTPAGATGGSSAWLDSSSENRGLGSELSKPGVLASQVDSPFSGCFEDLAISA

STSLGMGPCHGPEENEYKSEGTFGIHVAENPSIQLLEGNPGPPADPDGGPRPQADRKFQEREVPCHRPSP
```

Another preferred adjuvant is the fusion protein LMP1 (delta IC) hIPS1 (delta TM reversed), which contains LMP1 from Epstein Barr virus, without the intracytoplasmic region, in fusion with amino acids 2-439 of human IPS1 (a truncated IPS1 with the transmembrane domain removed and presented in reverse amino acid order, i.e., 439 to 2, C-terminal to N-terminal direction of native IPS1). In the fusion protein, the first amino acid (methionine) of human IPS1 was removed. The fusion protein is codon optimized for human use. The DNA and encoded amino acid sequences of this fusion protein are shown below:

```
DNA sequence:
                                                                  (SEQ ID NO: 7)
ATGGATCTGGATCTCGAAAGAGGACCTCCTGGACCTAGACGGCCTCCTAGAGGACCACCTCTGAGCAGCTCTATTGGACTGGC
CCTGCTGCTGCTTCTGCTGGCTCTGCTGTTCTGGCTGTACATCATCATGAGCAACTGGACCGGCGGAGCACTGCTGGTGCTGT
ATGCCTTTGCTCTGATGCTGGTCATCATCATCCTGATCATCTTCATCTTCCGGCGGGACCTGCTGTGTCCTCTGGGAGCACTT
TGTCTGTTGCTGCTGATGATCACCCTCCTGCTGATCGCCCTGTGGAACCTGCATGGACAGGCCCTGTATCTGGGCATCGTGCT
GTTCATCTTCGGCTGCCTGCTGGTTCTCGGCCTGTGGATCTACCTGCTGGAAATCCTTTGGAGACTGGGCGCCACCATCTGGC
AGCTGCTGGCCTTTTTCCTGGCCTTCTTTCTGGATATCATCCTCCTCATCATTGCCCTGTACCTGCAGCAGAACTGGTGGACC
CTGCTGGTGGATCTGCTTTGGCTGCTGCTCTTTCTGGCCATCCTGATTTGGATGTACTACCACGGCCAGCGGCCTTCTCCAAG
ACACTGCCCAGTGGAAAGAGAGCAGTTCAAGAGGGACGCCCAGCCTAGACCTGGCGGAGATCCTGATGCTCCACCTGGACCAA
ATGGCGAGCTGCTGCAGATCAGCCCTAATGAGGCCGTGCACATCGGCTTCACCGGCGAGTCTAAGTACGAGAACGAGGAACCC
GGCCACTGTCCTGGCATGGGCCTTTCTACATCTGCCTCTATCGCCCTGGACGAGTTCTGCGGCAGCTTTCCATCTGATGTGCA
GTCTGCCCTCGTGGGCCCTAAGTCTCTGGAATCTGGCCTGGGCAGAAACGAGAGCAGCTCCGATCTGTGGGCTAGCTCTGGTG
GAACAGCTGGCGCTCCTACACCAGCCGCTCCTACCGAAGAGAATAGAAGCAGCGGCGACACCCCTGTGACAAGCGCCTCTGTG
AAAACCCTGGTCATGAGCACCCCAGTGAAGTCCCCAGTGATGGGCGCCAGAACCTCCAACATTCCCCTGAAGTCTCCCGCTCC
TAACACACTGGCCAACTCTCCAGTGGCTGGCCCTCCTAAGTCTAGCACCCCTCTGAAAAGCCCCGTGACCTCTGTGTCTGCCC
CTAACGCTCCTGTGAAACTGGCCGTGACCAACGTGCCCATGCTGACCACACCTGTGAAATCCCCACTGAGCAATGCCCCTGCC
GAGGCCGGAAGCTCTTGTATCATTCCCGAGGCTCAGGATAGCGAGGCTGGCCAAAAAGGCGAAGCTGCAGGCGCTTCTGCTCT
GGGCCCTAGCTCTAGCTCTTTTAGCACCGGCACCAGCGTGGTGTCTGGCACACCAGGACCTCTGAGAAGCGCCAGACCTACCT
CTAGAGCCCTGCCTCAGTTTAGCGTGTCCCCTAGTGTGCCTGGCAGAAGCCCTACACTGTCTAGTACAGCCGGCGCTACACAC
ACCAGCGGACTGGAAACAGACCAAGAACAGCATGGCAGCAGCACCCTGCCTTCTCTGGCTGCCCTTGATTCTAGCAGCGAACT
GCCAGGCGGCGACCCCAATAGACCTATCGCTAGACCTAGCCTGACACAGCTGGCCCAAGAGAGCAATGAGGGCCCTTCTGAGC
CTGCTCAGACCGAACAGGTGCCAATGCCTTACAGCCCCGAGAAAGAGCGGTGCAGCAACTACCCTATCAGCCATGCCGCTGCT
CCCACACCTCCTGGTCCAAGAGAAGCTCCTCTGAGCCCTCCTGAGCTGCCCGATCCTCCAAGAGATAGCACCAGACCTCAGTA
CTCCCAGTACGTGTCCGCCGTGGAAGATGCCCTGGATGTGCTGGAATGTGGCAGACTGGCCGCCATCTTCTACGAAGTGTGGG
GCCCTAGAAGGCAGCTGACCAACTTTCTGCACTGGCTGACCGACAGAAACGGCAGCCTGACATGTACCGCCAGACTGAGAGAT
CAGGACCGGGCCACACTGTGCCCTCTGTATCCTCTGATCGAGGTGGTGGACGTGAACTGCTTCAACAGCTTCAACCGGTGCAT
CTACAAGTACACCAAGGACGAGGCTTTCCCTATG Protein sequence
                                                                  (SEQ ID NO: 8)
MDLDLERGPPGPRRPPRGPPLSSSIGLALLLLLLALLFWLYIIMSNWTGGALLVLYAFALMLVIIILIIFIFRRDLLCPLGAL
CLLLLMITLLLIALWNLHGQALYLGIVLFIFGCLLVLGLWIYLLEILWRLGATIWQLLAFFLAFFLDIILLIIALYLQQNWWT
LLVDLLWLLLFLAILIWMYYHGQRPSPRHCPVEREQFKRDAQPRPGGDPDAPPGPNGELLQISPNEAVHIGFTGESKYENEEP
GHCPGMGLSTSASIALDEFCGSFPSDVQSALVGPKSLESGLGRNESSSDLWASSGGTAGAPTPAAPTEENRSSGDTPVTSASV
KTLVMSTPVKSPVMGARTSNIPLKSPAPNTLANSPVAGPPKSSTPLKSPVTSVSAPNAPVKLAVTNVPMLTTPVKSPLSNAPA
EAGSSCIIPEAQDSEAGQKGEAAGASALGPSSSSFSTGTSVVSGTPGPLRSARPTSRALPQFSVSPSVPGRSPTLSSTAGATH
TSGLETDQEQHGSSTLPSLAALDSSSELPGGDPNRPIARPSLTQLAQESNEGPSEPAQTEQVPMPYSPEKERCSNYPISHAAA
PTPPGPREAPLSPPELPDPPRDSTRPQYSQYVSAVEDALDVLECGRLAAIFYEVWGPRRQLTNFLHWLTDRNGSLTCTARLRD
QDRATLCPLYPLIEVVDVNCFNSFNRCIYKYTKDEAFPM
```

In preferred embodiments, an immune checkpoint inhibitor molecule is encoded within the viral vector, enhancing the immune response against a tumor. The immune checkpoint inhibitor molecule can be, but is not limited to, an anti-CTLA-4 molecule, a PD 1 blocker, and a PDL1 blocker. The immune checkpoint inhibitor molecule can be a protein, such as an antibody, or a soluble form of an anticheckpoint.

In certain embodiments, the viral vector may include more than one expression cassette. In some embodiments, the viral vector particles may include more than one nucleic acid molecule, such as two or three nucleic acid molecules, which may be delivered separately or operatively linked. In some embodiments, the second nucleic acid encodes an antigen and/or soluble immune checkpoint inhibitor molecule or soluble immune modulator molecule. In some embodiments, the third nucleic acid encodes an antigen and/or immune checkpoint inhibitor molecule different from that encoded by the second nucleic acid molecule.

In one aspect, the technology is an immunotherapeutic formulation for preventing or treating a disease or condition in a subject. The vaccine includes a therapeutically effective amount of the viral vector. The disease may be any disease in which vaccination against an agent is desirable, such as cancer or an infection.

In another aspect the technology is a method for inducing or enhancing an immune response against cancer or infection in a subject. The method includes administering a therapeutically effective amount of the viral vector or immunotherapeutic formulation to a subject in need thereof.

EXAMPLES

Example 1. Molecular Constructs

Vectors were constructed to contain the following genetic elements: (a) a promoter, preferably a human ubiquitin promoter; (b) a reporter gene (e.g., green fluorescent protein) or, alternatively, one or more antigens fused into a single transgene; and (c) an IRES followed by an adjuvant gene (i.e., LMP1-IPS1CO or a functional variant thereof). Optionally, the vectors can include (d) an IRES followed by soluble immune checkpoint inhibitor genes or soluble immune modulator genes (FIGS. 8C). Preferably, the sequences are in the aforementioned order, but the genes can be situated in the vector in any other suitable order. Control vectors were also constructed that had some, but not all the above mentioned regions.

Example 2. Production of Viral Vectors

Lentiviral vectors were produced by transient calcium-phosphate transfection of HEK 293T cells Line as described in Nasri et al. (2014). HEK 293T cells were seeded at $1.6 \times 10^8$ cells in a two chambers Cell Stack (Corning) in 250 mL of complete culture medium and maintained 24 h in an incubator with humidified atmosphere of 5% $CO_2$ at 37° C. to adhere. For each vector produced, one cell stack was transfected as follows. The lentiviral backbone plasmid (235 µg), the envelope coding plasmid (47 µg), and the packaging plasmid (235 µg) were mixed with 8.6 mL of sterile distilled water and 3.0 mL of $CaCl_2$. The DNA mix was then added drop by drop to 12.1 mL of 37° C. pre-warmed HBS 2×, pH=7.1, and the 24.2 mL of precipitate obtained were added to the culture medium of the cells after 30 minutes of incubation at room temperature. The transfected cells were incubated at 37° C., 5% $CO_2$. The medium was replaced 24 h after transfection by 210 mL of harvest medium without serum and phenol red, and the viral supernatant was harvested after an additional 24h, clarified by centrifugation for 5 min at 2500 rpm. The harvest clarified bulk (210 mL) was treated 30 min with DNase I in the presence of $MgCl_2$ to cleave any residual DNA, and concentrated by centrifugation 1 h at 22000 rpm, 4° C. Vector pellets were resuspended in 70 µl of Tris-Trehalose (50 mM), pooled in a 1.5mL microtube and divided into 50 µL aliquots, frozen and stored at ≤−70° C. Production yields were a bit less effective with adjuvanted vectors compared to GFP vector, certainly due to the presence of longer DNA cassettes. However, for all adjuvanted constructions titers were at least in the $10^9$ TU/mL range and were consistently obtained throughout different production campaigns. Therefore, no issue regarding the future industrial bioproduction of these adjuvanted constructions has to be anticipated.

Example 3. In Vitro Effects of Lentiviral Vectors Expressing LMP1-IPS1

Fresh human dendritic cells and macrophages were obtained from human healthy donors (leukocyte cones) over a density gradient. CD14+ monocytes were purified from PBMC using a magnetic isolation kit (positive selection) and were plated in 6-well plates in complete RPMI. Monocytes were differentiated into dendritic cells with GM-CSF and IL-4 using published methods. A 10% media change was made after 3 days to replenish cytokines, and cells were harvested after a total of 6 days of culture using non-enzymatic cell dissociation solution. DCs were then re-plated in complete RPMI+4 µg/ml of polybrene+lentiviral construct (at an MOI of 15)+GM-CSF and IL-4. After 2 hours, 700 µl of complete RPMI+GM-CSF/IL-4 was added, and cells were cultured for 96 hours in total. Additional control wells were stimulated with IFN-gamma and LPS for 96 hours, to act as a positive control for activation marker expression.

CD14+ Monocytes were differentiated into M1 or M2 macrophages with GM-CSF (M1) or M-CSF (M2). A 10% media change was made after 3 days to replenish cytokines and cells were harvested after a total of 6 days of culture using non-enzymatic cell dissociation solution, and macrophages were pooled at a 1:1 ratio. M1/M2 macrophages were then re-plated in 300 µl of complete RPMI+4 µg/ml of polybrene+lentiviral construct (at an MOI of 15)+M-CSF). After 2 hours, 700 µl of complete RPMI+M-CSF was added, and cells were cultured for 96 hours in total. Additional control wells were stimulated with IFN-gamma and LPS (M1) or IL-13 and IL-4 (M2) for 96 hours in total, to act as a positive control for activation marker expression.

Human DCs and macrophages were transduced with a MOI of 15 with lentiviral vectors containing expression cassettes as described below:

Construct 1: GFP-IRES-LMP1(dIC)hIP S1
Construct 2: GFP-IRES-LMP1(dIC)hIPS1(dTM)
Construct 3: GFP-IRES-LMP1(dIC)hIPS1(dTMdPro)
Construct 4: GFP-IRES-LMP1(dIC)hIPS1(dTMRev)
Control Construct 1: GFP
Control Construct 2: GFP+LMP1(dIC)
Control Construct 3: cells bitransduced with GFP and LMP1(dIC)hIPS1 (in separate vectors, each at MOI 15).

Figure 8A:
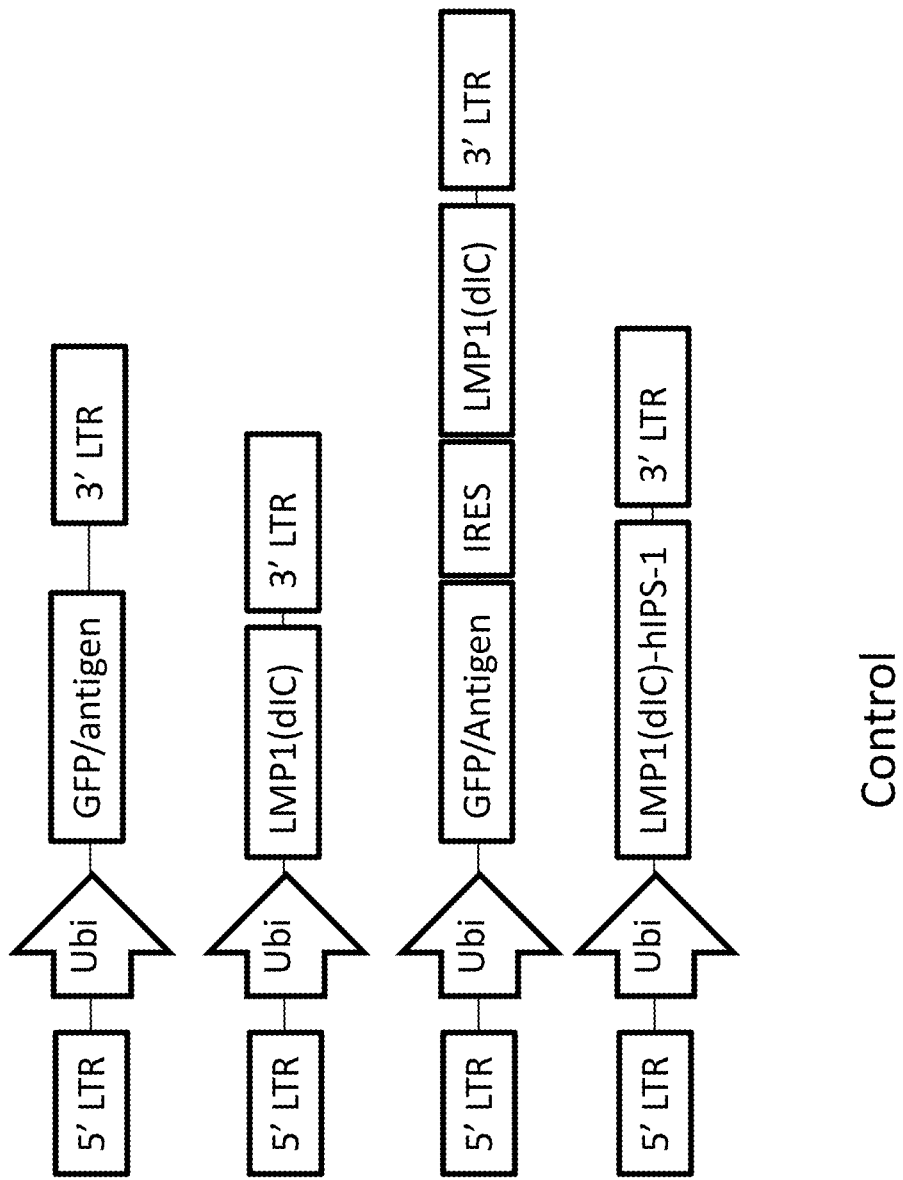
FIGS. 8A-8C show schematic representations of several molecular constructs.
Figure 8B:
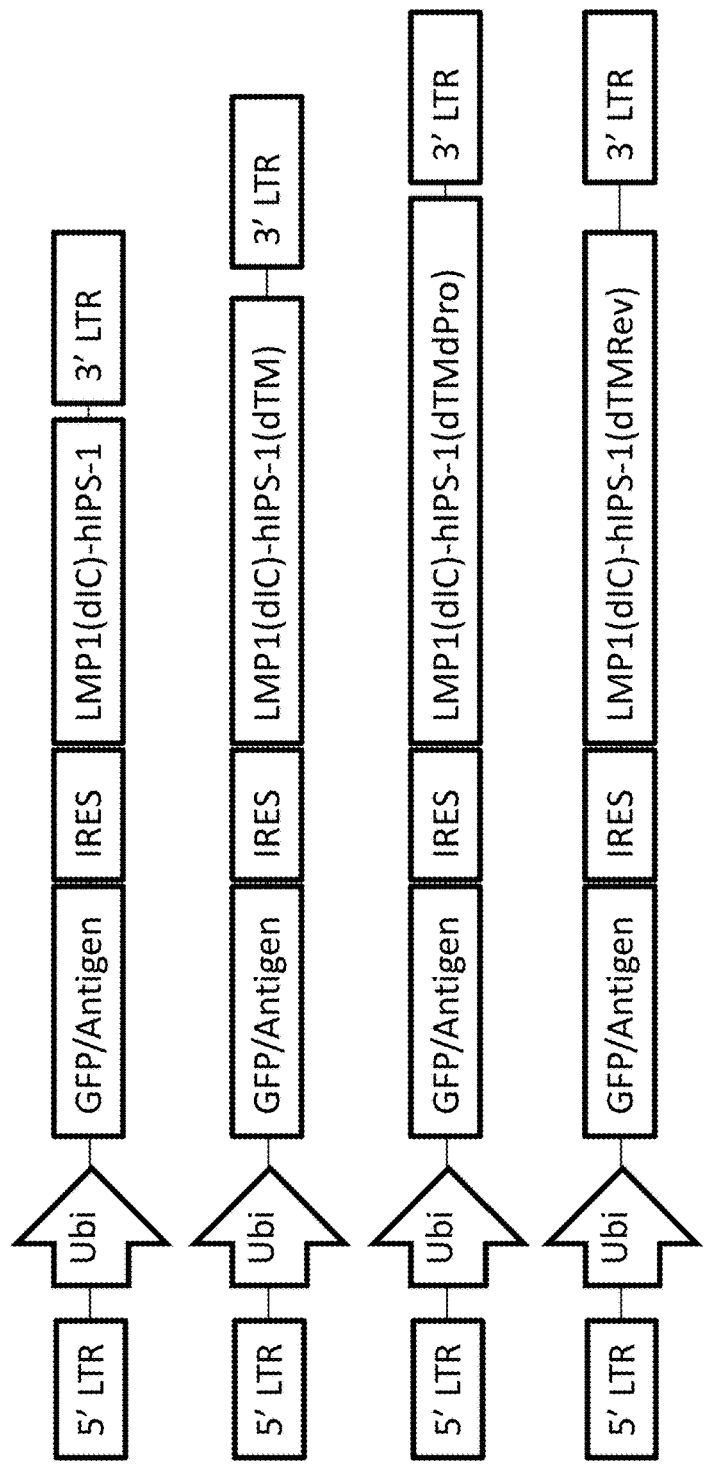
Figure 8C:
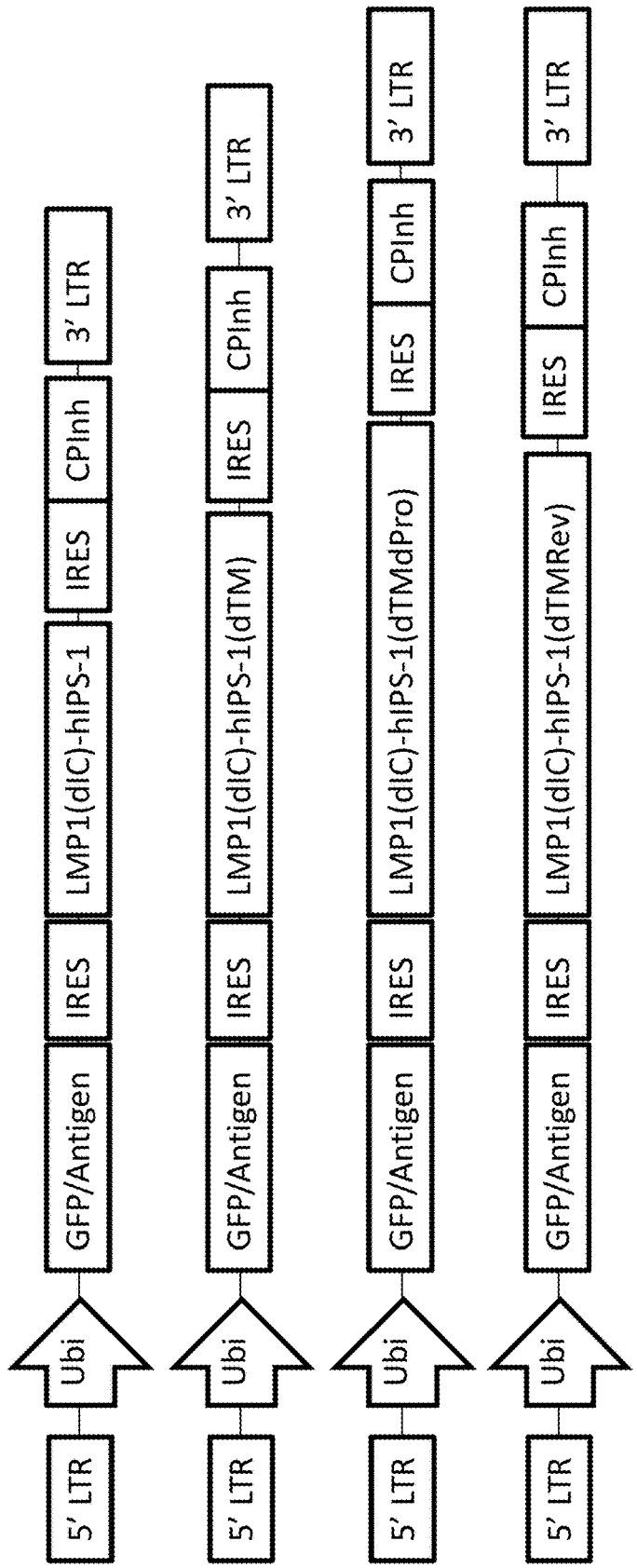

See FIG. 8A for illustrations of the control constructs and FIG. 8B for the adjuvanted constructs Dendritic cell and macrophage proliferation was quantified after 24 h of culture. Triplicate samples were pulsed with $^3$H-TdR and cultured overnight before being harvested and the incorporation of radioactive thymidine determined by standard scintillation counting. Proliferation was slightly reduced with adjuvanted vectors compared to GFP vectors, most likely due to the presence of a longer DNA cassette. As already mentioned, viability of the transduced cells was determined by staining with a fixable viability dye before analysis using a BD FACS Canto System flow cytometer. While slight differences were observed among the adjuvanted vectors, no significant toxicity was found.

Figure 9A:
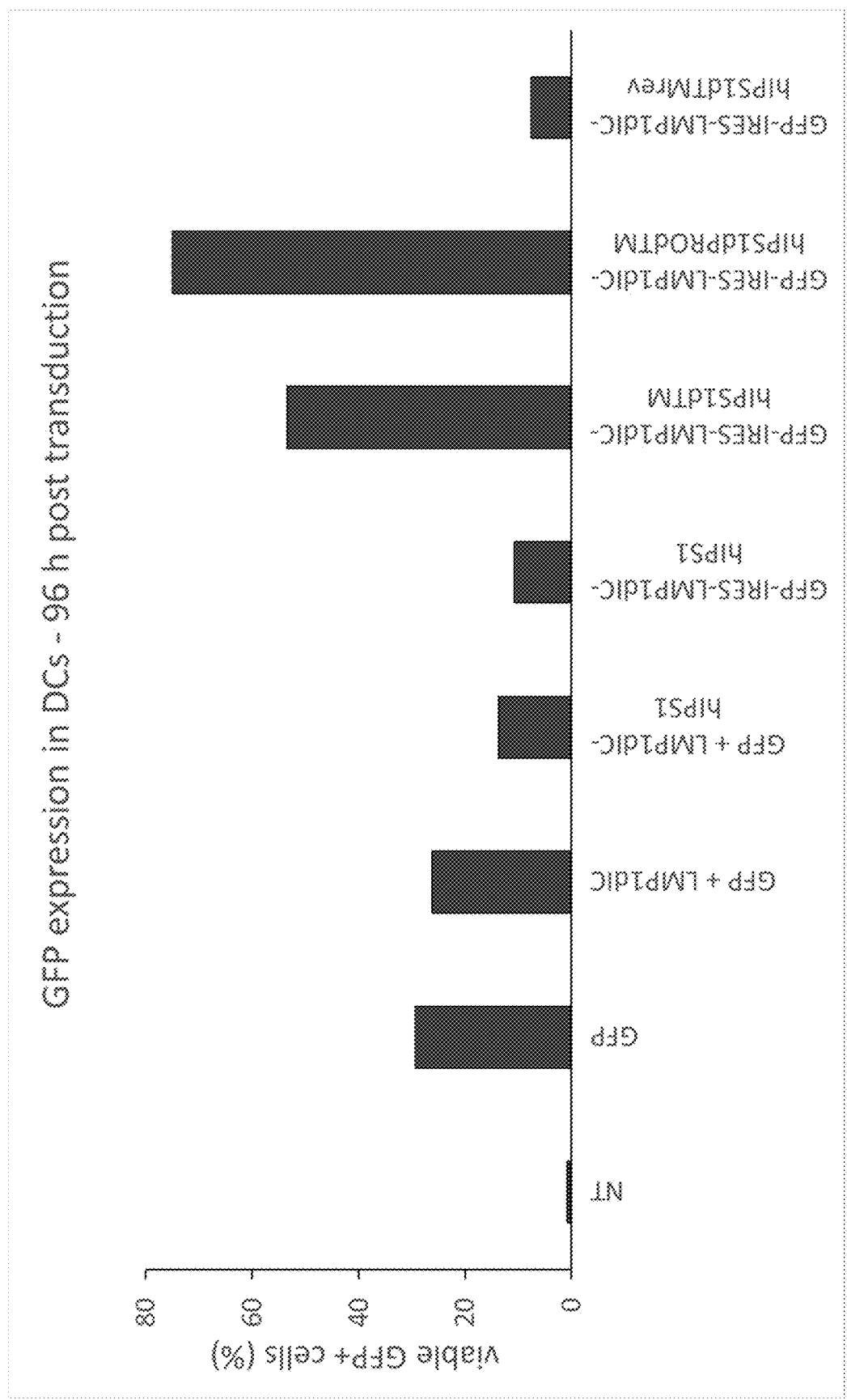
FIGS. 9A-9B show the expression levels of a GFP transgene in human dendritic cells and macrophages transduced by the lentiviral vectors.
Figure 9B:
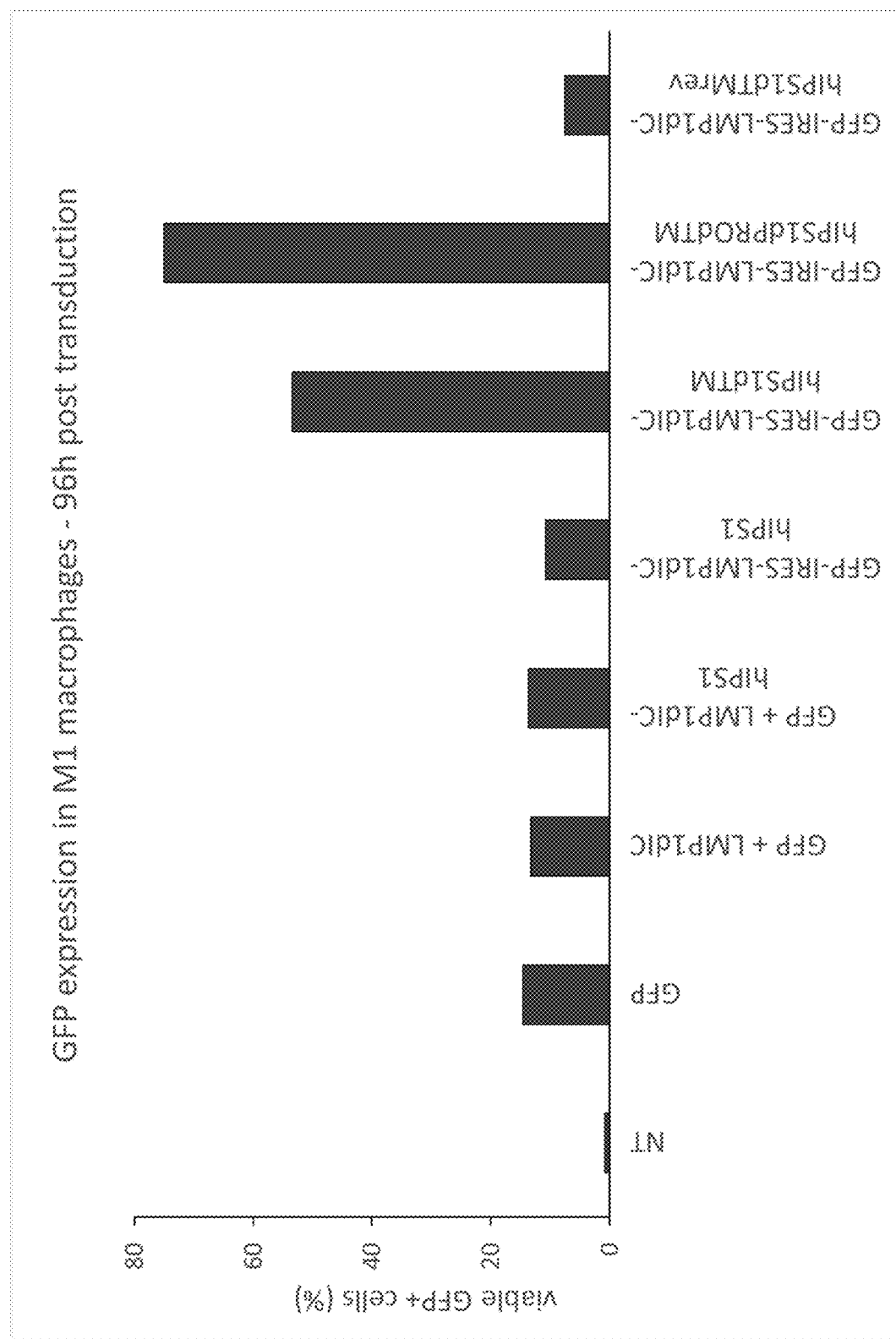

Expression of GFP was determined for cells transduced with each construct by measuring the fluorescence with an Attune N×T flow cytometer after 96 h of culture, and the results are shown in FIGS. 9A (dendritic cells) and 9B (macrophages). Percentage of viable and GFP-positive cells were determined by gating on debris excluded/viable/single cells. Three independent experiments were carried out with PBMCs isolated from different donors. Graphed data represent means of duplicates of a representative experiment. The results are presented in FIGS. 9A (dendritic cells) and 9B (macrophages) and show that for both cell types while slight differences were observed between the adjuvanted vectors, significant expression of the GFP/transgene was observed with all IRES constructions. Among adjuvanted vectors, GFP/transgene expression increased with constructs 2 and 3, most likely due to the presence of a shorter DNA cassette. The removal of the IPS1 transmembrane domain while reversing the orientation of the IPS1 CARD and PRO domains did not result in an improved expression of GFP/transgene.

Figure 10A:
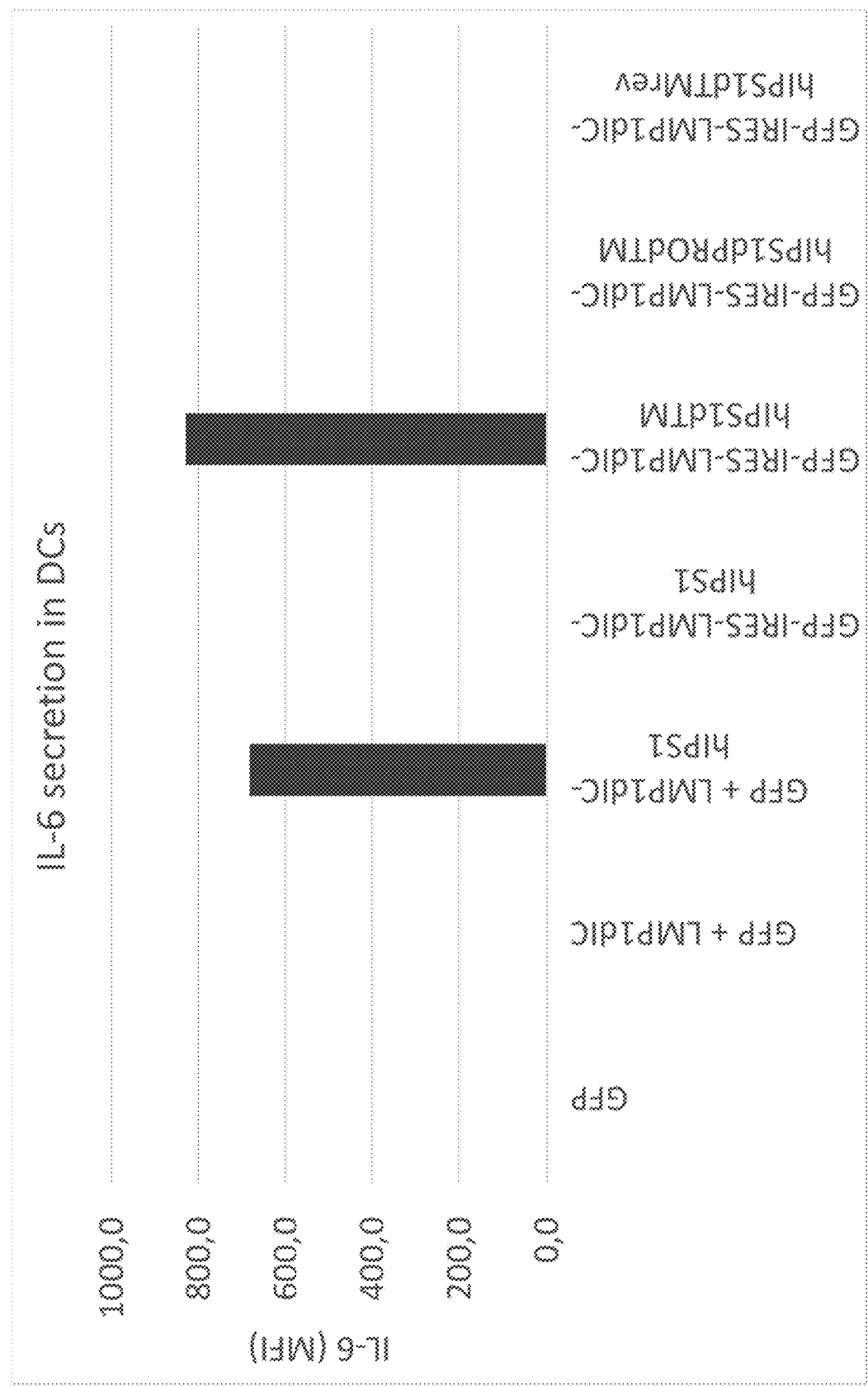
FIGS. 10A-10D show the activation and maturation of human dendritic cells and macrophages induced in vitro by the lentiviral vectors.
Figure 10A:
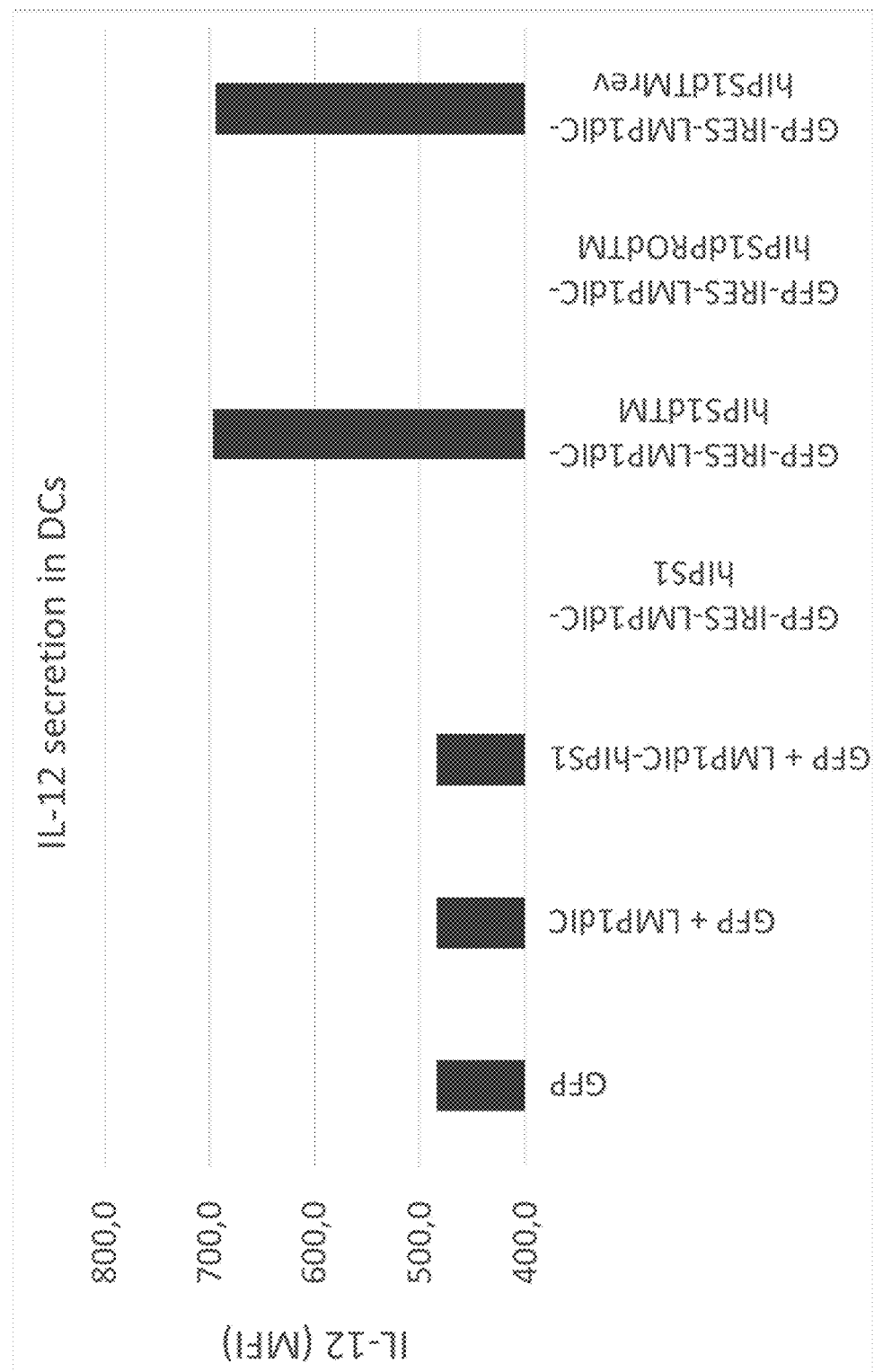
Figure 10A:
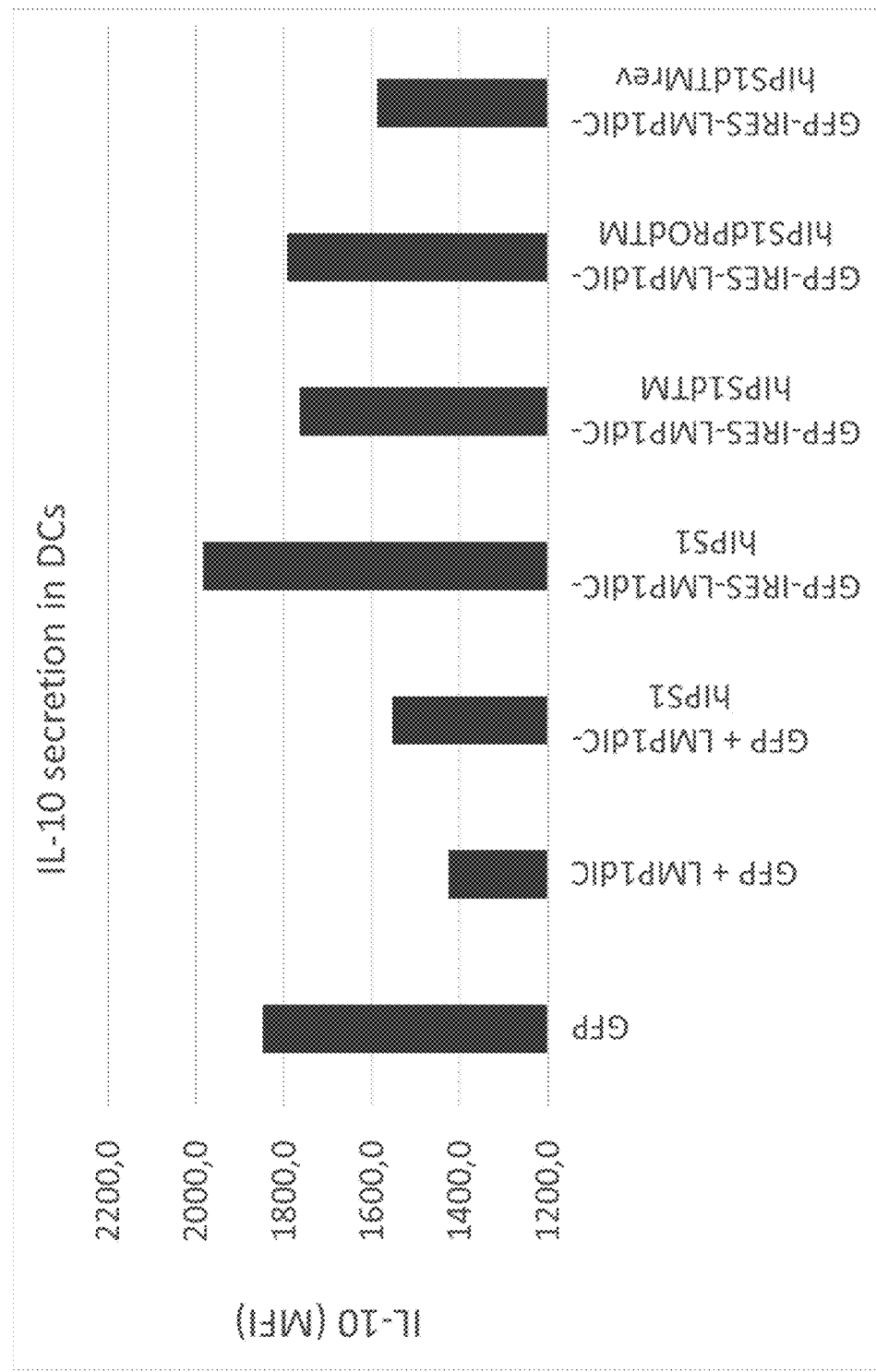
Figure 10A:
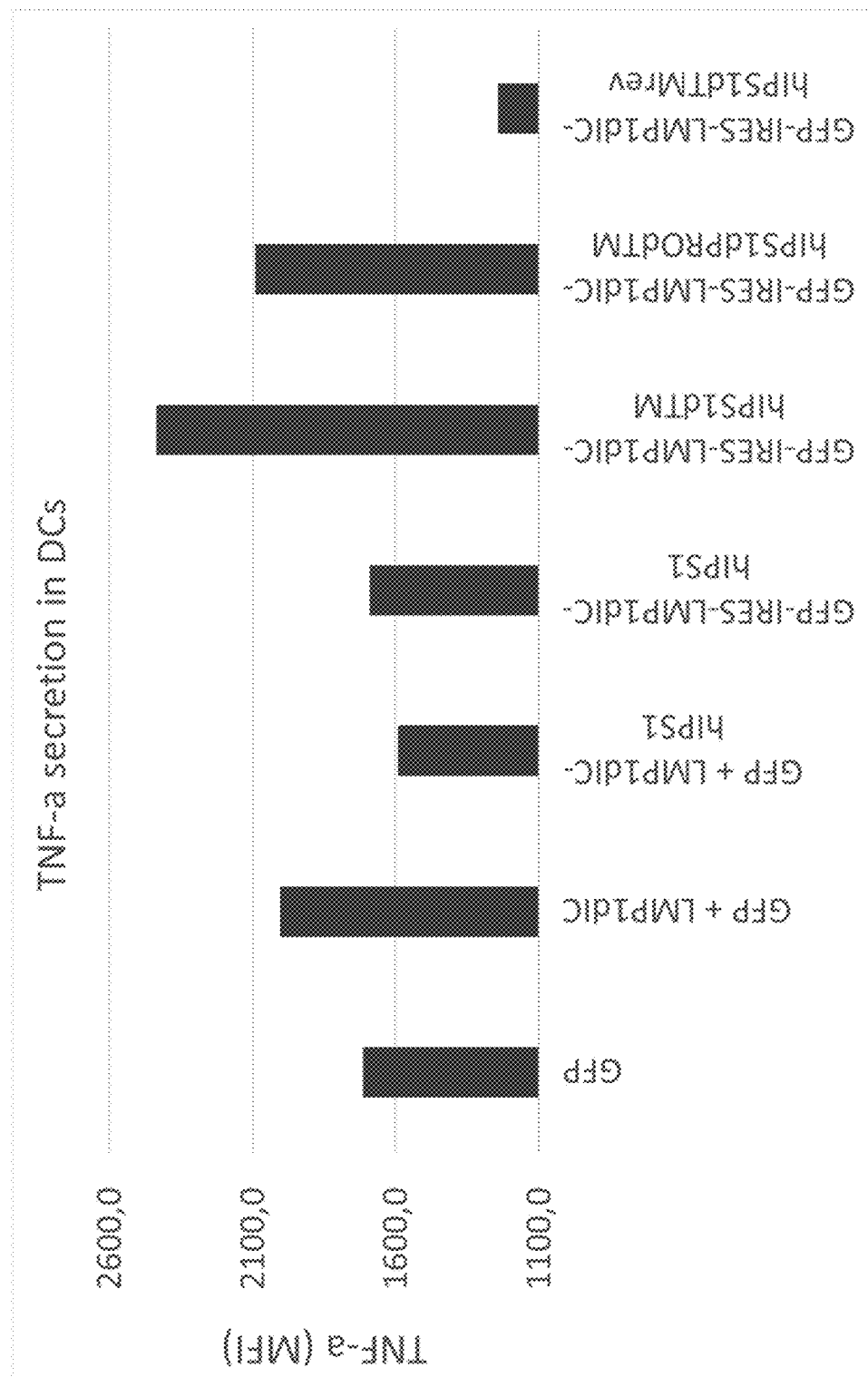
Figure 10B:
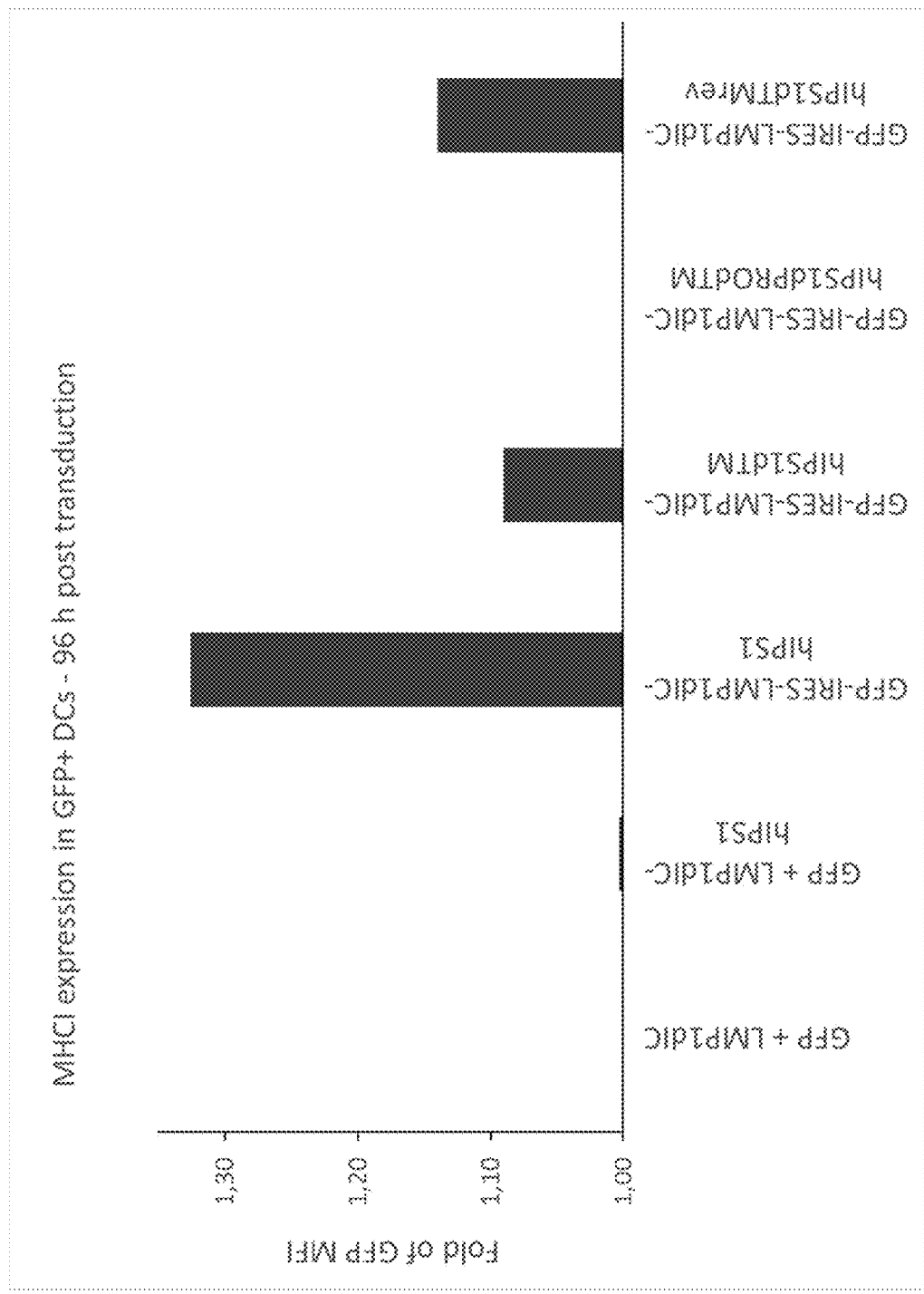
Figure 10B:
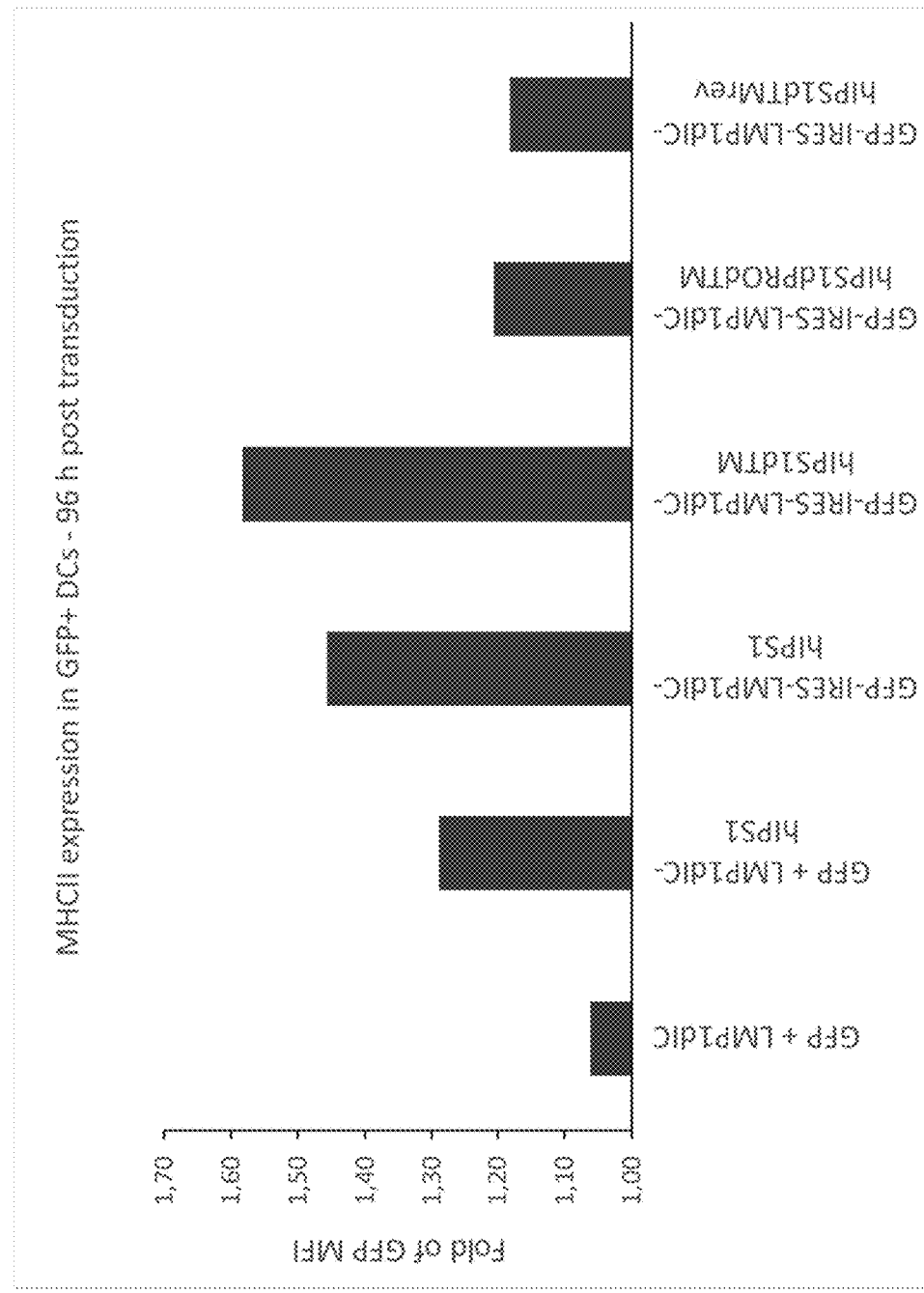
Figure 10B:
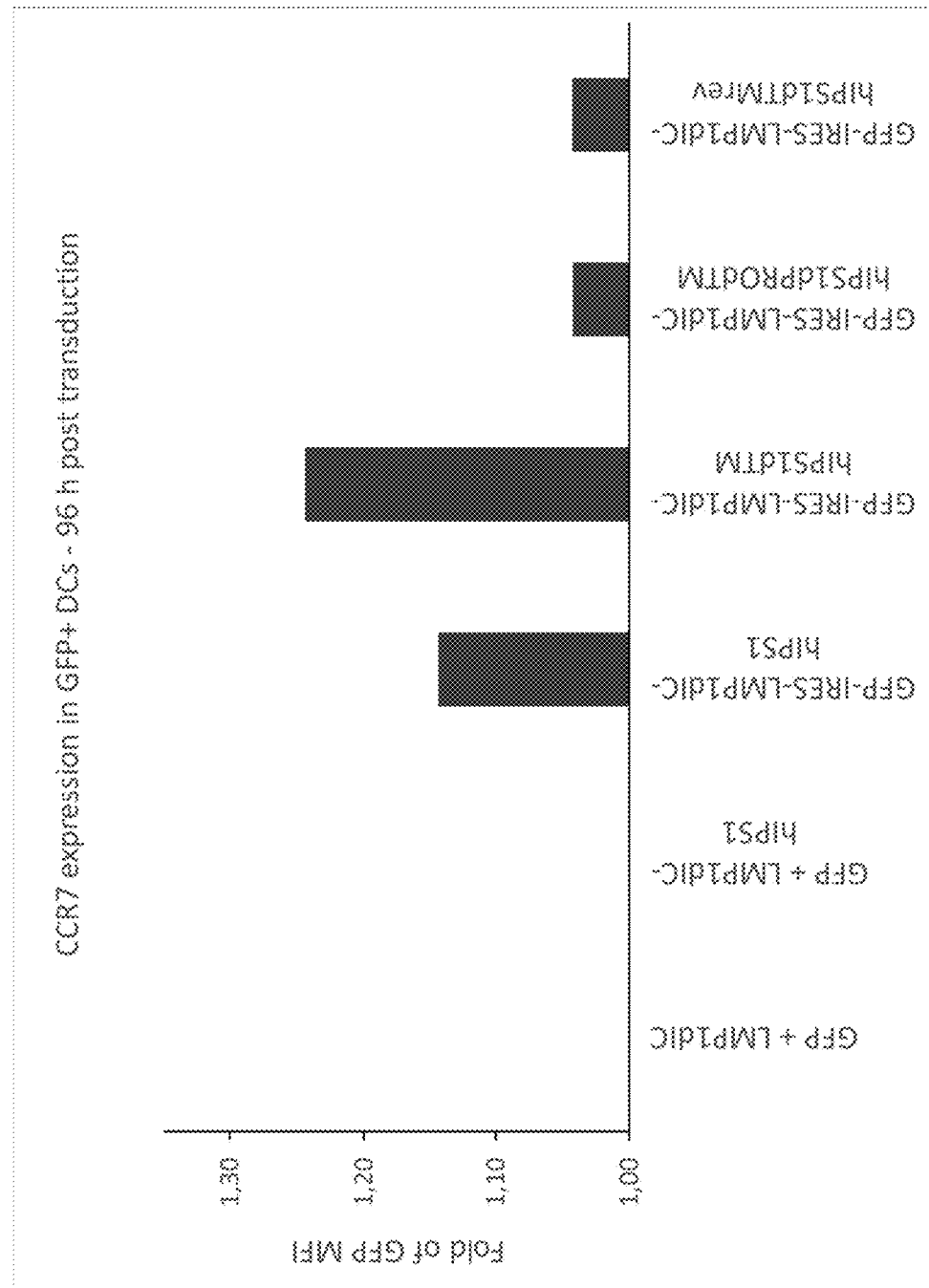
Figure 10B:
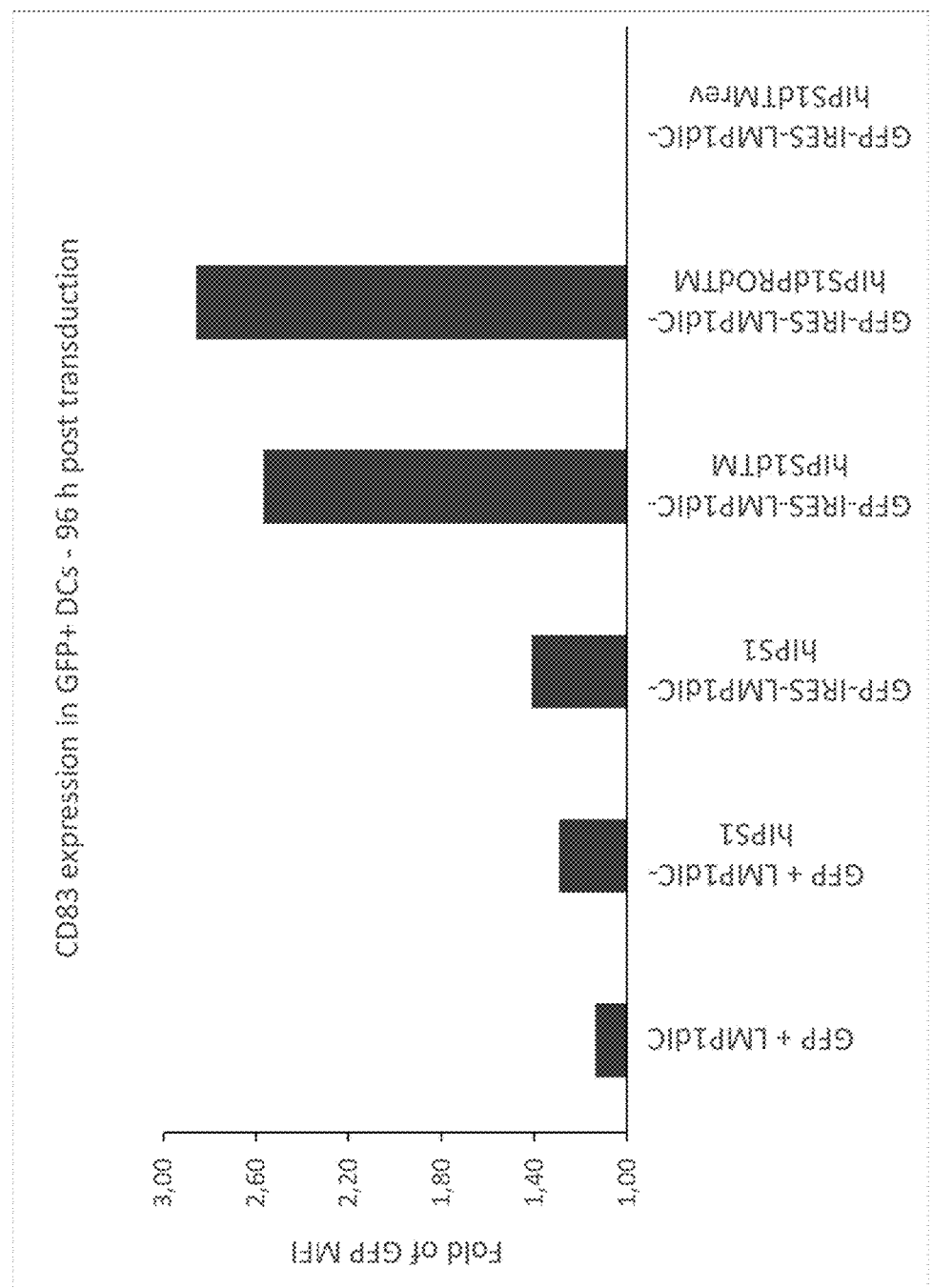
Figure 10B:
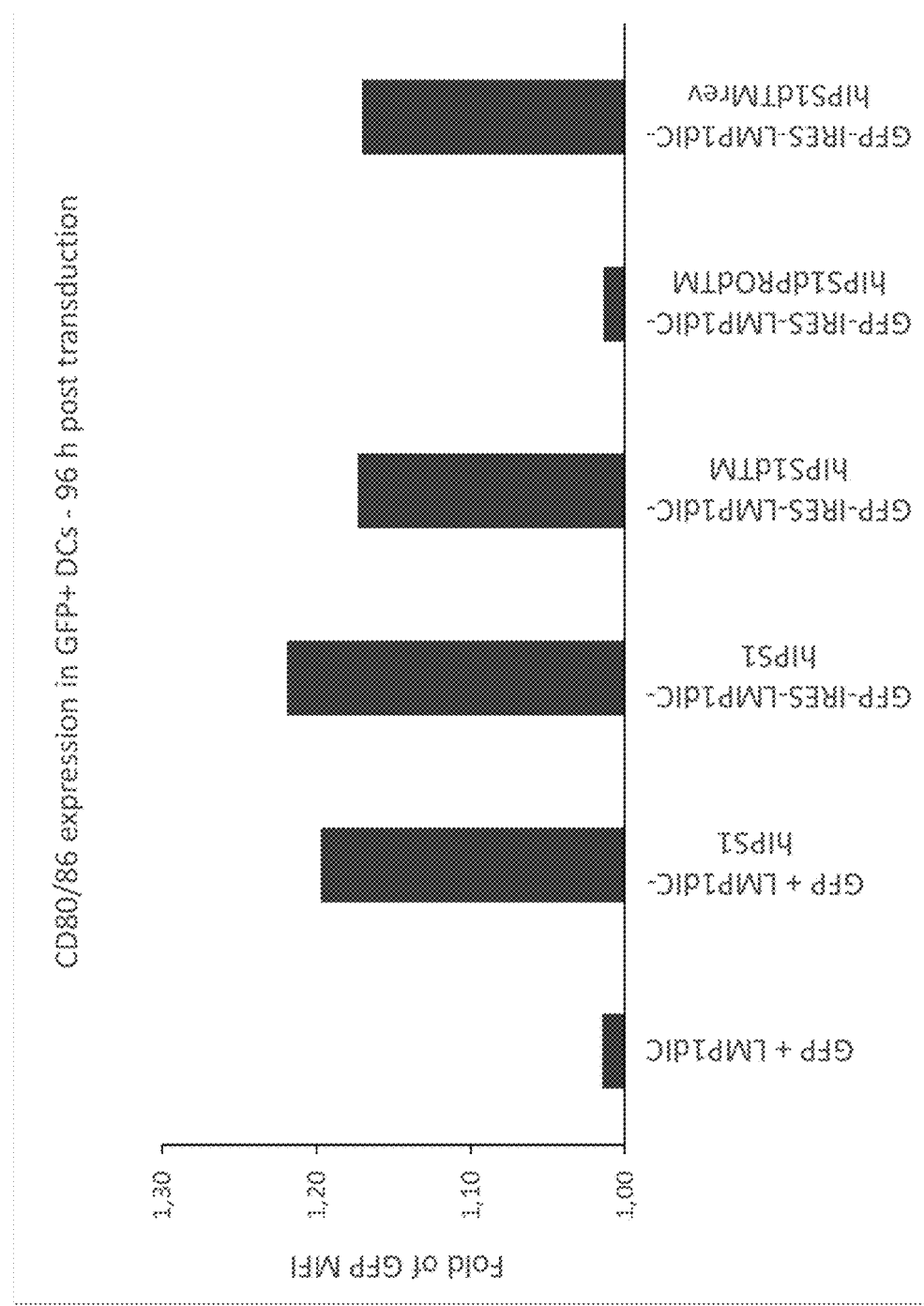
Figure 10B:
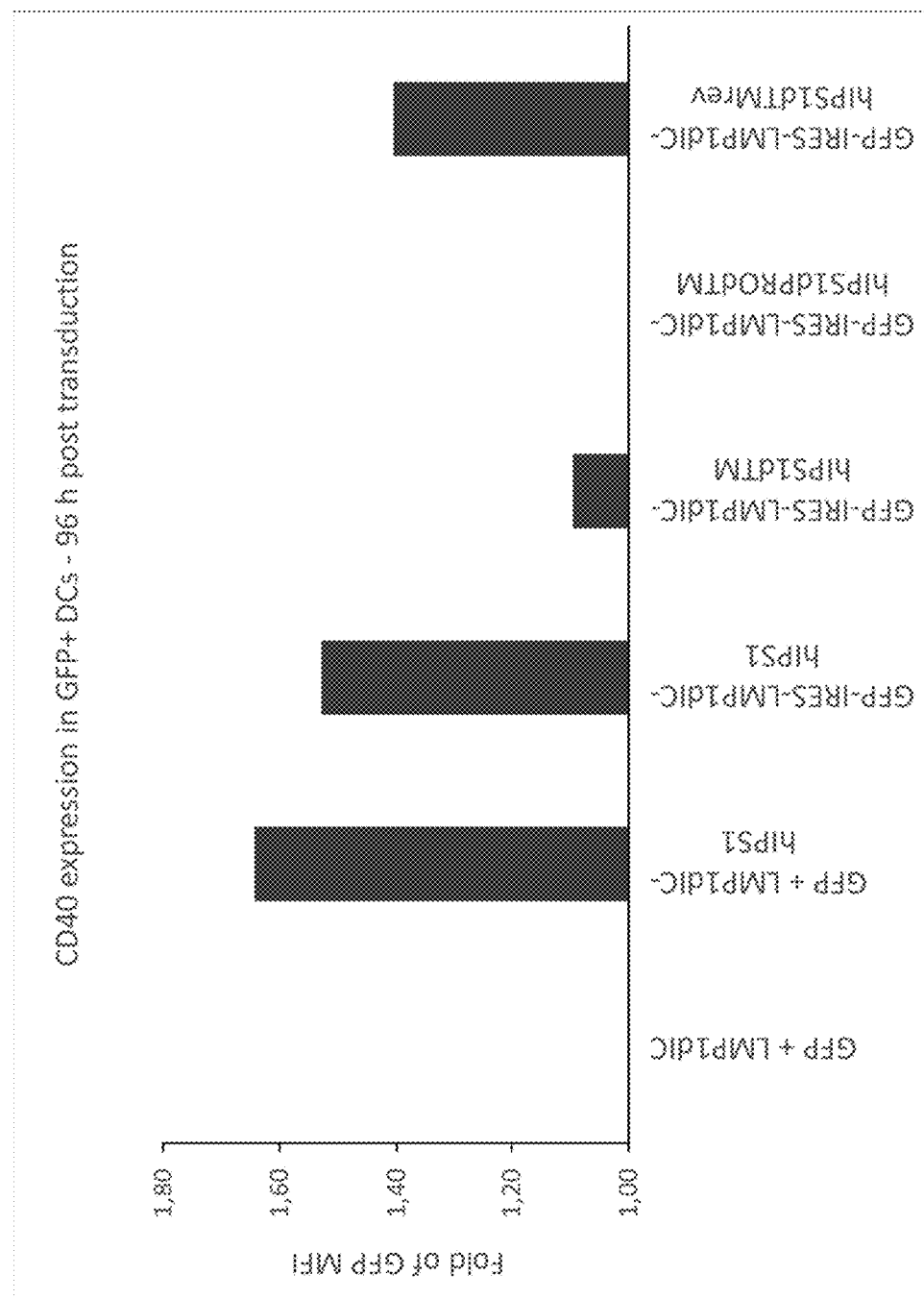
Figure 10C:
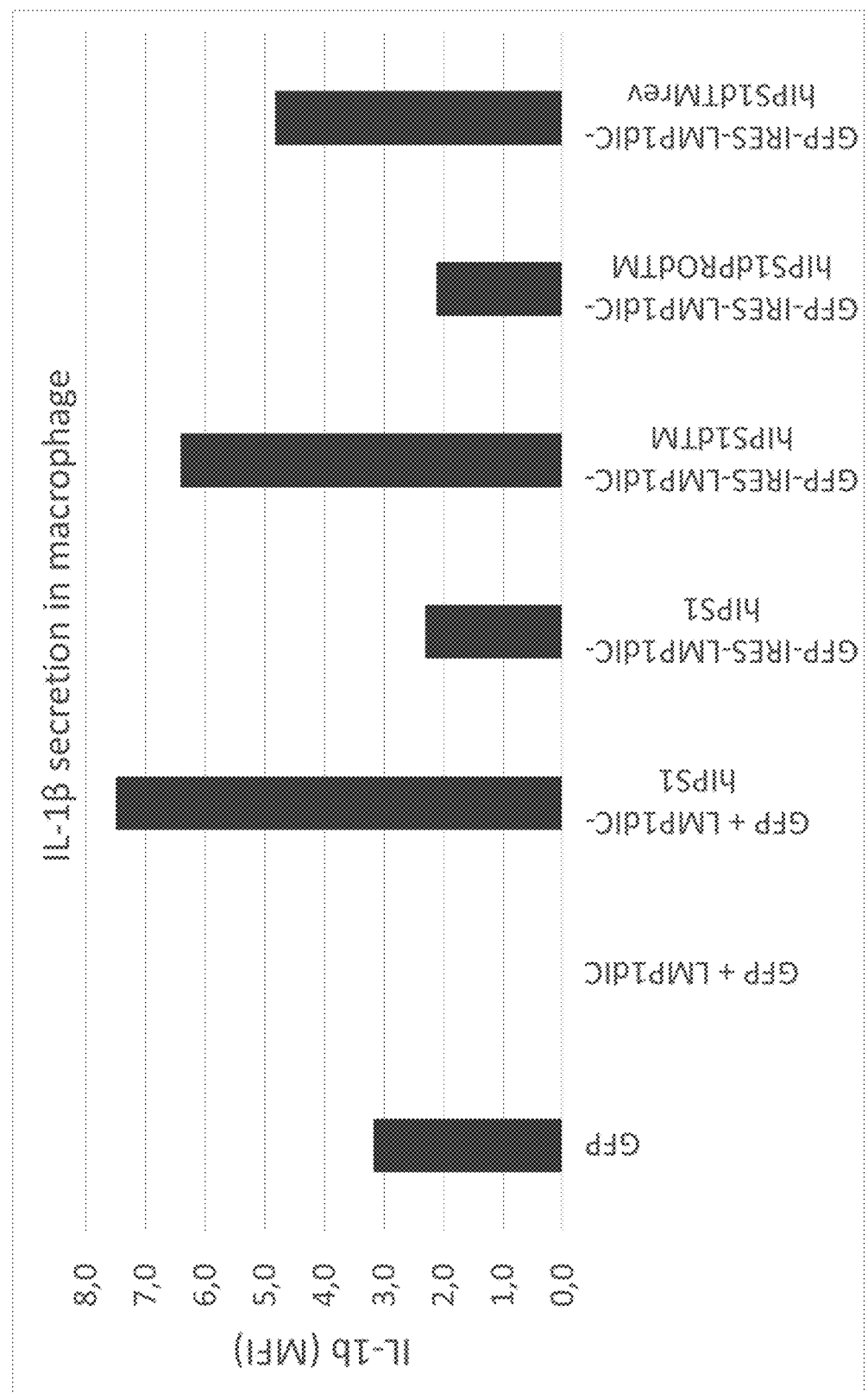
Figure 10C:
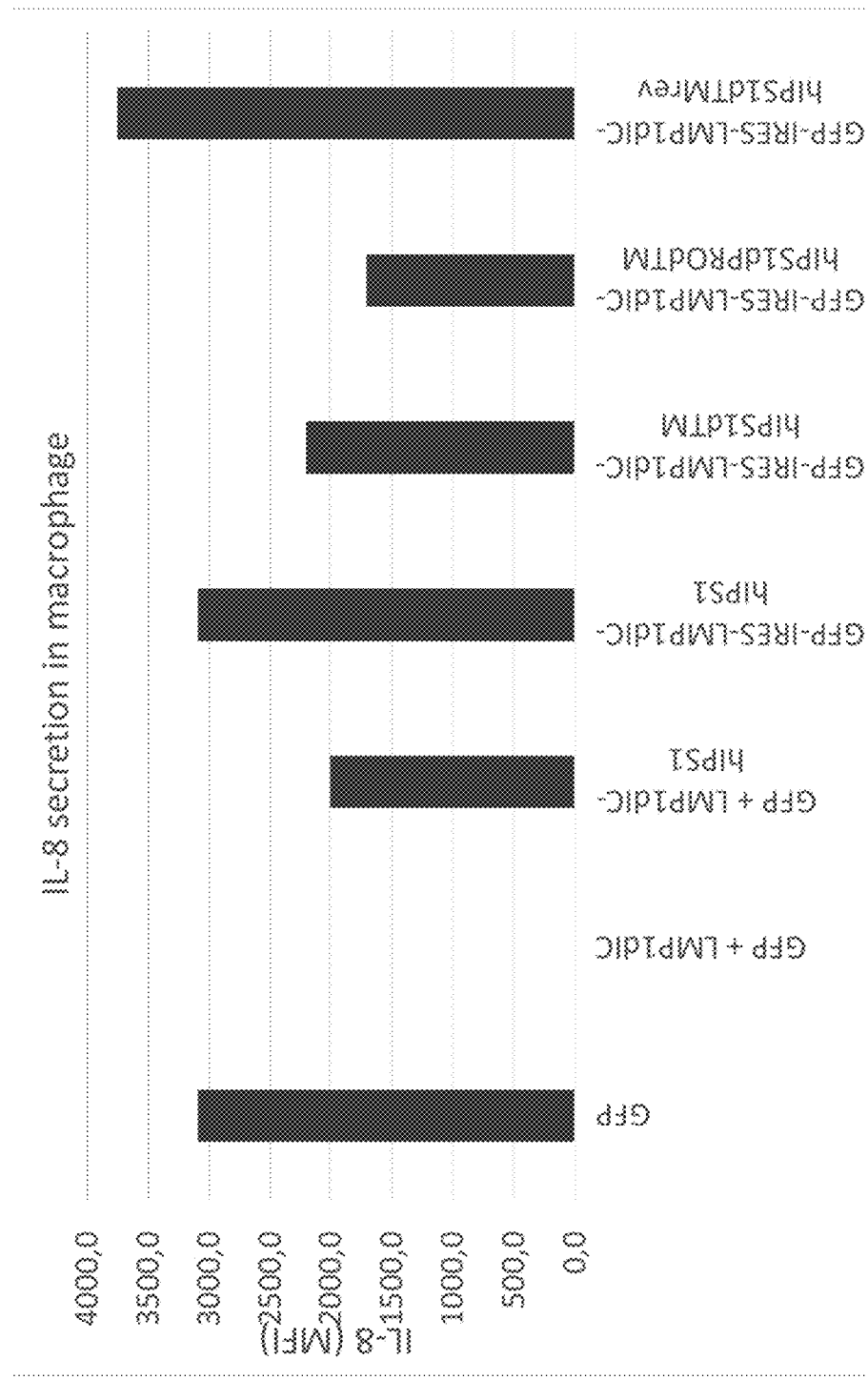
Figure 10C:
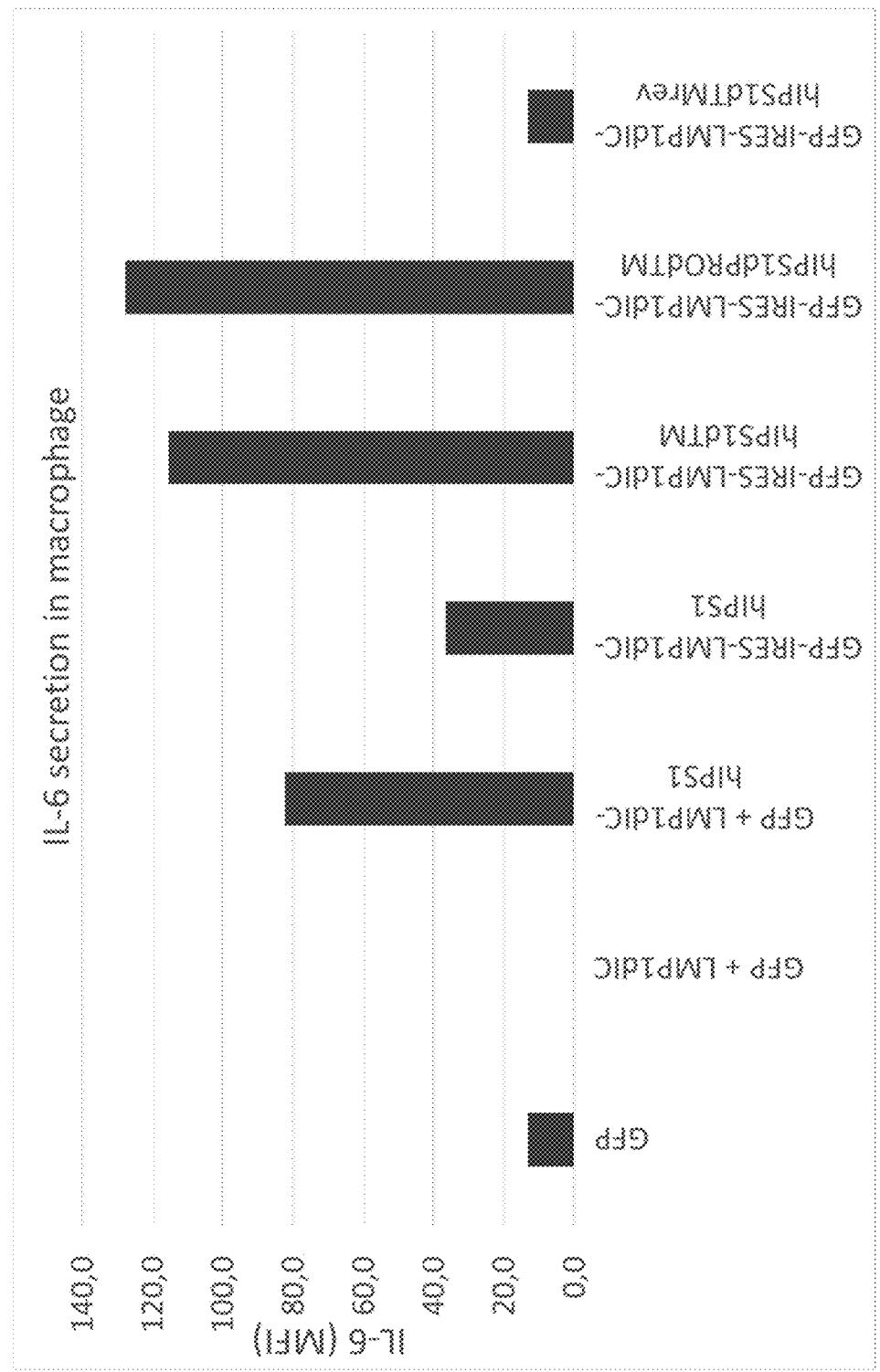
Figure 10C:
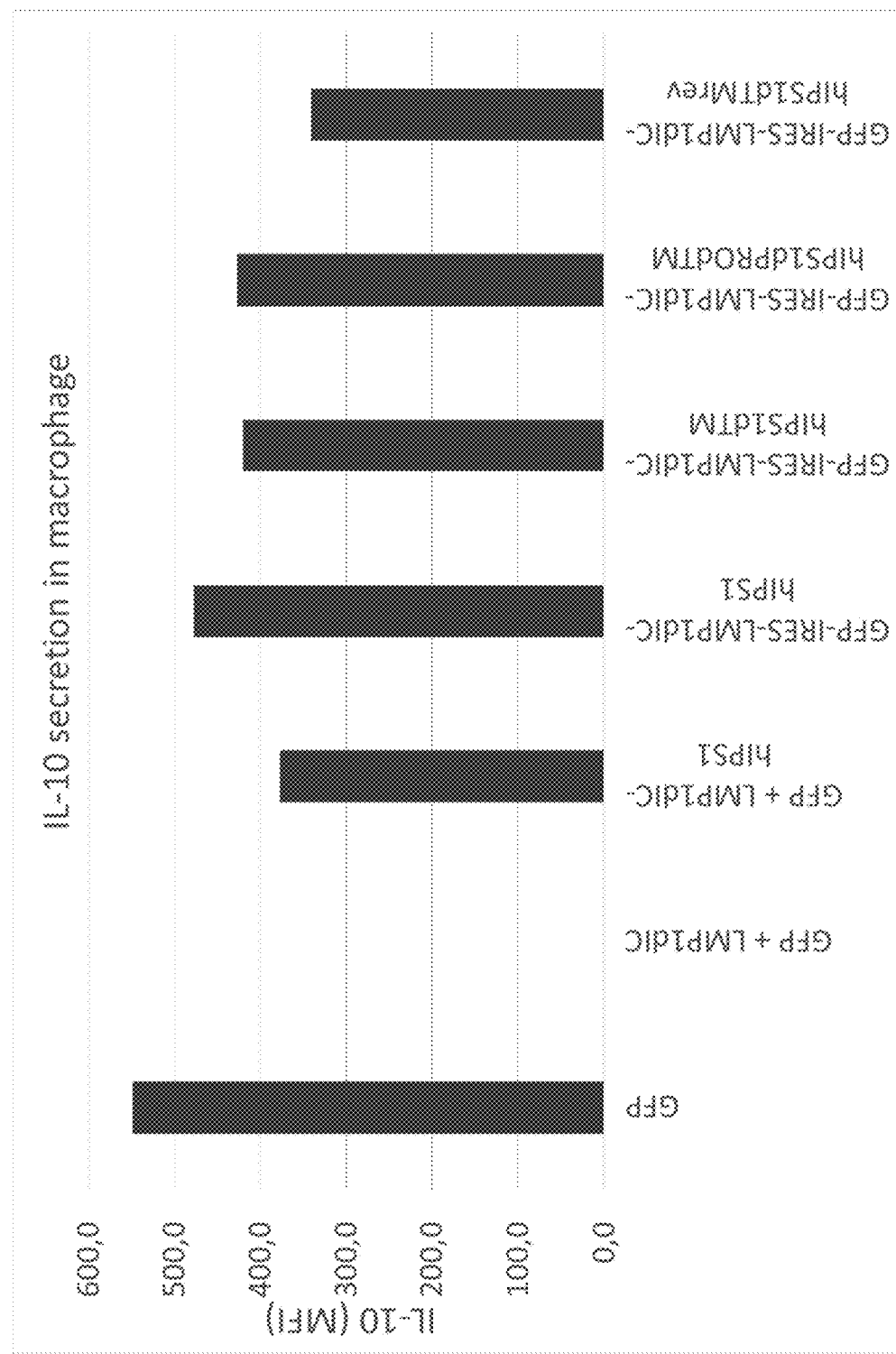
Figure 10C:
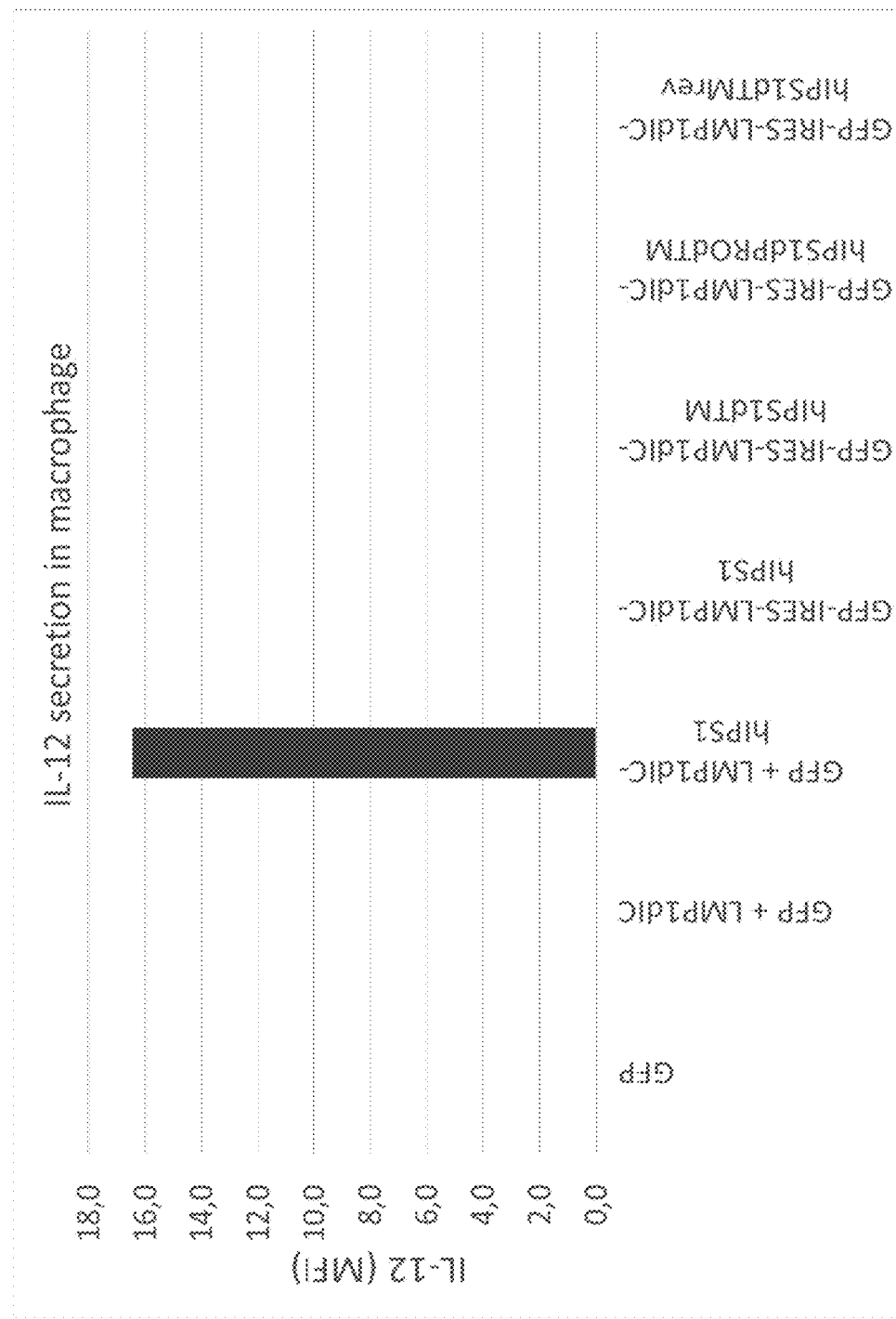
Figure 10C:
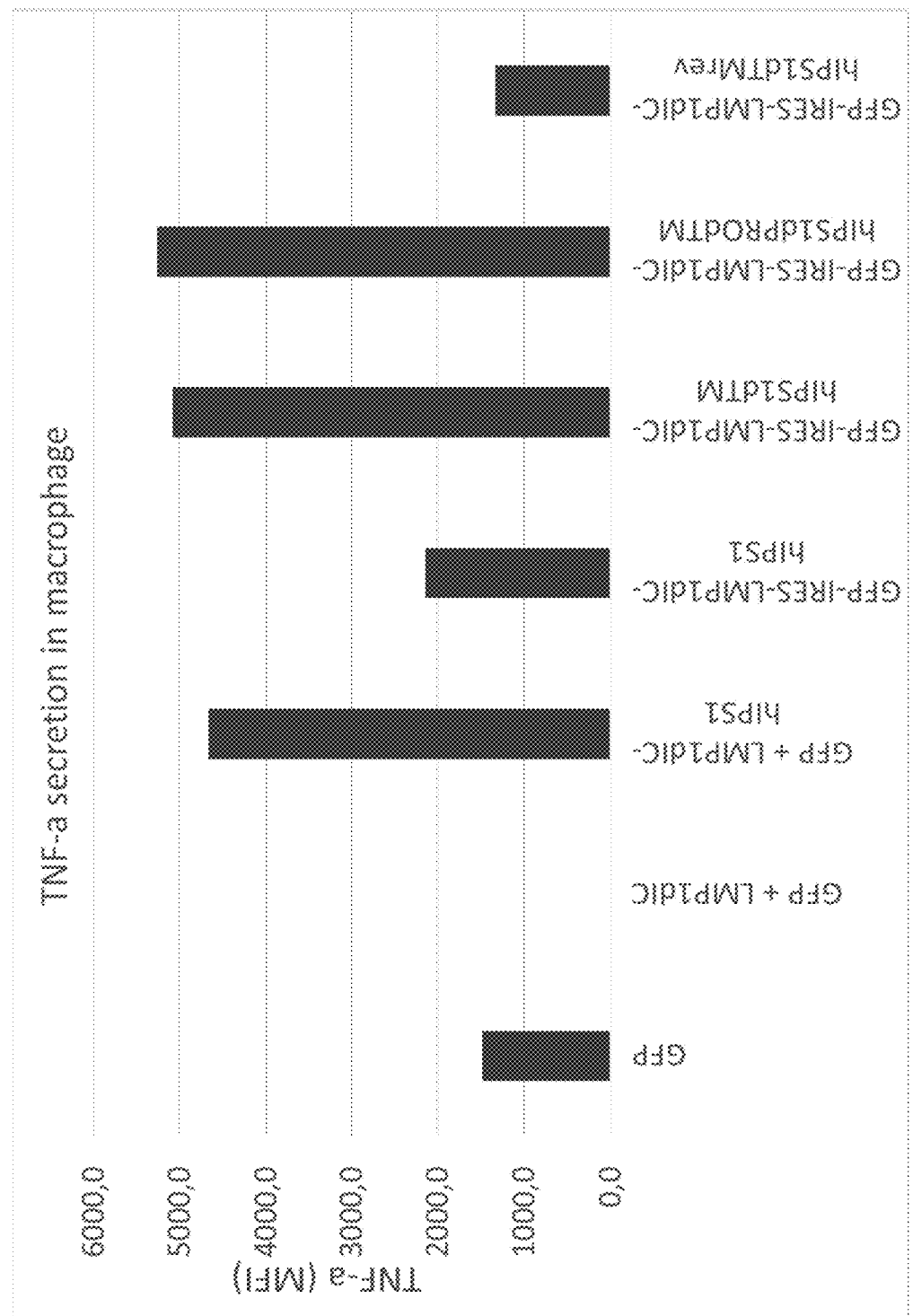
Figure 10D:
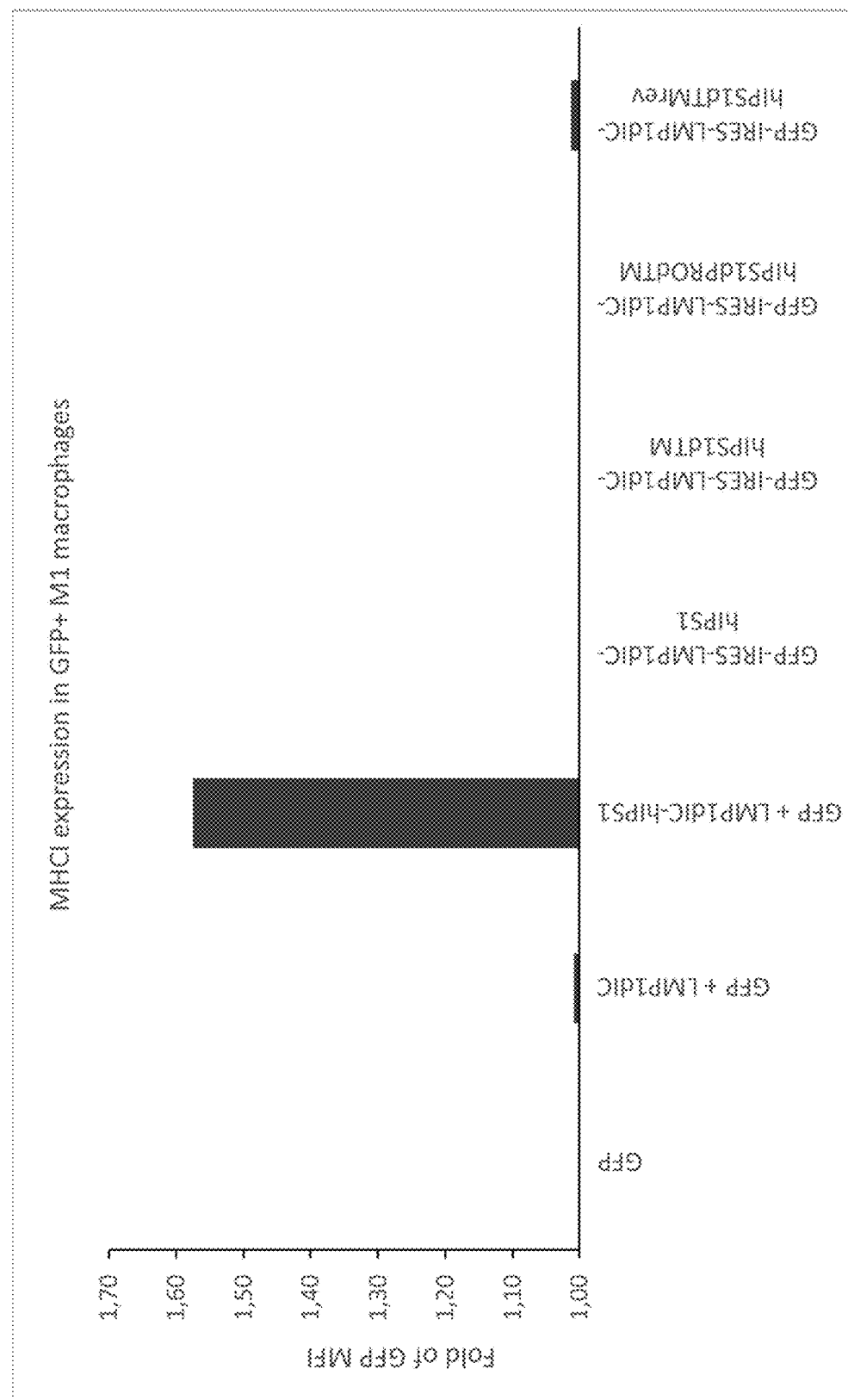
Figure 10D:
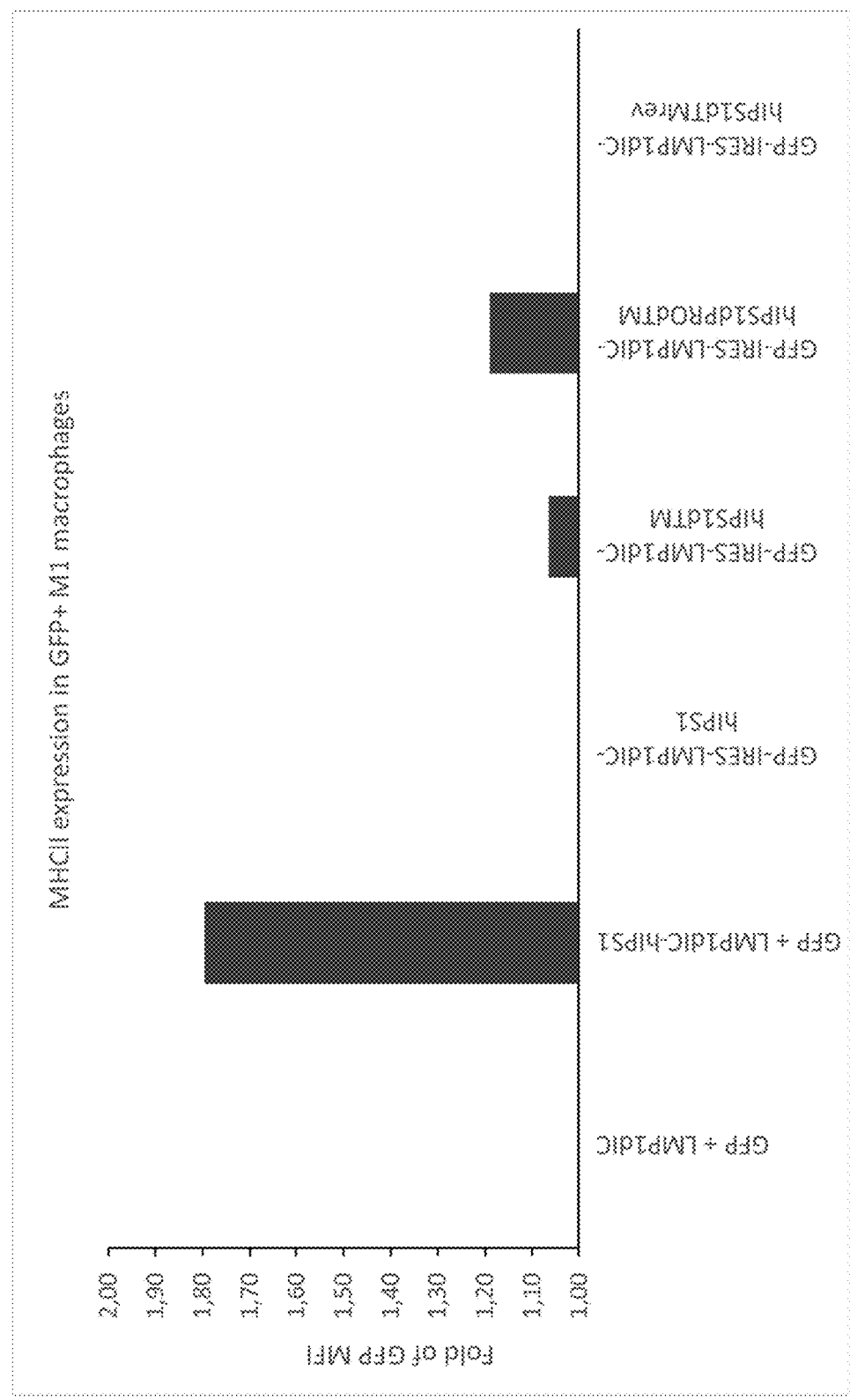
Figure 10D:
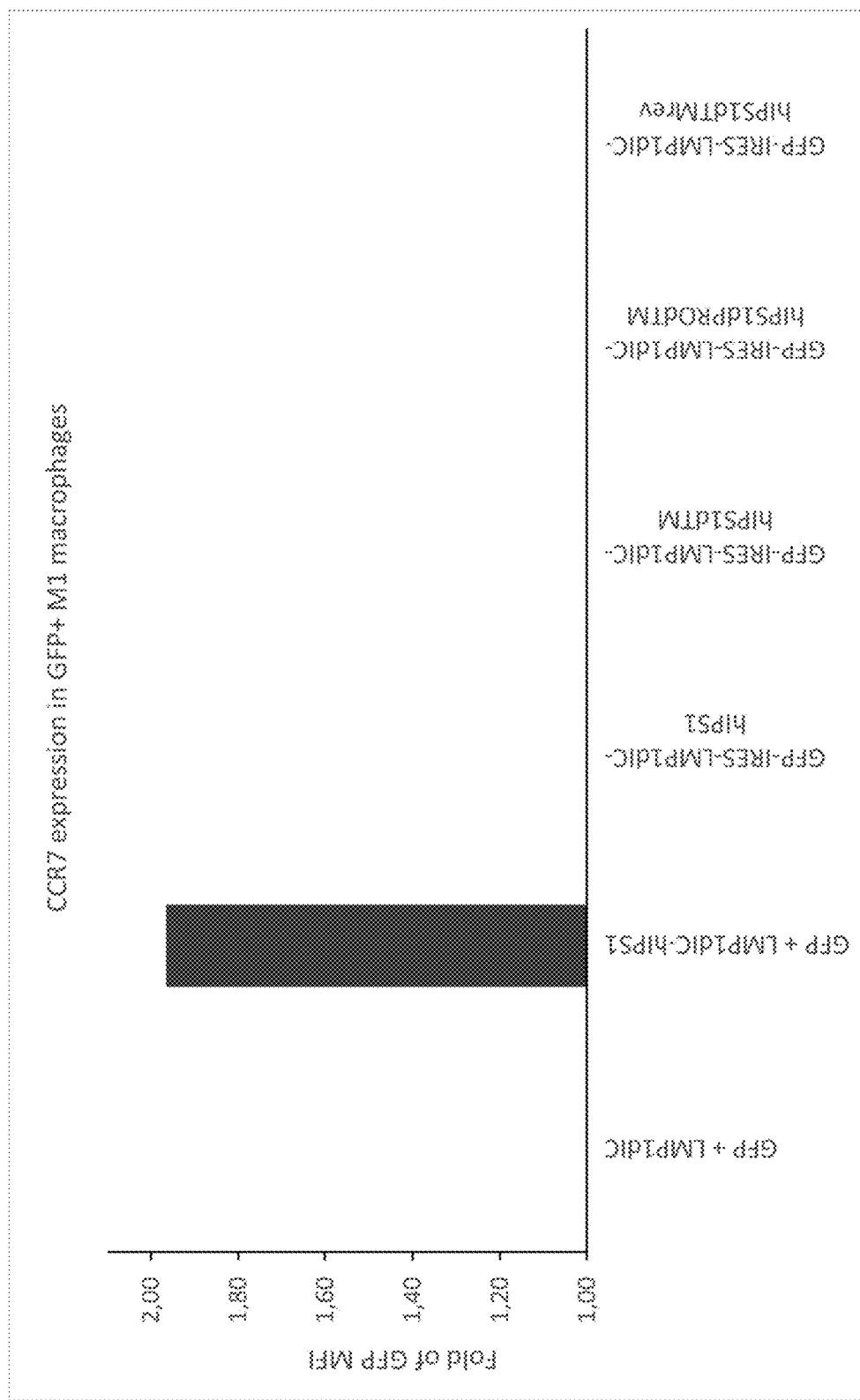
Figure 10D:
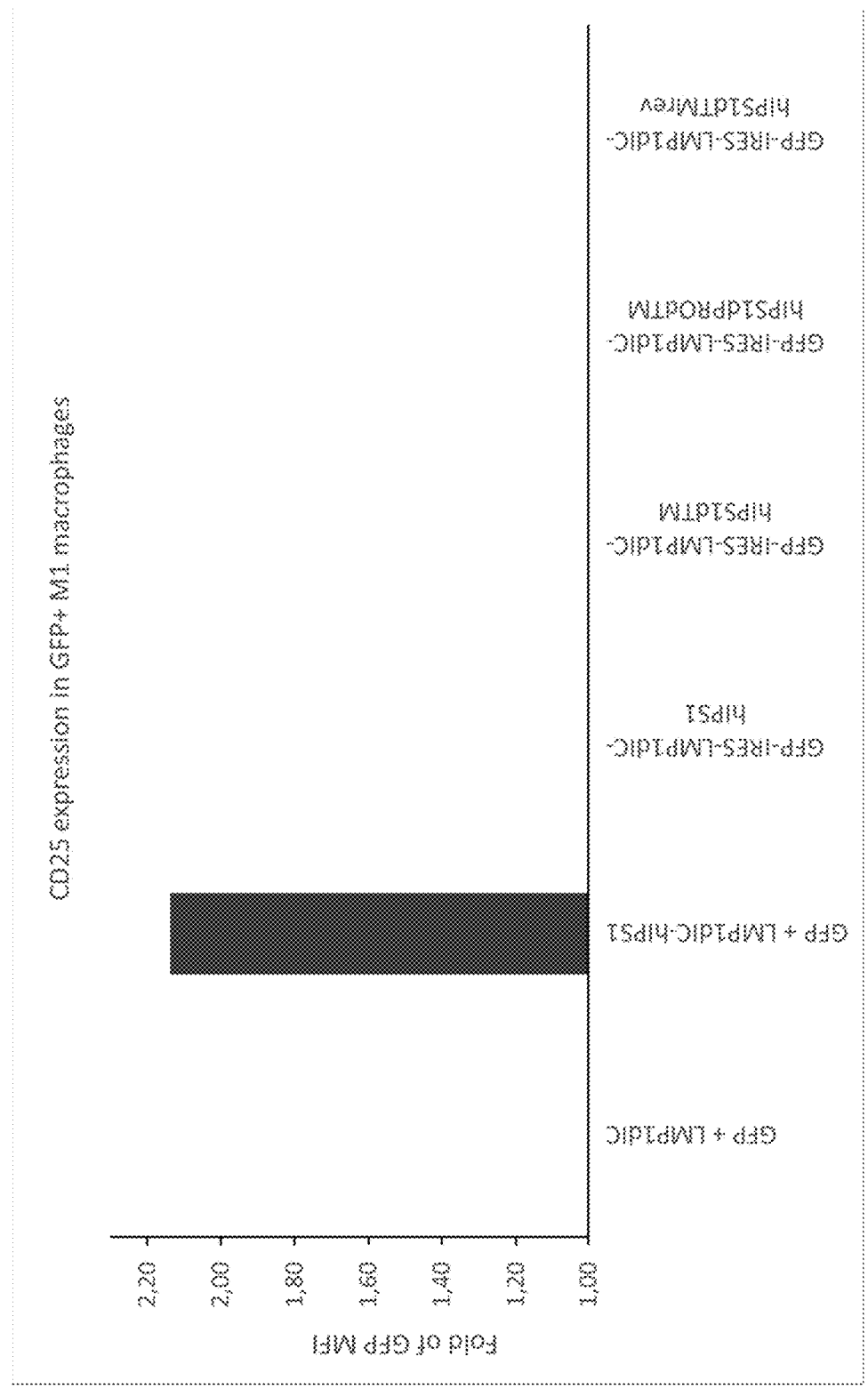
Figure 10D:
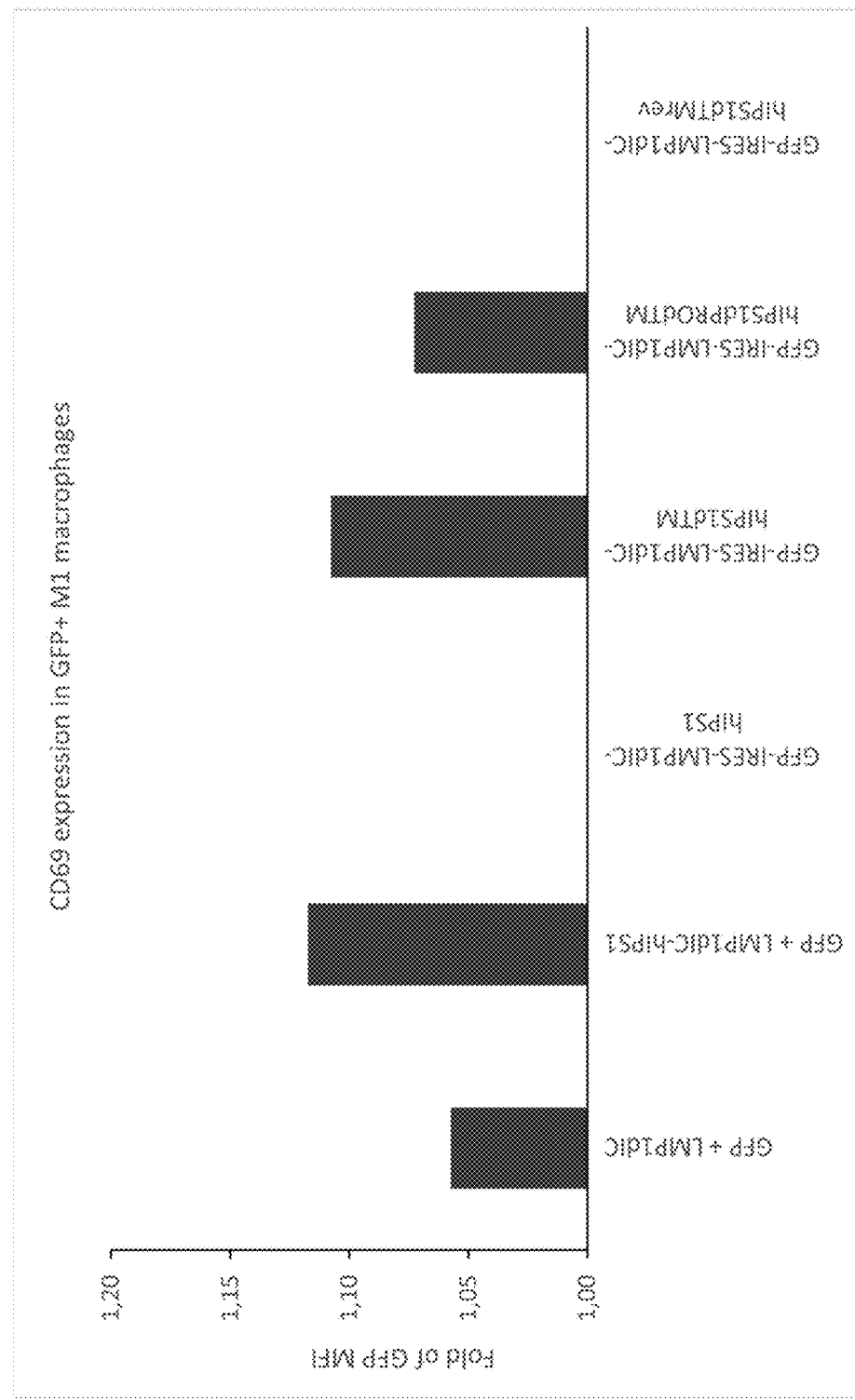
Figure 10D:
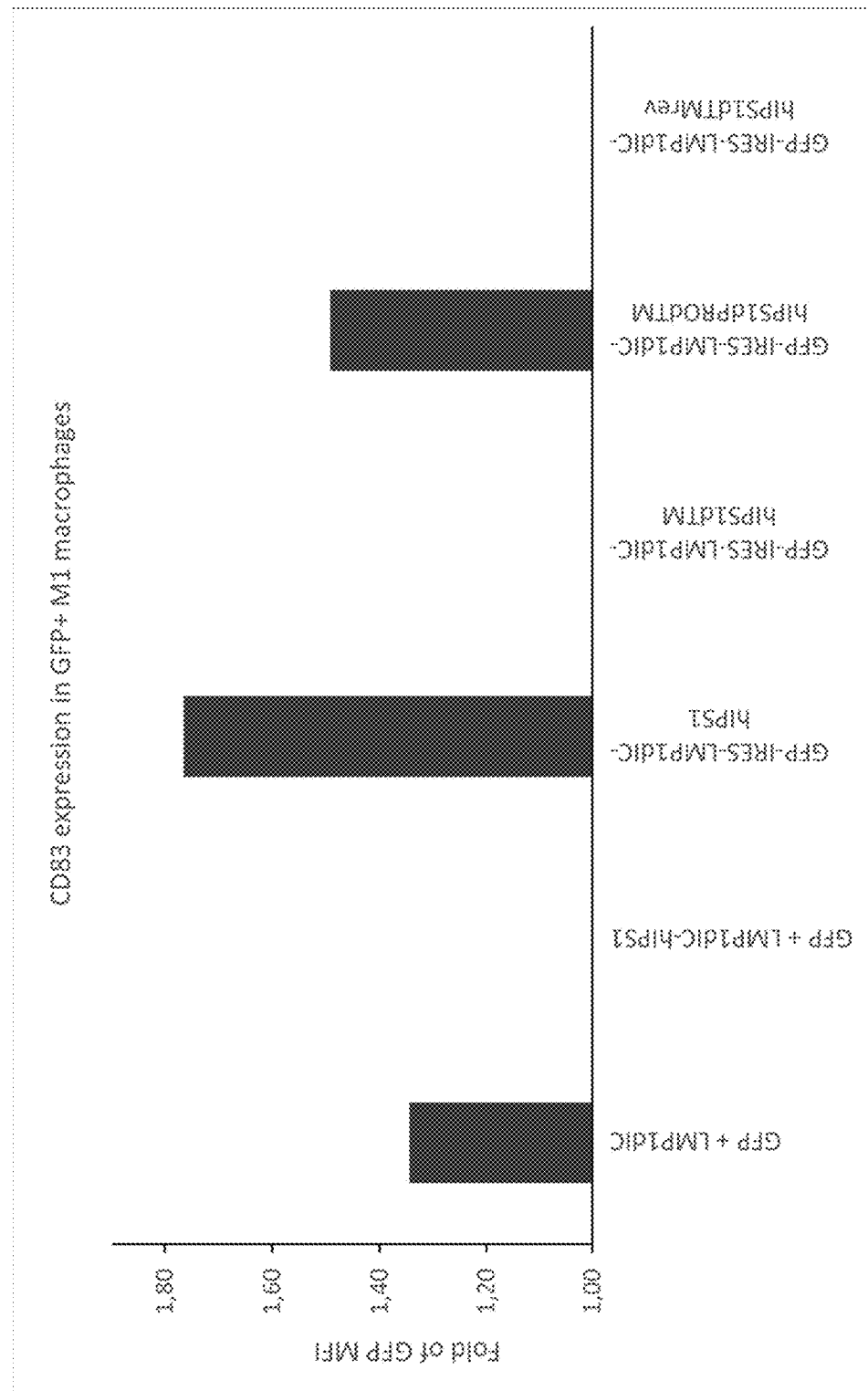
Figure 10D:
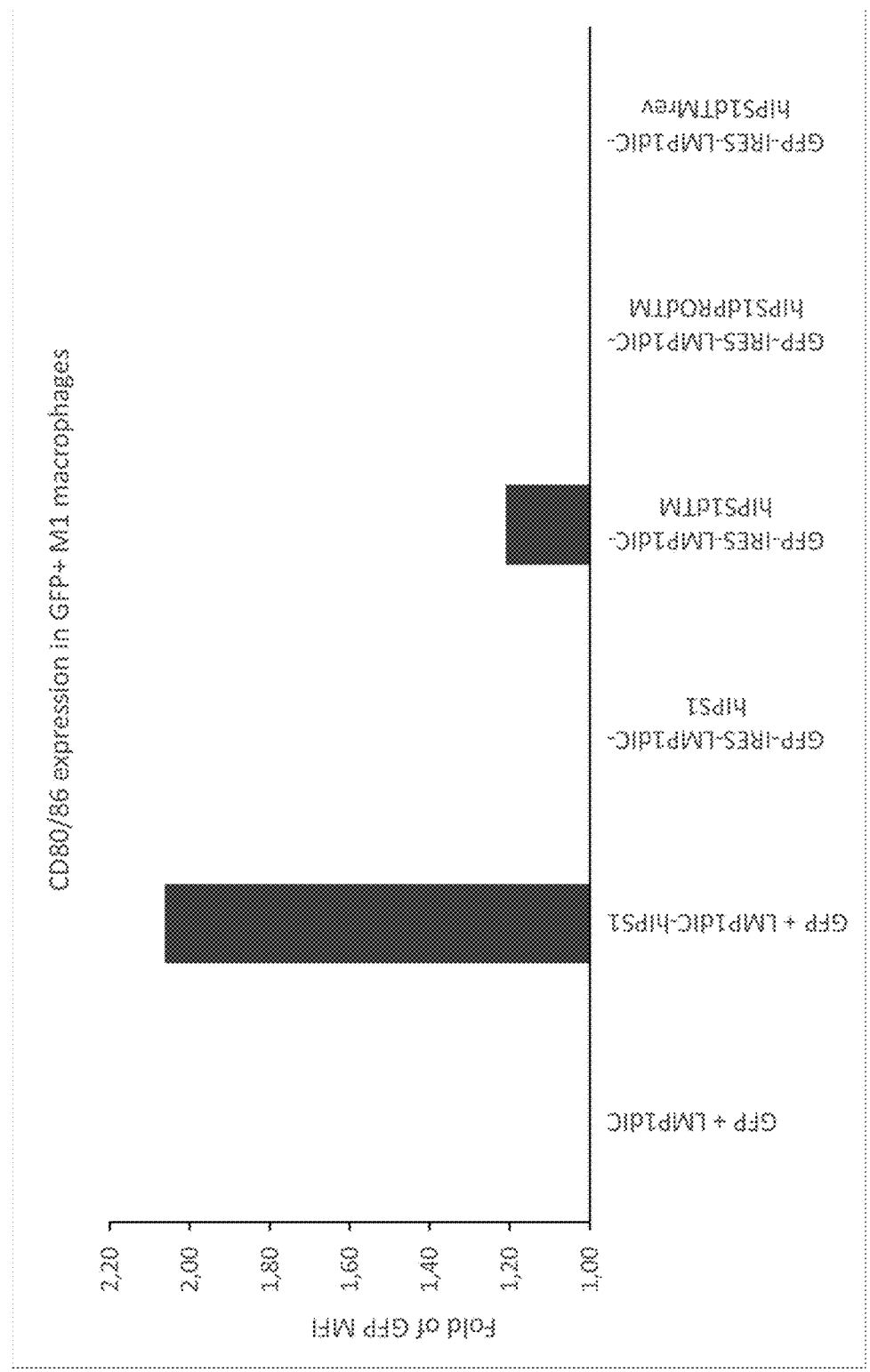
Figure 10D:
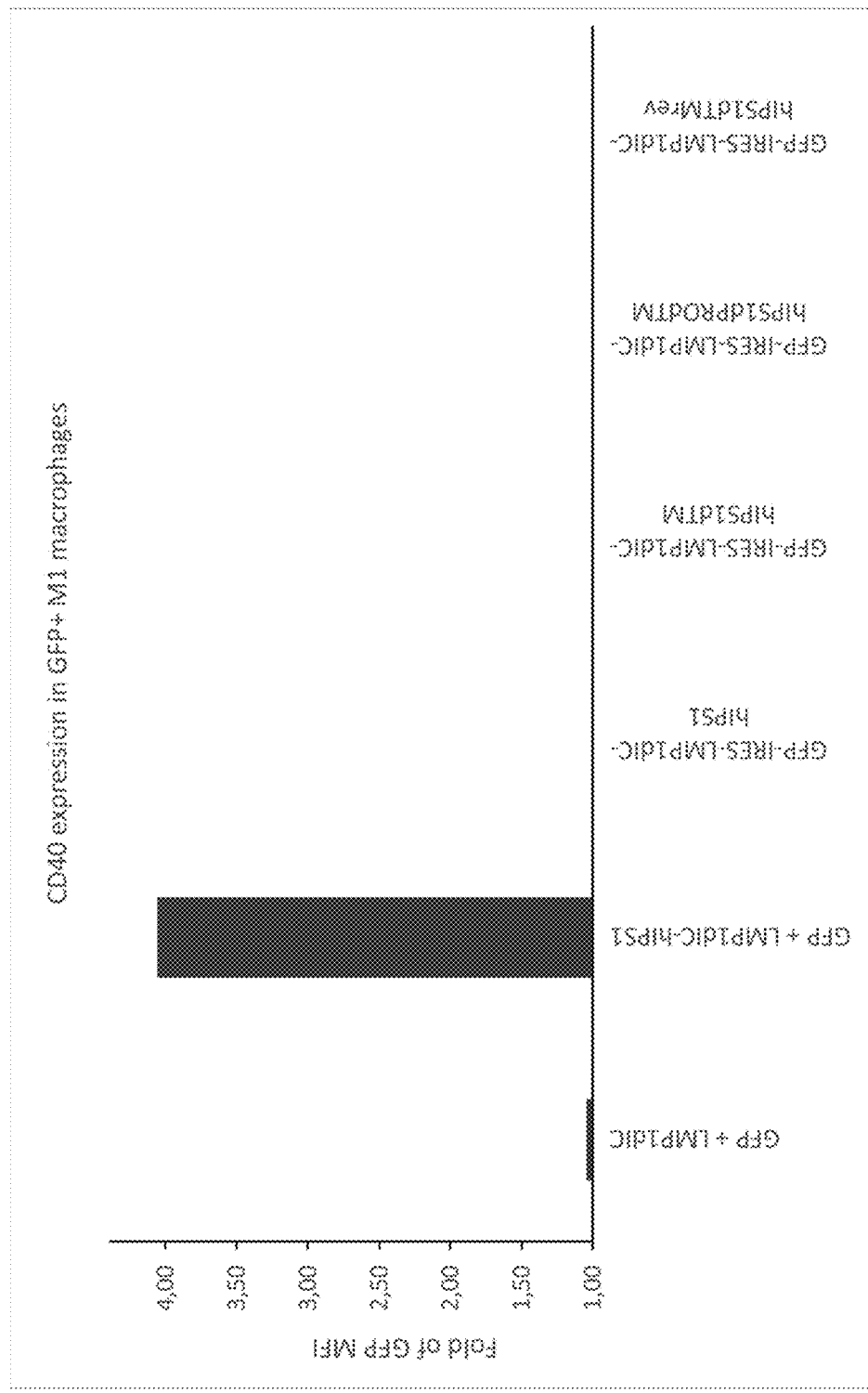

Activation and maturation of the dendritic cells and macrophages elicited by the lentiviral vectors were evaluated by measuring the expression of surface markers and assessing their cytokine and chemokine release profile. To determine levels of lentiviral integration and dendritic cells/macrophages activation, cells were harvested after 96 h culture, stained with a fixable viability dye and a panel of staining antibodies recognizing the following surface markers; CD25, CD40, CD69, CD80/86, CD83, CCR7, MHC I and MHC II, before analysis using a BD FACS Canto System flow cytometer. Cell frequencies and Geometric mean (Gmean) marker expression values were determined by gating on debris excluded/viable/single cells. All expression levels were normalized to the expression of GFP. For both dendritic cells and macrophages, activation of the STING pathway was assessed 96 h post-transduction by measuring the production in the culture supernatant of IFN-alpha and IFN-beta, as well as the immune-stimulatory cytokines IL-8, IL-1beta, TNF-alpha, IL-6, and IL-12p70 by Luminex analysis with a Bio-plex 200 System with high-throughput fluidics (BioRad). The production of immune-suppressive cytokine IL-10 was measured as control. Three independent experiments were carried out with PBMCs isolated from different healthy donors. Graphed data represent means of duplicates of a representative experiment. The results are presented in FIGS. 10A (dendritic cells, cytokines), 10B (dendritic cells, membrane markers), 10C (macrophages, cytokines), and 10D (macrophages, membrane markers).

For the transduced dendritic cells, results for expression of surface markers by GFP-positive cells showed that the IRES constructs upregulated the expression of the following immune activation molecules: MHCII (better with constructs 1 and 2); CD40 (increase 4-fold to 5-fold, especially with constructs 1 and 4); CD80/86 (constructs 1, 2. and 4); CD83 (3-fold to 4-fold increase with constructs 2 and 3, far better than control 3); and CCR7 migration signal (constructs 1 and 2, higher than control 3). Consistent with the upregulation of these activation surface markers increases in cytokine expression were as follows: pro-inflammatory IL-6 was stimulated with construct 2 and control 3; pro-inflammatory TNF-alpha increased with constructs 2 and 3 (better than controls 2 and 3); IL-12 increased with constructs 2 and 4 (better than control 2 and 3). Anti-inflammatory IL-10 levels were not affected by any of the evaluated constructs. The results for transduced dendritic cells indicated that the removal of the IPS1 transmembrane domain increased the activity of the adjuvant; the removal of the IPS1 transmembrane region and the proline rich (PRO) domain lightly increased the activity of the adjuvant; and removal of the IPS1 transmembrane domain while reversing the orientation of the IPS1 CARD and PRO domains did not show any immune stimulatory effect.

For the transduced macrophages, the results for expression of surface markers by GFP-positive cells showed that the IRES constructs upregulated the expression of the following immune activation molecules: CD83 increased significantly with constructs 1 and 3, better than control 2; CD80/86 increased in construct 2; and CD69 early activation marker was induced by constructs 2 and 3 at levels higher than control 3. In agreement with results observed in dendritic cells, enhanced expression of activation markers correlated with increases in cytokine expression as follows: pro-inflammatory IL-1beta increased 4-fold with constructs 2 and 4, as well as with control 3; pro-inflammatory IL-6 increased 4-fold with constructs 2 and 3, better than control 3; and pro-inflammatory TNF-alpha increased with constructs 2 and 3 (better than control 3). Anti-inflammatory IL-10 levels were not affected by any of the evaluated constructs.

In conclusion, the fusion of LMP1 transmembrane region with the human IPS1 protein increases the adjuvant effect on both dendritic cells and macrophages. Furthermore, optimization of the construct (removal of the transmembrane domain of the IPS1 protein, see FIG. 8B) increased the adjuvant activity.

When the proline rich region (PRO) is removed in addition to the removal of the transmembrane domain, the adjuvant effect was only slightly increased. The PRO region function is not well described, but it may play a role in the conformation of the IPS1 protein.

Removal of the IPS1 transmembrane domain while reversing the orientation of the IPS1 CARD and PRO domains showed a reduced immune stimulatory effect. This removal might lead to an incorrect conformation of the protein and a loss of activity.

Example 4. In Vivo Immunogenicity in Healthy Mice Treated with Single or Multiple Antigens Shows Superior Immunogenicity using LMP1-IPS1 Lentiviral Vectors Healthy mice are treated with different viral vectors containing expression cassettes encoding (a) human ubiquitin promoter; (b) one tumor antigen; and (c) a fusion of the transmembrane domain of LMP1 (codon optimized for human expression) and human IPS1, or a functional variant thereof. Experiments are performed to compare the immune response when the antigen and adjuvant (i.e., LMP1-IPS1 fusion) are expressed from different vectors vs. both expressed from the same vector after two administrations (prime+boost). Short- (3 weeks) and long-term (3 months) evaluation of in vivo immunogenicity is conducted by FACS analysis of mouse blood biomarkers (IFN-gamma and various interleukins), which allows for the detection and quantification of antigen-specific immune cells such as $CD4^+$, CD8+ and memory T cells targeting the antigen present into the vector. Treatment with lentiviral vector coding for an antigen(s) and LMP1-IPS1 is expected to increase specific immunogenicity when compared to the same lentiviral vectors without the LMP1-IPS1, or expressing only the membrane domain of LMP1. Further, a greater increase in immunogenicity is expected when expressing both the antigen and the adjuvant from the same vector compared to expression from different vectors.

Example 5. In Vivo Immunogenicity in Mouse Models of Specific Tumors Shows Superior Effectiveness of Lentiviral Vectors Containing a Combination of Multiple Antigens and LMP1-IPS 1 as Adjuvant Mouse models of specific tumors are treated with lentiviral vectors containing expression cassettes encoding (a) human ubiquitin as promoter; (b) a tumor-specific antigen; and a fusion of the transmembrane domain of LMP1 (codon optimized for human expression) and human IPS1, or a functional variant thereof. Mice are divided into different treatment groups according to vector type and construct, dose and number of injections. Experimental groups are administered (prime+boost injections) with vectors encoding: only the indication-specific antigen(s); only LMP1-IPS1 or indication-specific antigens, and LMP1-IPS1 (or a variant with a functional IPS1). In vivo efficacy and immunogenicity is evaluated by tumor growth rates, survival, and detection of antigen specific as CD4+, CD8+ and memory T cells by FACS analysis of mouse blood biomarkers (IFN-gamma and various interleukins). Lentiviral vectors encoding indication-specific antigens and LMP1-IPS1 fusion proteins are expected to induce the most potent and long-lasting immune response of all experimental groups, thus inducing a higher survival rate and/or lower tumor growth in the treated groups of mice.

Example 6. In Vivo Immunogenicity in Mouse Models of Specific Anticheckpoint Sensitive Tumors Shows Superior Effectiveness of Lentiviral Vectors Containing a Combination of Multiple Antigens, Adjuvant, and Anticheckpoint Mouse models of specific tumors are treated with lentiviral vectors containing expression cassettes encoding human ubiquitin as promoter and at least one of the following: an indication-specific antigen; LMP1-IPS1, and a soluble and secreted form of one or more anticheckpoint molecules. Mice are divided into different treatment groups according to vector constructs, dose, and number of injections. Experimental groups are administered (prime+boost injections) with vectors encoding: only the indication-specific antigen(s); only LMP1-IPS1; only one or more soluble and secreted anti-checkpoint molecules; indication-specific antigen and LMP1 (deltaIC); indication-specific antigen and LMP1 (deltaIC), and one or more soluble and secreted anticheckpoint molecules; indication-specific antigens and LMP1-IPS1 (or a variant with a functional IPS1); or indication-specific antigens and one or more soluble and secreted anticheckpoint molecules; or indication-specific antigens, LMP1-IPS1 or a variant with a functional IPS1), and one or more soluble and secreted anticheckpoint molecules. In vivo efficacy and immunogenicity is evaluated by tumor growth rates, survival, and detection of antigen specific as CD4+, CD8+ and memory T cells by FACS analysis of mouse blood biomarkers (IFN-gamma and various interleukins). Lentiviral vectors encoding indication-specific antigen, LMP1-IPS1 (or a variant with a functional IPS1), and anti-checkpoint molecules are expected to induce the most potent and long-lasting immune response of all experimental groups.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

The content of the ASCII text file of the sequence listing named "Sequence-Listing-24Jan2023-12268-0203", having a size of 35.5 kb and a creation date of 24 Jan. 2023, and electronically submitted via EFS-Web on 24 Jan. 2023, is incorporated herein by reference in its entirety.

REFERENCES

Barry, M. et al. Role of endogenous endonucleases and tissue site in transfection and CpG-mediated immune activation after naked DNA injection.
Hum Gene Ther, 10 (15) (1999), pp. 2461-2480.
McNamara, M. et al. RNA-Based Vaccines in Cancer Immunotherapy. J Immunol Res. 2015; 2015: 794528.
Nasri et al., Production, Purification and Titration of a Lentivirus-Based Vector for Gene Delivery Purposes, Cytotechnology 66,1031-8 (2014).

What is claimed is:

1. A viral vector comprising a first nucleic acid sequence encoding an antigen or an antigenic epitope and a second nucleic acid sequence encoding a fusion protein including the transmembrane portion of the latent membrane protein 1 (LMP1) of Epstein Barr virus in which the intra-cytoplasmic domain has been replaced by human IPS1 lacking its transmembrane domain, or a variant thereof, wherein transduction of a cell with the vector activates the STING pathway in the cell.

2. The viral vector of claim 1, wherein the vector is a lentiviral vector.

3. The viral vector of claim 1, wherein the first nucleic acid sequence encodes a fusion protein comprising two or more antigens or two or more antigenic epitopes.

4. The viral vector of claim 1, wherein the LMP1 intra-cytoplasmic domain has been replaced by a sequence encoding human IPS1 lacking its transmembrane domain and lacking its proline rich domain.

5. The viral vector of claim 1, wherein the second nucleic acid sequence comprises a sequence selected from the group consisting of SEQ ID NO. 1, SEQ ID NO:3, SEQ ID NO:5, and SEQ ID NO:7.

6. The viral vector of claim 1, wherein the vector further comprises a third nucleic acid sequence encoding a soluble immune checkpoint inhibitor molecule or a soluble immune modulator molecule.

7. The viral vector of claim 6, wherein the soluble immune checkpoint inhibitor molecule or the soluble immune modulator molecule is selected from the group consisting of CTLA-4, PD-1, PDL-1, LAG-3, TIM 3, B7-H3, ICOS, IDO, 4-1BB, CD47, B7-H4, OX-40, TIGIT, CD160 and combinations thereof.

8. The viral vector of claim 1, wherein the vector further comprises a functional lentiviral integrase protein, wherein the vector is self-inactivating.

9. The viral vector of claim 1, wherein the antigen is selected from the group consisting of NY-ESO-1, mesothelin, PSA, MART-1, MART-2, GP100, tyrosinase, p53, ras MUC1, SAP-1, survivin, CEA, Ep-CAM, Her2, BRCA1/2, gag, reverse transcriptase, tat, cicumsporozoite protein, HCV, nonstructural proteins, hemaglutinins, and combinations thereof.

10. An immunotherapeutic formulation for preventing or treating cancer or infection in a subject, the formulation comprising the viral vector of claim 1.

11. A method of inducing or enhancing an immune response against a cancer or an infectious disease in a subject, the method comprising administering the viral vector of claim 1 or the immunotherapeutic formulation of claim 9 to a subject in need thereof, whereby an immune response against said cancer or infectious disease is induced or enhanced in the subject.

12. The method of claim 11, whereby an immune response is induced or enhanced against a cancer, and the cancer is selected from the group consisting of: melanoma, glioma, prostate cancer, breast cancer, cervical cancer, colorectal cancer, kidney cancer, lung cancer, lymphoma and pancreatic cancer.

13. The method of claim 11, whereby an immune response is induced or enhanced against an infectious disease, and the infectious disease is selected from the group consisting of:
HIV/AIDS, hepatitis C, HPV, pneumonia, influenza, malaria, leishmaniosis, tuberculosis, Hansen's disease, rabies, dengue, Zika, Ebola, and schistosomiasis.

* * * * *

SEQUENCE LISTING

```
<160> NUMBER OF SEQ ID NOS: 8

<210> SEQ ID NO 1
<211> LENGTH: 2193
<212> TYPE: DNA
<213> ORGANISM: Artificial sequence
<220> FEATURE:
<223> OTHER INFORMATION: Fusion of LMP1 of Epstein Barr virus with IPS1
      of Homo sapiens

<400> SEQUENCE: 1
atggatctgg atctcgaaag aggacctcct ggacctagac ggcctcctag aggaccacct      60
ctgagcagct ctattggact ggccctgctg ctgcttctgc tggctctgct gttctggctg     120
tacatcatca tgagcaactg gaccggcgga gcactgctgg tgctgtatgc ctttgctctg    180
```

```
atgctggtca tcatcatcct gatcatcttc atcttccggc gggacctgct gtgtcctctg      240
ggagcacttt gtctgttgct gctgatgatc accctcctgc tgatcgccct gtggaacctg      300
catggacagg ccctgtatct gggcatcgtg ctgttcatct cggctgcct gctggttctc       360 ggcctgtgga tctacctgct ggaaatcctt tggagactgg cgccaccat ctggcagctg       420 ctggcctttt tcctggcctt ctttctggat atcatcctcc tcatcattgc cctgtacctg      480
cagcagaact ggtggaccct gctggtggat ctgctttggc tgctgctctt tctggccatc      540
ctgatttgga tgtactacca cggccagcgg cctttcgccg aggacaagac ctacaagtac      600
atctgccgga acttcagcaa cttctgcaac gtggacgtgg tggaaattct gccctacctg      660
ccttgcctga ccgccagaga tcaggacaga ctgagagcca catgtaccct gagcggcaac      720
agagacacac tgtggcacct gttcaacacc ctgcagagaa ggcctggctg ggtcgagtac      780
tttatcgccg ctctgagagg ctgcgagctg gtcgatctgg ctgatgaagt ggccagcgtg      840
taccagagct accagcctag aaccagcgac cggcctcctg atcctctcga acctccatct      900
ctgcccgccg aaagacctgg acctcctaca ccagctgccg ctcacagcat cccttacaac      960
agctgcagag agaagaacc tagctacccc atgcctgtgc aagagacaca ggccccagaa      1020
agccctggcg agaatagcga acaggctctg cagacactga gccccagagc cattcctaga      1080
aaccctgatg gcggccctct ggaaagctct agtgatctgg ccgctctgtc ccctctgaca      1140
agctctggac caagagca ggataccgag ctgggcagca cacatacagc cggcgctaca       1200
agcagcctga caccttctag aggccccgtg tctcccagcg tgtcatttca gcctctggcc      1260
aggtctaccc ctagggcttc tagactgcct ggaccaacag gcagcgtggt gtctaccggc      1320
acaagcttca gctctagctc tcctggactg gctagtgccg gtgccgctga gggaaaacaa      1380
ggcgccgaat ctgatcaggc cgagcctatc atctgtagca gcggagcaga agccctgcc      1440 aatagcctgc ctagcaaggt gccaaccaca ctgatgcccg tgaacacagt ggccctgaag      1500
gtgccagcta atcctgcctc cgtgtccacc gtgccttcta agctgccaac cagctctaag      1560
ccacctggcg ccgtgccatc taacgccctg acaaatcctg ctccaagcaa gctgcccatc      1620
aactccacaa gagccggcat ggtgccctct aaggtgccca catctatggt gctgaccaag      1680
gtgtccgcca gcaccgtgcc aacagatggc agctccagaa cgaggaaac ccctgccgct       1740 cctactcctg ctggcgctac aggcggatct tctgcttggc tggatagcag cagcgagaac      1800
agaggcctgg gcagcgagct ttctaaacct ggcgtgctgg cttcccaggt ggacagccca      1860
ttttccggct gctttgagga cctggctatc agcgcctcta caagcctcgg catgggacct      1920
tgtcacggcc ccgaggaaaa cgagtacaag agcgagggca ccttcggcat ccacgtggcc      1980
gagaatccta gcatccaact gctggaaggc aaccccggac tccagctga tccagatggc       2040 ggaccaagac tcaggccga cagaaagttc aagagcgcg aggtgccctg ccacagacct       2100
tctccaggtg ctctgtggct gcaggttgca gtgacaggcg tcctggtggt tacactgctc      2160
gtggtcctgt atagacggcg gctgcactga tga                                   2193
```

<210> SEQ ID NO 2
<211> LENGTH: 729
<212> TYPE: PRT
<213> ORGANISM: Artificial sequence
<220> FEATURE:
<223> OTHER INFORMATION: Fusion of LMP1 of Epstein Barr virus with IPS1 of Homo sapiens

```
<400> SEQUENCE: 2

Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
            35                  40                  45

Gly Gly Ala Leu Leu Val Leu Tyr Ala Phe Ala Leu Met Leu Val Ile
50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
            115                 120                 125

Ile Leu Trp Arg Leu Gly Ala Thr Ile Trp Gln Leu Leu Ala Phe Phe
130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
            165                 170                 175

Phe Leu Ala Ile Leu Ile Trp Met Tyr Tyr His Gly Gln Arg Pro Phe
            180                 185                 190

Ala Glu Asp Lys Thr Tyr Lys Tyr Ile Cys Arg Asn Phe Ser Asn Phe
            195                 200                 205

Cys Asn Val Asp Val Val Glu Ile Leu Pro Tyr Leu Pro Cys Leu Thr
            210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
            245                 250                 255

Trp Val Glu Tyr Phe Ile Ala Ala Leu Arg Gly Cys Glu Leu Val Asp
            260                 265                 270

Leu Ala Asp Glu Val Ala Ser Val Tyr Gln Ser Tyr Gln Pro Arg Thr
            275                 280                 285

Ser Asp Arg Pro Pro Asp Pro Leu Glu Pro Ser Leu Pro Ala Glu
290                 295                 300

Arg Pro Gly Pro Pro Thr Pro Ala Ala Ala His Ser Ile Pro Tyr Asn
305                 310                 315                 320

Ser Cys Arg Glu Lys Glu Pro Ser Tyr Pro Met Pro Val Gln Glu Thr
            325                 330                 335

Gln Ala Pro Glu Ser Pro Gly Glu Asn Ser Glu Gln Ala Leu Gln Thr
            340                 345                 350

Leu Ser Pro Arg Ala Ile Pro Arg Asn Pro Asp Gly Gly Pro Leu Glu
            355                 360                 365

Ser Ser Ser Asp Leu Ala Ala Leu Ser Pro Leu Thr Ser Ser Gly His
            370                 375                 380

Gln Glu Gln Asp Thr Glu Leu Gly Ser Thr His Thr Ala Gly Ala Thr
385                 390                 395                 400
```

Ser Ser Leu Thr Pro Ser Arg Gly Pro Val Ser Pro Ser Val Ser Phe
            405                 410                 415

Gln Pro Leu Ala Arg Ser Thr Pro Arg Ala Ser Arg Leu Pro Gly Pro
            420                 425                 430

Thr Gly Ser Val Val Ser Thr Gly Thr Ser Phe Ser Ser Ser Ser Pro
            435                 440                 445

Gly Leu Ala Ser Ala Gly Ala Ala Glu Gly Lys Gln Gly Ala Glu Ser
            450                 455                 460

Asp Gln Ala Glu Pro Ile Ile Cys Ser Ser Gly Ala Glu Ala Pro Ala
465                 470                 475                 480

Asn Ser Leu Pro Ser Lys Val Pro Thr Thr Leu Met Pro Val Asn Thr
            485                 490                 495

Val Ala Leu Lys Val Pro Ala Asn Pro Ala Ser Val Ser Thr Val Pro
            500                 505                 510

Ser Lys Leu Pro Thr Ser Ser Lys Pro Pro Gly Ala Val Pro Ser Asn
            515                 520                 525

Ala Leu Thr Asn Pro Ala Pro Ser Lys Leu Pro Ile Asn Ser Thr Arg
            530                 535                 540

Ala Gly Met Val Pro Ser Lys Val Pro Thr Ser Met Val Leu Thr Lys
545                 550                 555                 560

Val Ser Ala Ser Thr Val Pro Thr Asp Gly Ser Ser Arg Asn Glu Glu
            565                 570                 575

Thr Pro Ala Ala Pro Thr Pro Ala Gly Ala Thr Gly Gly Ser Ser Ala
            580                 585                 590

Trp Leu Asp Ser Ser Glu Asn Arg Gly Leu Gly Ser Glu Leu Ser
            595                 600                 605

Lys Pro Gly Val Leu Ala Ser Gln Val Asp Ser Pro Phe Ser Gly Cys
            610                 615                 620

Phe Glu Asp Leu Ala Ile Ser Ala Ser Thr Ser Leu Gly Met Gly Pro
625                 630                 635                 640

Cys His Gly Pro Glu Glu Asn Glu Tyr Lys Ser Glu Gly Thr Phe Gly
            645                 650                 655

Ile His Val Ala Glu Asn Pro Ser Ile Gln Leu Leu Glu Gly Asn Pro
            660                 665                 670

Gly Pro Pro Ala Asp Pro Asp Gly Gly Pro Arg Pro Gln Ala Asp Arg
            675                 680                 685

Lys Phe Gln Glu Arg Glu Val Pro Cys His Arg Pro Ser Pro Gly Ala
            690                 695                 700

Leu Trp Leu Gln Val Ala Val Thr Gly Val Leu Val Val Thr Leu Leu
705                 710                 715                 720

Val Val Leu Tyr Arg Arg Arg Leu His
            725

<210> SEQ ID NO 3
<211> LENGTH: 2106
<212> TYPE: DNA
<213> ORGANISM: Artificial sequence
<220> FEATURE:
<223> OTHER INFORMATION: Fusion of LMP1 of Epstein Barr virus with IPS1
      of Homo sapiens

<400> SEQUENCE: 3
atggatctgg atctcgaaag aggacctcct ggacctagac ggcctcctag aggaccacct      60
ctgagcagct ctattggact ggccctgctg ctgcttctgc tggctctgct gttctggctg     120

```
tacatcatca tgagcaactg gaccggcgga gcactgctgg tgctgtatgc ctttgctctg    180
atgctggtca tcatcatcct gatcatcttc atcttccggc gggacctgct gtgtcctctg    240
ggagcacttt gtctgttgct gctgatgatc accctcctgc tgatcgccct gtggaacctg    300
catggacagg ccctgtatct gggcatcgtg ctgttcatct tcggctgcct gctggttctc    360
ggcctgtgga tctacctgct ggaaatcctt tggagactgg gcgccaccat ctggcagctg    420
ctggcctttt tcctggcctt ctttctggat atcatcctcc tcatcattgc cctgtacctg    480
cagcagaact ggtggaccct gctggtggat ctgctttggc tgctgctctt tctggccatc    540
ctgatttgga tgtactacca cggccagcgg cctttcgccg aggacaagac ctacaagtac    600
atctgccgga acttcagcaa cttctgcaac gtggacgtgg tggaaattct gccctacctg    660
ccttgcctga ccgccagaga tcaggacaga ctgagagcca catgtaccct gagcggcaac    720
agagacacac tgtggcacct gttcaacacc ctgcagagaa ggcctggctg ggtcgagtac    780
tttatcgccg ctctgagagg ctgcgagctg gtcgatctgg ctgatgaagt ggccagcgtg    840
taccagagct accagcctag aaccagcgac cggcctcctg atcctctcga acctccatct    900
ctgcccgccg aaagacctgg acctcctaca ccagctgccg ctcacagcat cccttacaac    960
agctgcagag agaaagaacc tagctacccc atgcctgtgc aagagacaca ggccccagaa   1020
agccctggcg agaatagcga acaggctctg cagacactga gccccagagc cattcctaga   1080
aaccctgatg gcggccctct ggaaagctct agtgatctgg ccgctctgtc ccctctgaca   1140
agctctggac accaagagca ggataccgag ctgggcagca cacatacagc cggcgctaca   1200
agcagcctga caccttctag aggccccgtg tctcccagcg tgtcatttca gcctctggcc   1260
aggtctaccc ctagggcttc tagactgcct ggaccaacag gcagcgtggt gtctaccggc   1320
acaagcttca gctctagctc tcctggactg gctagtgccg tgccgctga gggaaaacaa    1380 ggcgccgaat ctgatcaggc cgagcctatc atctgtagca gcggagcaga agcccctgcc   1440
aatagcctgc ctagcaaggt gccaaccaca ctgatgcccg tgaacacagt ggccctgaag   1500
gtgccagcta atcctgcctc cgtgtccacc gtgccttcta agctgccaac cagctctaag   1560
ccacctggcg ccgtgccatc taacgccctg acaaatcctg ctccaagcaa gctgcccatc   1620
aactccacaa gagccggcat ggtgccctct aaggtgccca catctatggt gctgaccaag   1680
gtgtccgcca gcaccgtgcc aacagatggc agctccagaa cgaggaaaac ccctgccgct   1740
cctactcctg ctggcgctac aggcggatct tctgcttggc tggatagcag cagcgagaac   1800
agaggcctgg gcagcgagct ttctaaacct ggcgtgctgg cttcccaggt ggacagccca   1860
ttttccggct gctttgagga cctggctatc agcgcctcta caagcctcgg catgggacct   1920
tgtcacggcc ccgaggaaaa cgagtacaag agcgagggca ccttcggcat ccacgtggcc   1980
gagaatccta gcatccaact gctggaaggc aaccccggac tcccagctga tccagatggc   2040
ggaccaagac ctcaggccga cagaaagttc aagagcgcg aggtgccctg ccacagacct   2100
tctcca                                                                2106
```

<210> SEQ ID NO 4
<211> LENGTH: 702
<212> TYPE: PRT
<213> ORGANISM: Artificial sequence
<220> FEATURE:
<223> OTHER INFORMATION: Fusion of LMP1 of Epstein Barr virus with IPS1
      of Homo sapiens

<400> SEQUENCE: 4

```
Met Asp Leu Asp Leu Glu Arg Gly Pro Pro Gly Pro Arg Arg Pro Pro
1               5                   10                  15

Arg Gly Pro Pro Leu Ser Ser Ile Gly Leu Ala Leu Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
            165                 170                 175

Phe Leu Ala Ile Leu Ile Trp Met Tyr Tyr His Gly Gln Arg Pro Phe
        180                 185                 190

Ala Glu Asp Lys Thr Tyr Lys Tyr Ile Cys Arg Asn Phe Ser Asn Phe
            195                 200                 205

Cys Asn Val Asp Val Val Glu Ile Leu Pro Tyr Leu Pro Cys Leu Thr
        210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
            245                 250                 255

Trp Val Glu Tyr Phe Ile Ala Ala Leu Arg Gly Cys Glu Leu Val Asp
        260                 265                 270

Leu Ala Asp Glu Val Ala Ser Val Tyr Gln Ser Tyr Gln Pro Arg Thr
            275                 280                 285

Ser Asp Arg Pro Pro Asp Pro Leu Glu Pro Ser Leu Pro Ala Glu
290                 295                 300

Arg Pro Gly Pro Pro Thr Pro Ala Ala Ala His Ser Ile Pro Tyr Asn
305                 310                 315                 320

Ser Cys Arg Glu Lys Glu Pro Ser Tyr Pro Met Pro Val Gln Glu Thr
            325                 330                 335

Gln Ala Pro Glu Ser Pro Gly Glu Asn Ser Glu Gln Ala Leu Gln Thr
        340                 345                 350

Leu Ser Pro Arg Ala Ile Pro Arg Asn Pro Asp Gly Gly Pro Leu Glu
            355                 360                 365

Ser Ser Ser Asp Leu Ala Ala Leu Ser Pro Leu Thr Ser Ser Gly His
        370                 375                 380

Gln Glu Gln Asp Thr Glu Leu Gly Ser Thr His Thr Ala Gly Ala Thr
385                 390                 395                 400
```

Ser Ser Leu Thr Pro Ser Arg Gly Pro Val Ser Pro Ser Val Ser Phe
            405                 410                 415

Gln Pro Leu Ala Arg Ser Thr Pro Arg Ala Ser Arg Leu Pro Gly Pro
            420                 425                 430

Thr Gly Ser Val Val Ser Thr Gly Thr Ser Phe Ser Ser Ser Ser Pro
            435                 440                 445

Gly Leu Ala Ser Ala Gly Ala Ala Glu Gly Lys Gln Gly Ala Glu Ser
            450                 455                 460

Asp Gln Ala Glu Pro Ile Ile Cys Ser Ser Gly Ala Glu Ala Pro Ala
465                 470                 475                 480

Asn Ser Leu Pro Ser Lys Val Pro Thr Thr Leu Met Pro Val Asn Thr
            485                 490                 495

Val Ala Leu Lys Val Pro Ala Asn Pro Ala Ser Val Ser Thr Val Pro
            500                 505                 510

Ser Lys Leu Pro Thr Ser Ser Lys Pro Pro Gly Ala Val Pro Ser Asn
            515                 520                 525

Ala Leu Thr Asn Pro Ala Pro Ser Lys Leu Pro Ile Asn Ser Thr Arg
            530                 535                 540

Ala Gly Met Val Pro Ser Lys Val Pro Thr Ser Met Val Leu Thr Lys
545                 550                 555                 560

Val Ser Ala Ser Thr Val Pro Thr Asp Gly Ser Ser Arg Asn Glu Glu
            565                 570                 575

Thr Pro Ala Ala Pro Thr Pro Ala Gly Ala Thr Gly Gly Ser Ser Ala
            580                 585                 590

Trp Leu Asp Ser Ser Ser Glu Asn Arg Gly Leu Gly Ser Glu Leu Ser
            595                 600                 605

Lys Pro Gly Val Leu Ala Ser Gln Val Asp Ser Pro Phe Ser Gly Cys
            610                 615                 620

Phe Glu Asp Leu Ala Ile Ser Ala Ser Thr Ser Leu Gly Met Gly Pro
625                 630                 635                 640

Cys His Gly Pro Glu Glu Asn Glu Tyr Lys Ser Glu Gly Thr Phe Gly
            645                 650                 655

Ile His Val Ala Glu Asn Pro Ser Ile Gln Leu Leu Glu Gly Asn Pro
            660                 665                 670

Gly Pro Pro Ala Asp Pro Asp Gly Gly Pro Arg Pro Gln Ala Asp Arg
            675                 680                 685

Lys Phe Gln Glu Arg Glu Val Pro Cys His Arg Pro Ser Pro
            690                 695                 700

<210> SEQ ID NO 5
<211> LENGTH: 1953
<212> TYPE: DNA
<213> ORGANISM: Artificial sequence
<220> FEATURE:
<223> OTHER INFORMATION: Fusion of LMP1 of Epstein Barr virus with IPS1
      of Homo sapiens

<400> SEQUENCE: 5
atggatctgg atctcgaaag aggacctcct ggacctagac ggcctcctag aggaccacct    60
ctgagcagct ctattggact ggccctgctg ctgcttctgc tggctctgct gttctggctg   120
tacatcatca tgagcaactg gaccggcgga gcactgctgg tgctgtatgc ctttgctctg   180
atgctggtca tcatcatcct gatcatcttc atcttccggc gggacctgct gtgtcctctg   240
ggagcacttt gtctgttgct gctgatgatc accctcctgc tgatcgccct gtggaacctg   300

```
catggacagg ccctgtatct gggcatcgtg ctgttcatct tcggctgcct gctggttctc      360
ggcctgtgga tctacctgct ggaaatcctt tggagactgg gcgccaccat ctggcagctg      420
ctggcctttt tcctggcctt ctttctggat atcatcctcc tcatcattgc cctgtacctg      480
cagcagaact ggtggaccct gctggtggat ctgctttggc tgctgctctt tctggccatc      540
ctgatttgga tgtactacca cggccagcgg cctttcgccg aggacaagac ctacaagtac      600
atctgccgga acttcagcaa cttctgcaac gtggacgtgg tggaaattct gccctacctg      660
ccttgcctga ccgccagaga tcaggacaga ctgagagcca catgtaccct gagcggcaac      720
agagacacac tgtggcacct gttcaacacc ctgcagagaa ggcctggctg ggtcgagtac      780
tttatcgccg ctctgagagg ctgcgagctg gtcgatctgg ctgatgaagt ggccagcgtg      840
taccagagct accagcctag aaccagcgac cggggcgaga atagcgaaca ggctctgcag      900
acactgagcc ccagagccat cctagaaaac cctgatggcg ccctctggaa agctctagt       960
gatctggccg ctctgtcccc tctgacaagc tctggacacc aagagcagga taccgagctg     1020
ggcagcacac atacagccgg cgctacaagc agcctgacac cttctagagg ccccgtgtct     1080
cccagcgtgt catttcagcc tctggccagg tctaccccta gggcttctag actgcctgga     1140
ccaacaggca gcgtggtgtc taccggcaca agcttcagct ctagctctcc tggactggct     1200
agtgccggtg ccgctgaggg aaaacaaggc gccgaatctg atcaggccga gcctatcatc     1260
tgtagcagcg agcagaagcc cctgccaat  agcctgccta gcaaggtgcc aaccacactg     1320
atgcccgtga acacagtggc cctgaaggtg ccagctaatc ctgcctccgt gtccaccgtg     1380
ccttctaagc tgccaaccag ctctaagcca cctggcgccg tgccatctaa cgccctgaca     1440
aatcctgctc aagcaagct gcccatcaac tccacaagag ccggcatggt gccctctaag     1500
gtgcccacat ctatggtgct gaccaaggtg ccgccagca ccgtgccaac agatggcagc     1560
tccagaaacg aggaaacccc tgccgctcct actcctgctg gcgctacagg cggatcttct     1620
gcttggctgg atagcagcag cgagaacaga ggcctgggca gcgagctttc taaacctggc     1680
gtgctggctt cccaggtgga cagcccattt tccggctgct ttgaggacct ggctatcagc     1740
gcctctacaa gcctcggcat gggaccttgt cacggccccg aggaaaacga gtacaagagc     1800
gagggcacct tcggcatcca gtggccgag aatcctagca tccaactgct ggaaggcaac     1860
cccggacctc cagctgatcc agatggcgga ccaagacctc aggccgacag aaagttccaa     1920
gagcgcgagg tgccctgcca cagaccttct cca                                 1953
```

<210> SEQ ID NO 6
<211> LENGTH: 651
<212> TYPE: PRT
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 6

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60
```

-continued

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
            115                 120                 125

Ile Leu Trp Arg Leu Gly Ala Thr Ile Trp Gln Leu Leu Ala Phe Phe
            130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Pro Phe
            180                 185                 190

Ala Glu Asp Lys Thr Tyr Lys Tyr Ile Cys Arg Asn Phe Ser Asn Phe
            195                 200                 205

Cys Asn Val Asp Val Val Glu Ile Leu Pro Tyr Leu Pro Cys Leu Thr
210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
            245                 250                 255

Trp Val Glu Tyr Phe Ile Ala Ala Leu Arg Gly Cys Glu Leu Val Asp
            260                 265                 270

Leu Ala Asp Glu Val Ala Ser Val Tyr Gln Ser Tyr Gln Pro Arg Thr
            275                 280                 285

Ser Asp Arg Gly Glu Asn Ser Glu Gln Ala Leu Gln Thr Leu Ser Pro
290                 295                 300

Arg Ala Ile Pro Arg Asn Pro Asp Gly Gly Pro Leu Glu Ser Ser Ser
305                 310                 315                 320

Asp Leu Ala Ala Leu Ser Pro Leu Thr Ser Ser Gly His Gln Glu Gln
            325                 330                 335

Asp Thr Glu Leu Gly Ser Thr His Thr Ala Gly Ala Thr Ser Ser Leu
            340                 345                 350

Thr Pro Ser Arg Gly Pro Val Ser Pro Ser Val Ser Phe Gln Pro Leu
            355                 360                 365

Ala Arg Ser Thr Pro Arg Ala Ser Arg Leu Pro Gly Pro Thr Gly Ser
            370                 375                 380

Val Val Ser Thr Gly Thr Ser Phe Ser Ser Ser Pro Gly Leu Ala
385                 390                 395                 400

Ser Ala Gly Ala Ala Glu Gly Lys Gln Gly Ala Glu Ser Asp Gln Ala
            405                 410                 415

Glu Pro Ile Ile Cys Ser Ser Gly Ala Glu Ala Pro Ala Asn Ser Leu
            420                 425                 430

Pro Ser Lys Val Pro Thr Thr Leu Met Pro Val Asn Thr Val Ala Leu
            435                 440                 445

Lys Val Pro Ala Asn Pro Ala Ser Val Ser Thr Val Pro Ser Lys Leu
450                 455                 460

Pro Thr Ser Ser Lys Pro Pro Gly Ala Val Pro Ser Asn Ala Leu Thr
465                 470                 475                 480

```
Asn Pro Ala Pro Ser Lys Leu Pro Ile Asn Ser Thr Arg Ala Gly Met
                485                 490                 495

Val Pro Ser Lys Val Pro Thr Ser Met Val Leu Thr Lys Val Ser Ala
            500                 505                 510

Ser Thr Val Pro Thr Asp Gly Ser Ser Arg Asn Glu Glu Thr Pro Ala
        515                 520                 525

Ala Pro Thr Pro Ala Gly Ala Thr Gly Gly Ser Ser Ala Trp Leu Asp
    530                 535                 540

Ser Ser Ser Glu Asn Arg Gly Leu Gly Ser Glu Leu Ser Lys Pro Gly
545                 550                 555                 560

Val Leu Ala Ser Gln Val Asp Ser Pro Phe Ser Gly Cys Phe Glu Asp
                565                 570                 575

Leu Ala Ile Ser Ala Ser Thr Ser Leu Gly Met Gly Pro Cys His Gly
                580                 585                 590

Pro Glu Glu Asn Glu Tyr Lys Ser Gly Thr Phe Gly Ile His Val
                595                 600                 605

Ala Glu Asn Pro Ser Ile Gln Leu Leu Glu Gly Asn Pro Gly Pro Pro
    610                 615                 620

Ala Asp Pro Asp Gly Gly Pro Arg Pro Gln Ala Asp Arg Lys Phe Gln
625                 630                 635                 640

Glu Arg Glu Val Pro Cys His Arg Pro Ser Pro
                645                 650

<210> SEQ ID NO 7
<211> LENGTH: 2109
<212> TYPE: DNA
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 7
atggatctgg atctcgaaag aggacctcct ggacctagac ggcctcctag aggaccacct      60
ctgagcagct ctattggact ggccctgctg ctgcttctgc tggctctgct gttctggctg     120
tacatcatca tgagcaactg gaccggcgga gcactgctgg tgctgtatgc ctttgctctg     180
atgctggtca tcatcatcct gatcatcttc atcttccggc gggacctgct gtgtcctctg     240
ggagcacttt gtctgttgct gctgatgatc accctcctgc tgatcgccct gtggaacctg     300
catggacagg ccctgtatct gggcatcgtg ctgttcatct tcggctgcct gctggttctc     360
ggcctgtgga tctacctgct ggaaatcctt tggagactgg cgccaccat ctggcagctg     420 ctggcctttt tcctggcctt ctttctggat atcatcctcc tcatcattgc cctgtacctg     480
cagcagaact ggtggaccct gctggtggat ctgctttggc tgctgctctt tctggccatc     540
ctgatttgga tgtactacca cggccagcgg ccttctccaa gacactgccc agtggaaaga     600
gagcagttca gagggacgc ccagcctaga cctggcggag atcctgatgc ccacctgga     660 ccaaatggcg agctgctgca gatcagccct aatgaggccg tgcacatcgg cttcaccggc     720
gagtctaagt acgagaacga ggaacccggc cactgtcctg catgggcct ttctacatct     780 gcctctatcg ccctggacga gttctgcggc agctttccat ctgatgtgca gtctgccctc     840
gtgggcccta gtctctgga atctggcctg gcagaaacg agagcagctc cgatctgtgg     900
gctagctctg tgtgaacagc tggcgctcct acaccagccg ctcctaccga agagaataga     960
agcagcggcg acaccctgt gacaagcgcc tctgtgaaaa ccctggtcat gagcacccca    1020
```

-continued

```
gtgaagtccc cagtgatggg cgccagaacc tccaacattc ccctgaagtc tcccgctcct    1080
aacacactgg ccaactctcc agtggctggc cctcctaagt ctagcacccc tctgaaaagc    1140
cccgtgacct ctgtgtctgc ccctaacgct cctgtgaaac tggccgtgac caacgtgccc    1200
atgctgacca cacctgtgaa atccccactg agcaatgccc ctgccgaggc cggaagctct    1260
tgtatcattc ccgaggctca ggatagcgag gctggccaaa aaggcgaagc tgcaggcgct    1320
tctgctctgg gcctagctc tagctctttt agcaccggca ccagcgtggt gtctggcaca    1380
ccaggacctc tgagaagcgc cagacctacc tctagagccc tgcctcagtt tagcgtgtcc    1440
cctagtgtgc ctggcagaag ccctacactg tctagtacag ccggcgctac acacaccagc    1500
ggactggaaa cagaccaaga acagcatggc agcagcaccc tgccttctct ggctgccctt    1560
gattctagca cgaactgcc aggcggcgac cccaatagac ctatcgctag acctagcctg    1620
acacagctgg cccaagagag caatgagggc ccttctgagc ctgctcagac cgaacaggtg    1680
ccaatgcctt acagccccga aaagagcgg tgcagcaact accctatcag ccatgccgct    1740
gctcccacac ctcctggtcc aagagaagct cctctgagcc ctcctgagct gcccgatcct    1800
ccaagagata gcaccagacc tcagtactcc cagtacgtgt ccgccgtgga agatgccctg    1860
gatgtgctgg aatgtggcag actggccgcc atcttctacg aagtgtgggg ccctagaagg    1920
cagctgacca actttctgca ctggctgacc gacagaaacg gcagcctgac atgtaccgcc    1980
agactgagag atcaggaccg ggccacactg tgccctctgt atcctctgat cgaggtggtg    2040
gacgtgaact gcttcaacag cttcaaccgg tgcatctaca agtacaccaa ggacgaggct    2100
ttccctatg                                                            2109
```

<210> SEQ ID NO 8
<211> LENGTH: 703
<212> TYPE: PRT
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 8

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160
```

-continued

```
Gln Gln Asn Trp Trp Thr Leu Leu Val Asp Leu Leu Trp Leu Leu Leu
            165                 170                 175
Phe Leu Ala Ile Leu Ile Trp Met Tyr Tyr His Gly Gln Arg Pro Ser
        180                 185                 190
Pro Arg His Cys Pro Val Glu Arg Glu Gln Phe Lys Arg Asp Ala Gln
        195                 200                 205
Pro Arg Pro Gly Gly Asp Pro Asp Ala Pro Pro Gly Pro Asn Gly Glu
    210                 215                 220
Leu Leu Gln Ile Ser Pro Asn Glu Ala Val His Ile Gly Phe Thr Gly
225                 230                 235                 240
Glu Ser Lys Tyr Glu Asn Glu Glu Pro Gly His Cys Pro Gly Met Gly
                245                 250                 255
Leu Ser Thr Ser Ala Ser Ile Ala Leu Asp Glu Phe Cys Gly Ser Phe
            260                 265                 270
Pro Ser Asp Val Gln Ser Ala Leu Val Gly Pro Lys Ser Leu Glu Ser
        275                 280                 285
Gly Leu Gly Arg Asn Glu Ser Ser Asp Leu Trp Ala Ser Ser Gly
    290                 295                 300
Gly Thr Ala Gly Ala Pro Thr Pro Ala Ala Pro Thr Glu Glu Asn Arg
305                 310                 315                 320
Ser Ser Gly Asp Thr Pro Val Thr Ser Ala Ser Val Lys Thr Leu Val
                325                 330                 335
Met Ser Thr Pro Val Lys Ser Pro Val Met Gly Ala Arg Thr Ser Asn
            340                 345                 350
Ile Pro Leu Lys Ser Pro Ala Pro Asn Thr Leu Ala Asn Ser Pro Val
        355                 360                 365
Ala Gly Pro Pro Lys Ser Ser Thr Pro Leu Lys Ser Pro Val Thr Ser
    370                 375                 380
Val Ser Ala Pro Asn Ala Pro Val Lys Leu Ala Val Thr Asn Val Pro
385                 390                 395                 400
Met Leu Thr Thr Pro Val Lys Ser Pro Leu Ser Asn Ala Pro Ala Glu
                405                 410                 415
Ala Gly Ser Ser Cys Ile Ile Pro Glu Ala Gln Asp Ser Glu Ala Gly
            420                 425                 430
Gln Lys Gly Glu Ala Ala Gly Ala Ser Ala Leu Gly Pro Ser Ser Ser
        435                 440                 445
Ser Phe Ser Thr Gly Thr Ser Val Val Ser Gly Thr Pro Gly Pro Leu
    450                 455                 460
Arg Ser Ala Arg Pro Thr Ser Arg Ala Leu Pro Gln Phe Ser Val Ser
465                 470                 475                 480
Pro Ser Val Pro Gly Arg Ser Pro Thr Leu Ser Ser Thr Ala Gly Ala
                485                 490                 495
Thr His Thr Ser Gly Leu Glu Thr Asp Gln Glu Gln His Gly Ser Ser
            500                 505                 510
Thr Leu Pro Ser Leu Ala Ala Leu Asp Ser Ser Ser Glu Leu Pro Gly
        515                 520                 525
Gly Asp Pro Asn Arg Pro Ile Ala Arg Pro Ser Leu Thr Gln Leu Ala
    530                 535                 540
Gln Glu Ser Asn Glu Gly Pro Ser Glu Pro Ala Gln Thr Glu Gln Val
545                 550                 555                 560
Pro Met Pro Tyr Ser Pro Glu Lys Glu Arg Cys Ser Asn Tyr Pro Ile
                565                 570                 575
```

-continued

```
Ser His Ala Ala Ala Pro Thr Pro Pro Gly Pro Arg Glu Ala Pro Leu
            580                 585                 590

Ser Pro Pro Glu Leu Pro Asp Pro Arg Asp Ser Thr Arg Pro Gln
        595                 600                 605

Tyr Ser Gln Tyr Val Ser Ala Val Glu Asp Ala Leu Asp Val Leu Glu
    610                 615                 620

Cys Gly Arg Leu Ala Ala Ile Phe Tyr Glu Val Trp Gly Pro Arg Arg
625                 630                 635                 640

Gln Leu Thr Asn Phe Leu His Trp Leu Thr Asp Arg Asn Gly Ser Leu
                645                 650                 655

Thr Cys Thr Ala Arg Leu Arg Asp Gln Asp Arg Ala Thr Leu Cys Pro
            660                 665                 670

Leu Tyr Pro Leu Ile Glu Val Val Asp Val Asn Cys Phe Asn Ser Phe
        675                 680                 685

Asn Arg Cys Ile Tyr Lys Tyr Thr Lys Asp Glu Ala Phe Pro Met
690                 695                 700
```